United States Patent [19]
Guthikonda et al.

[11] Patent Number: 5,629,322
[45] Date of Patent: May 13, 1997

[54] CYCLIC AMIDINE ANALOGS AS INHIBITORS OF NITRIC OXIDE SYNTHASE

[75] Inventors: Ravindra N. Guthikonda, Edison; Stephan K. Grant, Robbinsville; Malcolm Maccoss, Freehold; Shrenik K. Shah, Metuchen; Kothandaraman Shankaran, Kendall Park; Charles G. Caldwell, Scotch Plains; Philippe L. Durette, New Providence, all of N.J.

[73] Assignee: Merck & Co., Inc., Rahway, N.J.

[21] Appl. No.: 468,120

[22] Filed: Jun. 6, 1995

Related U.S. Application Data

[63] Continuation-in-part of Ser. No. 339,607, Nov. 15, 1994, abandoned.

[51] Int. Cl.$^6$ .......................... A61K 31/47; C07D 215/38
[52] U.S. Cl. .......................... 514/313; 514/249; 544/356; 546/159
[58] Field of Search .......................... 544/51, 105, 353, 544/354, 355, 356; 546/153, 155, 156, 159, 160; 514/249, 313

[56] References Cited

FOREIGN PATENT DOCUMENTS

WO95/11231  4/1995  WIPO .

OTHER PUBLICATIONS

Unkovskii, B.V. et al, Khim. Geterotsikl. Soedin. 1992, 10, 1433-7.

*Primary Examiner*—C. Warren Ivy
*Assistant Examiner*—Garth M. Dahlen
*Attorney, Agent, or Firm*—Curtis C. Panzer; David L. Rose

[57] ABSTRACT

Disclosed herein are compounds of Formula I

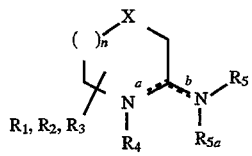

and pharmaceutically acceptable salts thereof which have been found useful in the treatment of nitric oxide synthase mediated diseases and disorders, including neurodegenerative disorders, disorders of gastrointestinal motility and inflammation. These disease and disorders include hypotension, septic shock, toxic shock syndrom, hemodialysis, IL-2 therapy such as in cancer patients, cachexia, immunosuppression such as in transplant therapy, autoimmune and/or inflammatory indications including sunburn or psoriasis and respiratory conditions such as bronchitis, asthma, and acure respiratory distress (ARDS), myocarditis, heart failure, atherosclerosis, arthritis, rheumatoid arthritis, chronic or inflammatory bowel disease, ulcerative colitis, Crohn's disease, systemic lupus erythematosis (SLE), ocular conditions such as ocular hypertension and uveitis, type 1 diabetes, insulin-dependent diabetes mellitus and cystic fibrosis. Compounds of Formula I are also usful in the treatment of hypoxia, hyperbaric oxygen convulsions and toxicity, dementia, Sydenham's chorea, Parkinson's disease, Huntington's disease, amyotrophic lateral sclerosis, mulitple sclerosis, Korsakoff's disease, imbecility related to cerebral vessel disorder, ischemic brain edema, sleeping disorders, schizophrenia, depression, PMS, anxiety, drug addiction, pain, migraine, immune complex disease, as immunosupressive agents and for preventing or reversing tolerance to opiates and diazepines.

16 Claims, No Drawings

000# CYCLIC AMIDINE ANALOGS AS INHIBITORS OF NITRIC OXIDE SYNTHASE

RELATED APPLICATION DATA

This Application is a Continuation-In-Part of U.S. application Ser. No. 08/339,607 filed Nov. 15, 1994 (abandoned).

BACKGROUND OF THE INVENTION

This application is directed to inhibitors of Nitric oxide synthase, and in particular cyclic amidines.

Nitric Oxide in Biology.

The emergence of nitric oxide (NO), a reactive, inorganic radical gas as a molecule contributing to important physiological and pathological processes is one of the major biological revelations of recent times. This molecule is produced under a variety of physiological and pathological conditions by cells mediating vital biological functions. Examples include endothelial cells lining the blood vessels; nitric oxide derived from these cells relaxes smooth muscle and regulates blood pressure and has significant effects on the function of circulating blood cells such as platelets and neutrophils as well as on smooth muscle, both of the blood vessels and also of other organs such as the airways. In the brain and elsewhere nitric oxide serves as a neurotransmitter in non-adrenergic non-cholinergic neurons. In these instances nitric oxide appears to be produced in small amounts on an intermittent basis in response to various endogenous molecular signals. In the immune system nitric oxide can be synthesized in much larger amounts on a protracted basis. Its production is induced by exogenous or endogenous inflammatory stimuli, notably endotoxin and cytokines elaborated by cells of the host defense system in response to infectious and inflammatory stimuli. This induced production results in prolonged nitric oxide release which contributes both to host defense processes such as the killing of bacteria and viruses as well as pathology associated with acute and chronic inflammation in a wide variety of diseases. The discovery that nitric oxide production is mediated by a unique series of three closely related enzymes, named nitric oxide synthases, which utilize the amino acid arginine and molecular oxygen as co-substrates has provided an understanding of the biochemistry of this molecule and provides distinct pharmacological targets for the inhibition of the synthesis of this mediator, which should provide significant beneficial effects in a wide variety of diseases.

Nitric Oxide Synthases

Nitric oxide and L-citrulline are formed from L-arginine via the dioxygenase activity of specific nitric oxide synthases (NOSs) in mammalian cells. In this reaction, L-arginine, $O_2$ and NADPH are cosubstrates while FMN, FAD and tetrahydrobiopterin are cofactors. NOSs fall into two distinct classes, constitutive NOS (cNOS) and inducible NOS (iNOS). Two constitutive NOSs have been identified. They are:

(i) a constitutive, $Ca^{++}$/calmodulin dependent enzyme, located in the endothelium (ecNOS or NOS 3), that releases NO in response to receptor or physical stimulation, (ii) a constitutive, $Ca^{++}$/calmodulin dependent enzyme, located in the brain (ncNOS or NOS 1) and elsewhere, that releases NO in response to receptor or physical stimulation, The third isoform identified is inducible NOS (iNOS or NOS 2):

(iii) a $Ca^{++}$ independent enzyme which is induced after activation of vascular smooth muscle, macrophages, endothelial cells, and a large number of other cells by endotoxin and cytokines. Once expressed, this inducible NO synthase produces NO in relatively large amounts for long periods of time.

Spectral studies of both the mouse macrophage iNOS and rat brain ncNOS have shown that these enzymes (which has been classified as P-450-like enzymes from their CO-difference spectra) contain a heme moiety. The structural similarity between NOS and the P-450/flavoprotein complex suggests that the NOS reaction mechanism may be similar to P-450 hydroxylation and/or peroxidation. This indicates that NOS belongs to a class of flavohemeproteins which contain both heme and flavin binding regions within a single protein in contrast to the multiprotein NADPH oxidase or Cytochrome P-450/NADPH Cyt c reductase complexes.

Distinct Functions of NO Produced by Different Nitric Oxide Synthases.

The NO released by the constitutive enzymes (NOS 1 and NOS 3) acts as an autocoid mediating a number of physiological responses. Two distinct cDNAs accounting for the activity of NOS 1 and NOS 3 in man have been cloned, one for NOS 1 (Nakane et. al., *FEBS Letters*, 316, 175–182, 1993) which is present in the brain and a number of peripheral tissues, the other for an enzyme present in endothelium (NOS 3) (Marsden et. al., *FEBS Letters*, 307, 287–293, 1992). This latter enzyme is critical for production of NO to maintain vasorelaxation. A second class of enzyme, iNOS or NOS 2, has been cloned from human liver (Geller et. al., *PNAS,* 90, 3491–5, 1993), and identified in more than a dozen other cells and tissues, including smooth muscle cells, chondrocytes, the kidney and airways. As with its counterpart from the murine macrophage, this enzyme is induced upon exposure to cytokines such as gamma interferon (IFN-γ), interleukin-1β (IL-1β), tumor necrosis factor (TNF-α) and LPS (lipopolysaccharide). Once induced, iNOS expression continues over a prolonged period of time. The enzyme does not require exogenous calmodulin for activity.

Endothelium derived relaxation factor (EDRF) has been shown to be produced by NOS 3 (Moncada et. al., *Pharmacol. Reviews*, 43, 109–142, 1991). Studies with substrate analog inhibitors of NOS have shown a role for NO in regulating blood pressure in animals and blood flow in man, a function attributed to NOS 3. NO has also been shown to be an effector of the cytotoxic effects of activated macrophages (Nathan, *FASEB J.,* 6, 3051–64, 1992) for fighting tumour cells and invading microorganisms (Wright et al., *Card. Res.,* 26,48–57, 1992 and Moncada et al., *Pharmacological Review,* 43, 109–142, 1991). It also appears that the adverse effects of excess NO production, in particular pathological vasodilation and tissue damage, may result largely from the effects of NO synthesized by the NOS 2.

NO generated by NOS 2 has been implicated in the pathogenesis of inflammatory diseases. In experimental animals hypotension induced by LPS or TNF-α can be reversed by NOS inhibitors and reinitiated by L-arginine (Kilbourn et. al., *PNAS,* 87, 3629–32, 1990). Conditions which lead to cytokine-induced hypotension include septic shock, hemodialysis (Beasley and Brenner, *Kidney Int.,* 42, Suppl., 38, S96–S100, 1992) and IL-2 therapy in cancer patients (Hibbs et. al., *J. Clin. Invest.,* 89, 867–77, 1992). NOS 2 is implicated in these responses, and thus the possibility exists that a NOS inhibitor would be effective in ameliorating cytokine-induced hypotension. Recent studies in animal models have suggested a role for NO in the pathogenesis of inflammation and pain and NOS inhibitors have been shown to have beneficial effects on some aspects of the inflammation and tissue changes seen in models of inflammatory bowel disease, (Miller et. al., *J. Pharmacol. Exp. Ther.*, 264, 11–16, 1990) and cerebral ischemia and arthritis (Ialenti et. al., *Br. J. Pharmacol.*, 110, 701–6, 1993; Stevanovic-Racic et al., *Arth. & Rheum.*, 37, 1062–9, 1994). Moreover transgenic mice deficient in NOS 1 show diminished cerebral ischemia (Huang et. al., *Science*, 265, 1883–5, 1994).

Further conditions where there is an advantage in inhibiting NO production from L-arginine include therapy with cytokines such as TNF, IL-1 and IL-2 or therapy with cytokine-inducing agents, for example 5,6-dimethylxanthenone acetic acid, and as an adjuvant to short term immunosuppression in transplant therapy. In addition, compounds which inhibit NO synthesis may be of use in reducing the NO concentration in patients suffering from inflammatory conditions in which an excess of NO contributes to the pathophysiology of the condition, for example adult respiratory distress syndrome (ARDS) and myocarditis.

There is also evidence that an NO synthase enzyme may be involved in the degeneration of cartilage which takes place in autoimmune and/or inflammatory conditions such as arthritis, rheumatoid arthritis, chronic bowel disease and systemic lupus erythematosis (SLE). It is also thought that an NO synthase enzyme may be involved in insulin-dependent diabetes mellitus. Therefore, a yet further aspect of the present invention provides cyclic amidine derivatives or salts thereof in the manufacture of a medicament for use in cytokine or cytokine-inducing therapy, as an adjuvant to short term immunosuppression in transplant therapy, for the treatment of patients suffering from inflammatory conditions in which an excess of NO contributes to the pathophysiology of the condition.

SUMMARY OF THE INVENTION

The invention disclosed herein encompasses compounds of Formula I

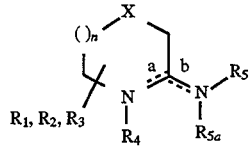

and pharmaceutically acceptable salts thereof which have been found useful in the treatment of nitric oxide synthase mediated diseases and disorders, including neurodegenerative disorders, disorders of gastrointestinal motility and inflammation. These diseases and disorders include hypotension, septic shock, toxic shock syndrome, hemodialysis related conditions, tuberculosis, cancer, IL-2 therapy such as in cancer patients, cachexia, immunosuppression such as in transplant therapy, autoimmune and/or inflammatory indications including sunburn, eczema or psoriasis and respiratory conditions such as bronchitis, asthma, oxidant-induced lung injury and acute respiratory distress (ARDS), glomerulonephritis, restenosis, inflammatory sequelae of viral infections, myocarditis, heart failure, atherosclerosis, osteoarthritis, rheumatoid arthritis, septic arthritis, chronic or inflammatory bowel disease, ulcerative colitis, Crohn's disease, systemic lupus erythematosis (SLE), ocular conditions such as ocular hypertension, retinitis and uveitis, type 1 diabetes, insulin-dependent diabetes mellitus and cystic fibrosis. Compounds of Formula I are also usful in the treatment of hypoxia, hyperbaric oxygen convulsions and toxicity, dementia, Alzheimer's disease, Sydenham's chorea, Parkinson's disease, Huntington's disease, amyotrophic lateral sclerosis (ALS), multiple sclerosis, epilepsy, Korsakoff's disease, imbecility related to cerebral vessel disorder, NO mediated cerebral trauma and related sequelae, ischemic brain edema (stroke), sleeping disorders, eating disorders such as anorexia, schizophrenia, depression, pre-menstrual syndrome (PMS), urinary incontinence, anxiety, drug and alcohol addiction, pain, migraine, emesis, immune complex disease, as immunosupressive agents, acute allograft rejection, infections caused by invasive microorganisms which produce NO and for preventing or reversing tolerance to opiates and diazepines.

DETAILED DESCRIPTION OF THE INVENTION

The invention disclosed herein encompasses compounds of Formula I

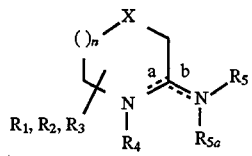

and pharmaceutically acceptable salts thereof wherein
side a or side b has a double bond,
n is 0, 1, 2, 3 or 4
X is selected from $CH_2$, O, S and NH,
$R_1$, $R_2$ and $R_3$ are each independently selected from the group consisting of
(a) hydrogen,
(b) $C_{1-12}$alkoxy,
(c) $C_{1-12}$alkylS(O)$_k$ wherein k is 0, 1 or 2,
(d) mono $C_{1-12}$alkylamino,
(e) (di-$C_{1-12}$alkyl)amino,
(f) $C_{1-12}$alkylcarbonyl,
(g) $C_{1-12}$alkyl,
(h) $C_{2-12}$alkenyl,
(i) $C_{2-12}$alkynyl,
(j) $C_{5-10}$cycloalkyl,
(k) hetero $C_{5-10}$cycloalkyl, wherein the hetero $C_{5-10}$cycloalkyl optionally contains 1 or 2 heteroatoms selected from S, O and N,
(l) aryl, selected from phenyl or naphthyl,
(m) heteroaryl, wherein heteroaryl is selected from the group consisting of:
(1) benzimidazolyl,
(2) benzofuranyl,
(3) benzooxazolyl,
(4) furanyl,
(5) imidazolyl,
(6) indolyl,
(7) isooxazolyl,
(8) isothiazolyl,
(9) oxadiazolyl,
(10) oxazolyl,
(11) pyrazinyl,
(12) pyrazolyl,
(13) pyridyl,
(14) pyrimidyl,
(15) pyrrolyl,
(17) isoquinolyl,
(18) tetrazolyl,
(19) thiadiazolyl,
(20) thiazolyl,

(21) thienyl, and
(22) triazolyl,
(n) amino,
(o) oxo,
(p) C(O)OH,
(q) C(O)OR$_6$, R$_6$ is selected from hydrogen, phenyl, cyclohexyl or C$_{1-6}$alkyl, each of (b) to (m) being optionally mono or di-substituted the substituents being independently selected from
(1) hydroxy,
(2) carboxy,
(3) —NR$_6$R$_7$, where R$_7$ is selected from hydrogen, phenyl, cyclohexyl or C$_{1-6}$alkyl,
(4) —OR$_6$,
(5) —C(O)OR$_6$,
(6) —S(O)$_k$R$_6$,
(7) halo selected from F, Cl, Br and I,
(8) —C(=NR$_6$)—NHR$_7$,
(9) —S—C(=NR$_6$)—NHR$_7$, or when two members of the group R$_1$, R$_2$ and R$_3$ reside on the same atom of Formula I, or two of the group R$_1$, R$_2$ and R$_3$ reside on adjacent atoms of Formula I, said two members may optionally be joined, such that together with the atoms to which they are attached there is formed a saturated or unsaturated monocyclic ring of 5, 6 or 7 atoms, said monocyclic ring optionally containing up to three hetero atoms selected from N, O or S, or when a member of the group R$_1$, R$_2$ and R$_3$ resides on an atom adjacent to the N on which R$_4$ resides, said member may optionally be joined with R$_4$, such that together with the N on which R$_4$ resides and the carbon on which said member resides there is formed a saturated or unsaturated monocyclic heterocycle of 5, 6 or 7 atoms, said monocycle optionally containing up to three hetero atoms selected from N, O or S, R$_4$, R$_5$ and R$_{5a}$ are each independently selected from the group consisting of
(a) hydrogen,
(b) linear and branched C$_{1-12}$alkyl, optionally mono or di-substituted, the substituents being independently selected from
(1) hydroxy,
(2) carboxy,
(3) —NR$_6$R$_7$,
(4) —OR$_6$,
(5) —C(O)OR$_6$,
(6) —S(O)$_k$R$_6$,
(7) halo selected from F, Cl, Br and I,
(8) phenyl, optionally mono or di-substituted with hydroxy, halo, C$_{1-4}$alkyl, or C$_{1-4}$alkoxy,
(c) —C(O)NR$_8$R$_9$, where R$_8$ and R$_9$ are each independently hydrogen, phenyl, cyclohexyl or C$_{1-6}$alkyl, said C$_{1-6}$alkyl optionally substituted by
(1) hydroxy,
(2) amino,
(3) carboxy,
(4) —NR$_{10}$R$_{11}$, wherein R$_{10}$ and R$_{11}$ are each independently H, C$_{1-6}$alkyl, phenyl or benzyl,
(5) —OR$_{10}$,
(6) —C(O)OR$_{10}$,
(7) —S(O)$_m$R$_{10}$, where m is 0, 1 or 2,
(8) halo selected from F, Cl, Br and I,
(9) optionally substituted aryl wherein aryl and aryl substituents are as defined above,
(10) optionally substituted heteroaryl wherein heteroaryl and heteroaryl substituents are as defined above,
(11) optionally substituted C$_{5-10}$cycloalkyl wherein cycloalkyl and cycloalkyl substituents are as defined above,
(12) optionally substituted hetero C$_{5-10}$cycloalkyl wherein hetero cycloalkyl and hetero cycloalkyl substituents are as defined above,
(d) —C(S)NR$_8$R$_9$,
(e) —C(O)R$_9$,
(f) —C(O)OR$_9$,
(g) —C(S)R$_9$,
(h) phenyl,
(i) cyclohexyl, provided that R$_4$ is present only when side a is a single bond and R5a is present only when side b is a single bond.

Within this embodiment is the genus wherein
n is 0, 1, 2, 3 or 4,
X is selected from CH$_2$, O, S and NH,
R$_1$, R$_2$ and R$_3$ are each independently selected from the group consisting of
(a) hydrogen,
(b) C$_{1-6}$alkoxy,
(c) C$_{1-6}$alkylamino,
(d) C$_{1-6}$alkylcarbonyl,
(e) C$_{1-6}$alkyl,
(f) C$_{2-6}$alkenyl,
(g) C$_5$, C$_6$ or C$_7$cycloalkyl,
(h) hetero C$_5$ or C$_6$ cycloalkyl, wherein the hetero C$_5$ or C$_6$ cycloalkyl optionally contains 1 heteroatom selected from S, O and N,
(i) aryl, selected from phenyl or naphthyl,
(j) heteroaryl, wherein heteroaryl is selected from the group consisting of:
(1) furanyl,
(2) pyrazinyl,
(3) pyrazolyl,
(4) pyridyl,
(5) pyrimidyl,
(6) thiazolyl,
(7) thienyl, and
(8) triazolyl, each of (b) to (j) being optionally mono or di-substituted the substituents being independently selected from
(1) hydroxy,
(2) carboxy,
(3) —NR$_6$R$_7$, where R$_6$ and R$_7$ are each independently hydrogen, phenyl or C$_{1-4}$alkyl,
(4) —OR$_6$,
(5) —C(O)OR$_6$,
(6) —S(O)$_k$R$_6$, where k is 0, 1 or 2,
(7) halo selected from F, Cl, Br and I, or when two members of the group R$_1$, R$_2$ and R$_3$ reside on the same atom of Formula I, or two of the group R$_1$, R$_2$ and R$_3$ reside on adjacent atoms of Formula I, said two members may optionally be joined, such that together with the atoms to which they are attached there is formed a saturated or unsaturated monocyclic ring of 5, 6 or 7 atoms, said monocyclic ring optionally containing up to three hetero atoms selected from N, O or S, or when a member of the group R$_1$, R$_2$ and R$_3$ resides on an atom adjacent to the N on which R$_4$ resides, said member may optionally be joined with R$_4$, such that together with the N on which R$_4$ resides and the carbon on which said member resides there is formed a saturated or unsaturated monocyclic heterocycle of 5, 6 or 7 atoms, said monocycle optionally containing up to three hetero atoms selected from N, O or S, $R_4$, $R_5$ and $R_{5a}$ are each independently selected from the group consisting of
  (a) hydrogen,
  (b) linear and branched $C_{1-6}$alkyl, optionally mono or di-substituted, the substituents being independently selected from
    (1) hydroxy,
    (2) carboxy,
    (3) —$NR_6R_7$,
    (4) —$OR_6$,
    (5) —$C(O)OR_6$,
    (6) —$S(O)_kR_6$, where k is 0, 1 or 2,
    (7) halo selected from F, Cl, Br and I,
  (c) —$C(O)NR_8R_9$, where $R_8$ and $R_9$ are each independently hydrogen, phenyl, cyclohexyl or $C_{1-4}$alkyl, said $C_{1-4}$alkyl optionally substituted by
    (1) hydroxy,
    (2) amino,
    (3) carboxy,
    (4) —$NR_{10}R_{11}$, wherein $R_{10}$ and $R_{11}$ are each independently H, $C_{1-4}$alkyl, phenyl or benzyl,
    (5) —$OR_{10}$,
    (6) —$C(O)OR_{10}$,
    (7) —$S(O)_mR_{10}$, where m is 0, 1 or 2,
    (8) halo selected from F, Cl, Br and I,
    (9 optionally substituted aryl wherein the aryl and substituents are as defined above,
    (10) optionally substituted heteroaryl wherein the heteroaryl and substituents are as defined above,
    (11) optionally substituted $C_5$ or $C_6$ cycloalkyl wherein the cycloalkyl and substituents are as defined above,
    (12) optionally substituted hetero $C_5$ or $C_6$ cycloalkyl wherein the hetero cycloalkyl and substituents are as defined above,
  (d) —$C(S)NR_8R_9$,
  (e) —$C(O)R_9$,
  (f) —$C(O)OR_9$,
  (g) —$C(S)R_9$,
  (h) phenyl,
  (i) cyclohexyl, such that $R_4$ is present only when side a is a single bond and side b is a double bond.

Within this genus is the class of compounds of the formulae

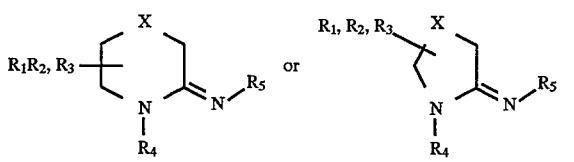

wherein
X is selected from $CH_2$, S and NH,
$R_1$, $R_2$ and $R_3$ are each independently selected from the group consisting of
  (a) hydrogen,
  (b) linear and branched $C_{1-4}$alkyl, said $C_{1-4}$alkyl being optionally mono or di-substituted the substituents being independently selected from
    (1) carboxy,
    (2) —$NR_6R_7$, wherein $R_6$ and $R_7$ are each independently hydrogen or $C_{1-3}$ alkyl,
    (3) —$OR_6$,
    (4) —$C(O)OR_6$,
    (5) —$S(O)_kR_6$, where k is 0, 1 or 2, $R_4$ is selected from the group consisting of
  (a) hydrogen,
  (b) —$C(O)NHR_9$, where $R_9$ is hydrogen or $C_{1-4}$alkyl, said $C_{1-4}$alkyl optionally substituted by
    (1) hydroxy,
    (2) amino,
    (3) carboxy,
    (4) —$NR_{10}R_{11}$, wherein $R_{10}$ and $R_{11}$ are each independently $C_{1-3}$alkyl,
    (5) —$OR_{10}$,
    (6) —$C(O)OR_{10}$,
    (7) —$S(O)_mR_{10}$, where m is 1 or 2,
    (8) halo selected from F, Cl, Br and I,
  (c) —$C(S)NHR_9$;
  (d) $C_{1-3}$alkyl;

$R_5$ is selected from the group consisting of
  (a) hydrogen,
  (b) —$C(O)NHR_9$,
  (c) —$C(S)NR_8R_9$,
  (d) $C_{1-3}$alkyl.

As appreciated by those of skill in the art the additional carbon members of the Formula I ring, "$( )_n$" and definitions "$CH_2$" and "NH" under X, provide available positions for the substituents $R_1$, $R_2$ or $R_3$.

When any variable (e.g. $R_1$, $R_2$, $R_3$, $R_4$, $R_5$, $R_6$, $R_7$, $R_8$, Ra, k, n, p etc.) occurs in any position of a compound of Formula I, its definition on each occurrence is independent of its definition at every other occurrence.

Accordingly, in one aspect the invention disclosed herein encompasses compounds of Formula I

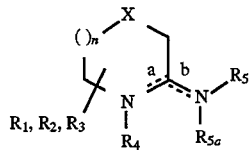

and pharmaceutically acceptable salts thereof wherein
side a or side b has a double bond,
n is 0, 1, 2, 3 or 4
X is selected from $CH_2$, $CR_{12}R_{13}$, O, $S(O)_m$, NH, and —$N(C_{1-6}alkyl)$—,
m is 0, 1 or 2,
$R_1$, $R_2$, $R_3$, $R_{12}$ and $R_{13}$ are each independently selected from the group consisting of
  (a) hydrogen,
  (b) $C_{1-12}$alkoxy,
  (c) $C_{1-12}$alkyl$S(O)_k$ wherein k is 0, 1 or 2,
  (d) mono $C_{1-12}$alkylamino,
  (e) (di-$C_{1-12}$ alkyl)amino,
  (f) $C_{1-12}$alkylcarbonyl,
  (g) $C_{1-12}$alkyl,
  (h) $C_{2-12}$alkenyl,
  (i) $C_{2-12}$alkynyl,
  (j) $C_{5-10}$cycloalkyl,
  (k) hetero $C_{5-10}$cycloalkyl, wherein the hetero $C_{5-10}$cycloalkyl optionally contains 1 or 2 heteroatoms selected from S, O and N,
  (l) aryl, selected from phenyl or naphthyl,
  (m) heteroaryl, wherein heteroaryl is selected from the group consisting of:
    (1) benzimidazolyl,
    (2) benzofuranyl,
    (3) benzooxazolyl, (4) furanyl,
(5) imidazolyl,
(6) indolyl,
(7) isooxazolyl,
(8) isothiazolyl,
(9) oxadiazolyl,
(10) oxazolyl,
(11) pyrazinyl,
(12) pyrazolyl,
(13) pyridyl,
(14) pyrimidyl,
(15) pyrrolyl,
(17) isoquinolyl,
(18) tetrazolyl,
(19) thiadiazolyl,
(20) thiazolyl,
(21) thienyl, and
(22) triazolyl,
(n) amino,
(o) oxo,
(p) C(O)OH,
(q) C(O)OR$_6$, R$_6$ is selected from hydrogen, phenyl, cyclohexyl or C$_{1-6}$alkyl, each of (b) to (m) being optionally mono or di-substituted the substituents being independently selected from
(1) hydroxy,
(2) carboxy,
(3) —NR$_6$R$_7$, where R$_7$ is selected from hydrogen, phenyl, cyclohexyl or C$_{1-6}$alkyl,
(4) —OR$_6$,
(5) —C(O)OR$_6$,
(6) —S(O)$_k$R$_6$,
(7) halo selected from F, Cl, Br and I,
(8) —C(=NR$_6$)—NHR$_7$,
(9) —S—C(=NR$_6$)—NHR$_7$, or when two members of the group R$_1$, R$_2$ and R$_3$ reside on the same carbon atom of Formula I, or two of the group R$_1$, R$_2$ and R$_3$ reside on adjacent atoms of Formula I, said two members may optionally be joined, such that together with the atom to which they are attached there is formed a saturated or unsaturated monocyclic ring of 5, 6 or 7 atoms, said monocyclic ring optionally containing up to three hetero atoms selected from N, O or S, or when a member of the group R$_1$, R$_2$ and R$_3$ resides on an atom adjacent to the N on which R$_4$ resides, said member may optionally be joined with R$_4$, such that together with the N on which R$_4$ resides and the carbon on which said member resides there is formed a saturated or unsaturated monocyclic heterocycle of 5, 6 or 7 atoms, said monocycle optionally containing up to three hetero atoms selected from N, O or S, with the proviso that one of R$_{12}$ and R$_{13}$ is other than hydrogen, R$_4$, R$_5$ and R$_{5a}$ are each independently selected from the group consisting of
(a) hydrogen,
(b) linear and branched C$_{1-12}$alkyl, optionally mono or di-substituted, the substituents being independently selected from
(1) hydroxy,
(2) carboxy,
(3) —NR$_6$R$_7$,
(4) —OR$_6$,
(5) —C(O)OR$_6$,
(6) —S(O)$_k$R$_6$,
(7) halo selected from F, Cl, Br and I,
(8) phenyl, optionally mono or di-substituted with hydroxy, halo, C$_{1-4}$alkyl, or C$_{1-4}$alkoxy,
(c) —C(O)NR$_8$R$_9$, where R$_8$ and R$_9$ are each independently hydrogen, phenyl, cyclohexyl or C$_{1-6}$alkyl, said C$_{1-6}$alkyl optionally substituted by
(1) hydroxy,
(2) amino,
(3) carboxy,
(4) —NR$_{10}$R$_{11}$, wherein R$_{10}$ and R$_{11}$ are each independently H, C$_{1-6}$alkyl, phenyl or benzyl,
(5) —OR$_{10}$,
(6) —C(O)OR$_{10}$,
(7) —S(O)$_m$R$_{10}$, where m is 0, 1 or 2,
(8) halo selected from F, Cl, Br and I,
(9) optionally substituted aryl wherein aryl and aryl substituents are as defined above,
(10) optionally substituted heteroaryl wherein heteroaryl and heteroaryl substituents are as defined above,
(11) optionally substituted C$_{5-10}$cycloalkyl wherein cycloalkyl and cycloalkyl substituents are as defined above,
(12) optionally substituted hetero C$_{5-10}$cycloalkyl wherein hetero cycloalkyl and hetero cycloalkyl substituents are as defined above,
(d) —C(S)NR$_8$R$_9$,
(e) —COR$_9$,
(f) —C(O)OR$_9$,
(g) —C(S)R$_9$,
(h) phenyl,
(i) cyclohexyl, provided that R$_4$ is present only when side a is a single bond and R5a is present only when side b is a single bond.

Within this embodiment is the genus wherein
m is 0, 1 or 2,
n is 0, 1, 2, 3 or 4,
X is selected from CH$_2$, CR$_{12}$R$_{13}$, O, S(O)$_m$NH, and —N(C$_{1-6}$alkyl)—,
R$_1$, R$_2$, R$_3$, R$_{12}$ and R$_{13}$ are each independently selected from the group consisting of
(a) hydrogen,
(b) C$_{1-6}$alkoxy,
(c) C$_{1-6}$alkylamino,
(d) C$_{1-6}$alkylcarbonyl,
(e) C$_{1-6}$alkyl,
(f) C$_{2-6}$alkenyl,
(g) C$_5$, C$_6$ or C$_7$cycloalkyl,
(h) hetero C$_5$ or C$_6$ cycloalkyl, wherein the hetero C$_5$ or C$_6$ cycloalkyl optionally contains 1 heteroatom selected from S, O and N,
(i) aryl, selected from phenyl or naphthyl,
(j) heteroaryl, wherein heteroaryl is selected from the group consisting of:
(1) furanyl,
(2) pyrazinyl,
(3) pyrazolyl,
(4) pyridyl,
(5) pyrimidyl,
(6) thiazolyl,
(7) thienyl, and
(8) triazolyl, each of (b) to (j) being optionally mono or di-substituted the substituents being independently selected from
(1) hydroxy,
(2) carboxy,
(3) —NR$_6$R$_7$, where R$_6$ and R$_7$ are each independently hydrogen, phenyl or C$_{1-4}$alkyl, (4) —OR$_6$,
(5) —C(O)OR$_6$,
(6) —S(O)$_k$R$_6$, where k is 0, 1 or 2,
(7) halo selected from F, Cl, Br and I, or when two members of the group R$_1$, R$_2$ and R$_3$ reside on the same atom of Formula I, or two of the group R$_1$, R$_2$ and R$_3$ reside on adjacent atoms of Formula I, said two members may optionally be joined, such that together with the atoms to which they are attached there is formed a saturated or unsaturated monocyclic ring of 5, 6 or 7 atoms, said monocyclic ring optionally containing up to three hetero atoms selected from N, O or S, or when a member of the group R$_1$, R$_2$ and R$_3$ resides on an atom adjacent to the N on which R$_4$ resides, said member may optionally be joined with R$_4$, such that together with the N on which R$_4$ resides and the carbon on which said member resides there is formed a saturated or unsaturated monocyclic heterocycle of 5, 6 or 7 atoms, said monocycle optionally containing up to three hetero atoms selected from N, O or S, R$_4$, R$_5$ and R$_{5a}$ are each independently selected from the group consisting of
(a) hydrogen,
(b) linear and branched C$_{1-6}$alkyl, optionally mono or di-substituted, the substituents being independently selected from
(1) hydroxy,
(2) carboxy,
(3) —NR$_6$R$_7$,
(4) —OR$_6$,
(5) —C(O)OR$_6$,
(6) —S(O)$_k$R$_6$, where k is 0, 1 or 2,
(7) halo selected from F, Cl, Br and I,
(c) —C(O)NR$_8$R$_9$, where R$_8$ and R$_9$ are each independently hydrogen, phenyl, cyclohexyl or C$_{1-4}$alkyl, said C$_{1-4}$alkyl optionally substituted by
(1) hydroxy,
(2) amino,
(3) carboxy,
(4) —NR$_{10}$R$_{11}$, wherein R$_{10}$ and R$_{11}$ are each independently H, C$_{1-4}$alkyl, phenyl or benzyl,
(5) —OR$_{10}$,
(6) —C(O)OR$_{10}$,
(7) —S(O)$_m$R$_{10}$, where m is 0, 1 or 2,
(8) halo selected from F, Cl, Br and I,
(9) optionally substituted aryl wherein the aryl and substituents are as defined above,
(10) optionally substituted heteroaryl wherein the heteroaryl and substituents are as defined above,
(11) optionally substituted C$_5$ or C$_6$ cycloalkyl wherein the cycloalkyl and substituents are as defined above,
(12) optionally substituted hetero C$_5$ or C$_6$ cycloalkyl wherein the hetero cycloalkyl and substituents are as defined above,
(d) —C(S)NR$_8$R$_9$,
(e) —COR$_9$,
(f) —C(O)OR$_9$,
(g) —C(S)R$_9$,
(h) phenyl,
(i) cyclohexyl,
such that R$_4$ is present only when side a is a single bond and side b is a double bond.

Within this genus is the class of compounds of the formulae

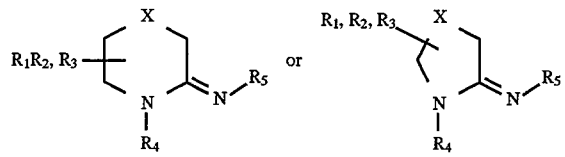

wherein
X is selected from CR$_{12}$R$_{13}$, S(O)$_m$ and —N(C$_{1-4}$alkyl)—,

R$_1$, R$_2$, R$_3$, R$_{12}$ and R$_{13}$ are each selected from the group consisting of
(a) hydrogen,
(b) hydroxy,
(c) linear and branched C$_{1-4}$alkyl or linear and branched C$_{1-4}$alkoxy, wherein said C$_{1-4}$alkyl or C$_{1-4}$alkoxy is optionally mono or di-substituted the substituents being independently selected from
(1) carboxy,
(2) —NR$_6$R$_7$, wherein R$_6$ and R$_7$ are each independently hydrogen or C$_{1-3}$alkyl,
(3) —OR$_6$,
(4) —C(O)OR$_6$,
(5) —S(O)$_k$R$_6$, where k is 0, 1 or 2,
with the proviso that one of R$_{12}$ and R$_{13}$ is other than hydrogen,
R$_4$ is selected from the group consisting of
(a) hydrogen,
(b) —C(O)NHR$_9$, where R$_9$ is hydrogen or C$_{1-4}$alkyl, said C$_{1-4}$alkyl optionally substituted by
(1) hydroxy,
(2) amino,
(3) carboxy,
(4) —NR$_{10}$R$_{11}$, wherein R$_{10}$ and R$_{11}$ are each independently C$_{1-3}$alkyl,
(5) —OR$_{10}$,
(6) —C(O)OR$_{10}$,
(7) —S(O)$_m$R$_{10}$, where m is 1 or 2,
(8) halo selected from F, Cl, Br and I,
(c) —C(S)NHR$_9$;
(d) C$_{1-3}$alkyl;
R$_5$ is selected from the group consisting of
(a) hydrogen,
(b) —C(O)NHR$_9$,
(c) —C(S)NR$_8$R$_9$,
(d) C$_{1-3}$alkyl.

In an alternative embodiment the invention is directed to compounds of the formulae

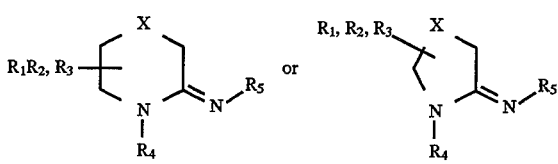

wherein
X is —N(C$_{1-3}$alkyl)—,
R$_1$, R$_2$ and R$_3$ are each independently selected from the group consisting of
(a) hydrogen,
(b) linear and branched C$_{1-4}$alkyl, said C$_{1-4}$alkyl being optionally mono or di-substituted the substituents being independently selected from
(1) carboxy,
(2) —NHR$_7$, wherein R$_6$ and R$_7$ are each independently hydrogen or C$_{1-3}$alkyl, (3) —C(O)OR$_6$, and (4) —S(O)$_k$R$_6$, where k is 1 or 2, (c) hydroxy, R$_4$ is selected from the group consisting of
(a) hydrogen,
(b) C$_{1-3}$alkyl;

R$_5$ is selected from the group consisting of
(a) hydrogen,
(b) —C(O)NHR$_9$, where R$_9$ is hydrogen or C$_{1-4}$alkyl, said C$_{1-4}$alkyl optionally substituted by
(1) hydroxy,
(2) amino,
(3) carboxy,
(4) —NR$_{10}$R$_{11}$, wherein R$_{10}$ and R$_{11}$ are each independently C$_{1-3}$alkyl,
(5) —OR$_{10}$,
(6) —C(O)OR$_{10}$,
(7) —SR$_{10}$, and
(8) —S(O)$_m$R$_{10}$, where m is 1 or 2,
(9) halo selected from F, Cl, Br and I,
(c) —C(S)NR$_8$R$_9$.
(d) C$_{1-3}$alkyl;

Within this embodiment is the genus of compound of the formulae

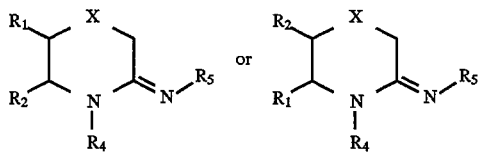

wherein

X is —N(C$_{1-3}$alkyl)—,

R$_1$ and R$_2$ are each selected from hydrogen or linear and branched C$_{1-4}$alkyl, said C$_{1-4}$alkyl being optionally mono or di-substituted the substituents being independently selected from
(1) carboxy,
(2) —NHR$_7$, wherein R$_6$ and R$_7$ are each independently hydrogen or C$_{1-3}$alkyl,
(3) —C(O)OR$_6$, and
(4) —S(O)$_k$R$_6$, where k is 1 or 2, R$_4$ is selected from the group consisting of
(a) hydrogen,
(b) C$_{1-3}$alkyl;

R$_5$ is selected from the group consisting of
(a) hydrogen,
(b) —C(O)NHR$_9$, where R$_9$ is hydrogen or C$_{1-4}$alkyl, said C$_{1-4}$alkyl optionally substituted by
(1) hydroxy,
(2) amino,
(3) carboxy,
(4) —NR$_{10}$R$_{11}$, wherein R$_{10}$ and R$_{11}$ are each independently C$_{1-3}$alkyl,
(5) —OR$_{10}$,
(6) —C(O)OR$_{10}$,
(7) —SR$_{10}$, and
(8) —S(O)$_m$R$_{10}$, where m is 1 or 2,
(9) halo selected from F, Cl, Br and I,
(c) —CSNR$_8$R$_9$.
(d) C$_{1-3}$alkyl.

Within this genus are the compounds of the formulae

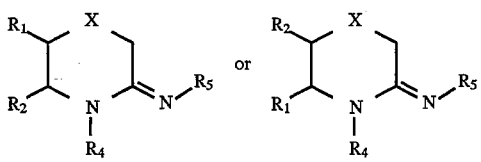

wherein

X is —N(C$_{1-3}$alkyl)—,

R$_1$ is selected from the group consisting of hydrogen, hydroxy or linear and branched C$_{1-4}$alkyl, said C$_{1-4}$alkyl being optionally mono or di-substituted the substituents being independently selected from
(1) carboxy,
(2) —NHR$_7$, wherein R$_6$ and R$_7$ are each independently hydrogen or C$_{1-3}$alkyl,
(3) —C(O)OR$_6$, and
(4) —S(O)$_k$R$_6$, where k is 1 or 2, R$_2$ is linear and branched C$_{1-4}$alkyl, R$_4$ is selected from the group consisting of
(a) hydrogen,
(b) C$_{1-3}$alkyl;

R$_5$ is selected from the group consisting of
(a) hydrogen,
(b) —C(O)NHR$_9$, where R$_9$ is hydrogen or C$_{1-4}$alkyl, said C$_{1-4}$alkyl optionally substituted by
(1) hydroxy,
(2) amino,
(3) carboxy,
(4) —NR$_{10}$R$_{11}$, wherein R$_{10}$ and R$_{11}$ are each independently C$_{1-3}$alkyl,
(5) —OR$_{10}$,
(6) —C(O)OR$_{10}$,
(7) —SR$_{10}$, and
(8) —S(O)$_m$R$_{10}$, where m is 1 or 2,
(9) halo selected from F, Cl, Br and I,
(c) —CSNR$_8$R$_9$.
(d) C$_{1-3}$alkyl.

Exemplifying the invention are the compounds of Examples 1 through 25.

As appreciated by those of skill in the art, compounds of Formula I include those wherein there is a double bond at side a or b such as those shown in Formula Ia or Ib or tautomeric forms thereof:

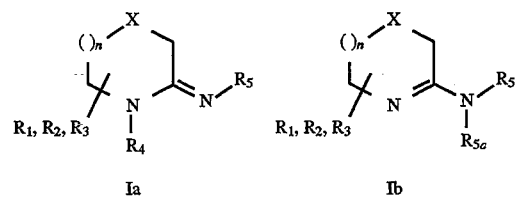

Ia  Ib

As also appreciated by those of skill in the art, compounds of Formula 1 wherein or when two members of the group R$_1$, R$_2$ and R$_3$ are joined together to form a ring are intended to include such formulae as:

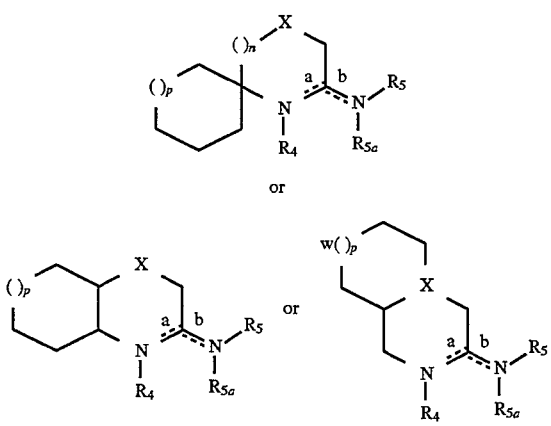

wherein p is 0, 1, or 2 and wherein the second ring may contain up to three hetero atoms selected from N, O or S.

Similarly, compounds of Formula I wherein a member of the group $R_1$, $R_2$ and $R_3$ resides on an atom adjacent to the N on which $R_4$ resides and forms a ring therewith may be illustrated by:

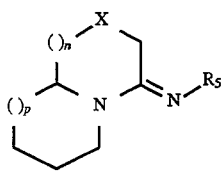

wherein p is 0, 1, or 2 and wherein the second ring may contain up to three hetero atoms selected from N, O or S For purposes of this specification alkyl is defined to include linear, branched, and cyclic structures, with $C_{1-6}$alkyl including methyl, ethyl, propyl, 2-propyl, s- and t-butyl, butyl, pentyl, hexyl, cyclopropyl, cyclobutyl, cyclopentyl and cyclohexyl. Similarly, $C_{1-6}$alkoxy is intended to include alkoxy groups of from 1 to 6 carbon atoms of a straight, branched, or cyclic configuration. Examples of lower alkoxy groups include methoxy, ethoxy, propoxy, isopropoxy, cyclopropyloxy, cyclohexyloxy, and the like. Likewise, $C_{1-6}$ alkylthio is intended to include alkylthio groups of from 1 to 6 carbon atoms of a straight, branched or cyclic configuration. Examples of lower alkylthio groups include methylthio, propylthio, isopropylthio, cycloheptylthio, etc. By way of illustration, the propylthio group signifies —$SCH_2CH_2CH_3$.

Heteroaryl includes, but is not limited to furan, thiophene, pyrrole, isoxazole, isothiazole, pyrazole, oxazole, thiazole, imidazole, 1,2,3-oxadiazole, 1,2,3-thiadiazole, 1,2,3-triazole, 1,3,4-oxadiazole, 1,3,4-thiadiazole, 1,3,4-triazole, 1,2,5-oxadiazole, 1,2,5-thiadiazole, pyridine, pyridazine, pyrimidine, pyrazine, 1,2,4-triazine, 1,3,5-triazine and 2,4,5-tetrazine.

As outlined in the summary of the invention, the compounds of the instant invention are useful for in the treatment of a number of NOS implicated diseases. The implication of these diseases is well documented in the literature. For example, with regard to psoriasis, see Ruzicka et. al., *J. Invest. Derm.*, 103: 397 (1994) or Kolb-Bachofen et. al., Lancet, 344: 139 (1994) or Bull, et al., *J. Invest. Derm.*, 103:435(1994); with regard to uveitis, see Mandia et. al., Invest Opthalmol., 35: 3673–89 (1994); with regard to type 1 diabetes, see Eisieik & Leijersfam, Diabetes & Metabolism, 20: 116–22 (1994) or Kroncke et. al., *BBRC*, 175: 752–8 (1991) or Welsh el. at., *Endocrinol.*, 129: 3167–73 (1991); with regard to septic shock, see Petros et. al., Lancet, 338: 1557–8 (1991), Thiemermann & Vane, Eur. J. Pharmacol., 211: 172–82 (1992), or Evans et. al., Infec. Imm., 60: 4133–9 (1992), or Schilling et. al., Intensive Care Med., 19: 227–231 (1993); with regards to pain, see Moore et. al., Brit. J. Pharmacol., 102: 198–202 (1991), or Moore et. al, Brit. J. Pharmacol., 108: 296–97 (1992) or Meller et. al., *Europ. J. Pharmacol.*, 214: 93–6 (1992) or Lee et. al., *NeuroReport*, 3: 841–4 (1992); with regard to migraine, see Olesen et. al., TIPS, 15: 149–153 (1994); with regard to rheumatoid arthritis, see Kaurs & Halliwell, FEBS Letters, 350: 9–12 (1994); with regard to osteoarthritis, see Stadler et. al., *J. Immunol.*, 147: 3915–20 (1991); with regard to inflammatory bowel disease, see Miller et. al., Lancet, 34: 465–66 (1993) or Miller et. al., J. Pharmacol. Exp. Ther., 264: 11–16 (1993); with regard to asthma, see Hamid et. al., Lancet, 342: 1510–13 (1993) or Kharitonov, et. al., Lancet, 343: 133–5 (1994); with regard to Immune complex diseases, see Mulligan et. al., Br. J. Pharmacol., 107: 1159–62 (1992); with regard to multiple sclerosis, see Koprowski et. al., *PNAS*, 90: 3024–7 (1993); with regard to ischemic brain edema, see Nagafuji et. al., Neurosci., 147: 159–62 (1992) or Buisson et. al., Br. J. Pharmacol., 106: 766–67 (1992) or Trifiletti et. al., *Europ. J. Pharmacol.*, 218: 197–8 (1992); with regard to toxic shock syndrome, see Zembowicz & Vane, PNAS, 89: 2051–55 (1992); with regard to heart failure, see Winlaw et. al., Lancet, 344: 373–4 (1994); with regard to ulcerative colitis, see Boughton-Smith et. al., Lancet 342: 338–40 (1993); and with regard to atherosclerosis, see White et. al., PNAS, 91: 1044–8 (1994); with regard to glomerulonephritis, see Mühl et. al., *Br. J. Pharmcol.*, 112: 1–8 (1994); with regard to Paget's disease and osteoporosis, see Löwick et. al., *J. Clin. Invest.*, 93: 1465–72 (1994); with regard to inflammatory sequelae of viral infections, see Koprowski et. al., *PNAS*, 90: 3024–7 (1993); with regard to retinitis, see Goureau et. al., *BBRC*, 186: 854–9 (1992); with regard to oxidant induced lung injury, see Berisha et. al., *PNAS*, 91: 744–9 (1994); with regard to eczema, see Ruzica, et al., *J. Invest. Derm.*, 103:395(1994); with regard to acute allograft rejection, see Devlin, J. et al., *Transplantation*, 58:592–595 (1994); and with regard to infection caused by invasive microorganisms which produce NO, see Chen, Y and Rosazza, J. P. N., *Biochem. Biophys. Res. Comm.*, 203:1251–1258(1994).

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic acids or bases including inorganic bases and organic bases. Salts derived from inorganic acids include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N_-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Assay Protocol for NOS activity

NOS activity is measured as the formation of L-[2,3,4,5-$^3$H]Citrulline from L-[2,3,4,5-$^3$H]Arginine. The incubation buffer (100 µL) contained; 100 mM TES, pH 7.5, 5 µM FAD, 5 µM FMN, 10 µM $BH_4$, 0.5 mM NADPH, 0.5 mM DTT, 0.5 mg/mL BSA, 2 mM CaCl2, 10 µg/mL calmodulin (bovine), 1 µM L-Arg, 0.2 µCi L-[2,3,4,5-$^3$H]Arg, and the inhibitor in aqueous DMSO (max. 5%). The reaction is initiated by addition of enzyme. Incubations are performed at room temperature for 30 minutes and stopped by the addition of an equal volume of quenching buffer consisting of 200 mM sodium citrate, pH 2.2, 0.02% sodium azide. Reaction products are separated by passing through a cation exchange resin and quantitated as cpm by scintillation counting. Percent inhibition is calculated relative to enzyme incubated without inhibitor according to: % inhibition=100× (cpm L-[2,3,4,5-$^3$H]Cit with inhibitor/cpm L-[2,3,4,5-$^3$H] Cit without inhibitor).

Illustrative of the utility of the compounds of Formula I is the ability of such compounds to inhibit NO synthase as shown in Tables 1–5 and as measured by the assay described above:

TABLE 1

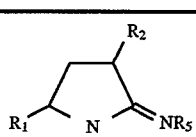

| $R_1$ | $R_2$ | $R_5$ | % inhibition (50 uM) |
|---|---|---|---|
| H | H | H | 90 |
| —$CH_3$ | H | H | 98 |
| H | —$CH_3$ | H | 97 |

TABLE 2

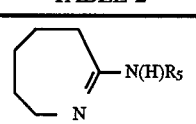

| $R_5$ | % inhibition (50 uM) |
|---|---|
| —$CH_3$ | 3 |
| —$CH_2CH_3$ | 55 |
| —$CH_2$-phenyl | 3 |
| -cyclohexyl | 8 |

TABLE 3

| Compound | % inhibition (50 uM) |
|---|---|
| (pyrrolidine-2-imine) | 90 |
| (piperidine-2-imine) | 100 |
| (azepane-2-imine) | 96 |
| (azocane-2-imine) | 100 |
| (azonane-2-imine) | 100 |

TABLE 4

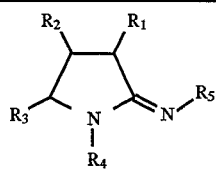

| R1 | R2 | R3 | R4 | R5 | iNOS | ecNOS | ncNOS |
|---|---|---|---|---|---|---|---|
| H | H | H | H | H | ≦10 | ≦10 | ≦10 |
| H | H | CO2H | H | 2-thiazolidinyl | ≦50 | NT | NT |
| H | H | H | H | C2H4Ph-3,4-(OH)2 | >50 | >50 | >50 |
| H | H | CH3 | H | H | ≦10 | ≦10 | ≦10 |
| CH3 | H | H | H | H | ≦10 | ≦10 | ≦1 |
| H | H | —(CH2)3— | | H | >50 | ≦50 | ≦10 |
| H | CH3 | H | H | H | ≦10 | ≦10 | ≦1 |
| H | CH3 | CH3 | H | H | ≦1 | ≦I | ≦I |
| CH3 | CH3 | H | H | H | ≦10 | ≦10 | ≦1 |
| CH3 | C2H5 | H | H | H | ≦1 | >50 | ≦10 |
| H | CH3 | C2H5 | H | H | ≦1 | ≦1 | ≦1 |
| H | C2H5 | H | H | H | ≦1 | ≦50 | ≦10 |
| H | n-C3H7 | H | H | H | ≦50 | >50 | >50 |
| H | n-C3H7 | CH3 | H | H | ≦50 | >50 | ≦50 |
| H | n-C3H7 | C2H5 | H | H | ≦50 | >50 | ≦50 |
| H | H | (CH3)2 | H | H | ≦10 | ≦50 | ≦10 |
| H | i-C3H7 | H | H | H | ≦10 | >50 | ≦50 |
| H | H | C2H5 | H | H | ≦50 | ≦10 | ≦10 |
| H | CH3 | CH3(A)* | H | H | ≦1 | ≦1 | ≦1 |
| H | CH3 | CH3(B)* | H | H | ≦1 | ≦1 | ≦1 |
| H | CH3 | n-C3H7 | H | H | ≦10 | ≦50 | ≦10 |
| H | C2H5 | CH3 | H | H | ≦1 | ≦10 | ≦1 |
| H | H | (S)-CH2OAc | H | H | ≦50 | >50 | ≦10 |
| H | H | (S)-CH2OH | H | H | ≦10 | >50 | ≦50 |
| H | H | (R)-CH2OAc | H | H | >50 | >50 | >50 |
| H | H | (R)-CH2OH | H | H | ≦50 | ≦50 | ≦50 |
| —(CH2)3— | | H | H | H | ≦10 | ≦10 | ≦1 |
| —(CH2)4— | | H | H | H | ≦10 | ≦50 | ≦1 |
| H | H | C(=O)NH(CH2)2C(=NH)NH2 | H | H | ≦10 | >50 | <10 |
| SH | H | H | H | H | ≦50 | ≦50 | ≦1 |

*isomers A and B

TABLE 5

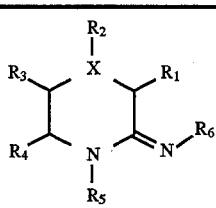

| X | R1 | R2 | R3 | R4 | R5 | R6 | iNOS | ecNOS | ncNOS |
|---|---|---|---|---|---|---|---|---|---|
| CH2 | H | H | H | H | H | H | ≦1 | ≦1 | ≦1 |
| CH2 | H | H | —(CH)4— | | H | H | ≦50 | >50 | ≦10 |
| CH2 | CH3 | H | H | H | H | H | ≦10 | ≦10 | ≦1 |
| CH2 | H | H | CH3 | H | H | H | ≦1 | ≦10 | ≦10 |
| CH | H | CH3 | H | H | H | H | ≦1 | ≦1 | ≦1 |
| CH | H | n-C3H7 | H | H | H | H | ≦10 | >50 | >50 |
| CH2 | CH3 | H | CH3 | H | H | H | ≦50 | ≦50 | ≦1 |
| CH2 | H | H | (CH3)2 | H | H | H | ≦10 | ≦50 | ≦10 |
| CH2 | H | H | (R)—CH3 | H | H | H | ≦1 | ≦10 | ≦10 |
| CH2 | H | H | (S)—CH3 | H | H | H | ≦10 | ≦10 | ≦10 |
| CH | H | (R)—CH3 | H | H | H | H | ≦1 | ≦1 | ≦1 |
| CH | H | (S)—CH3 | H | H | H | H | ≦1 | ≦1 | ≦1 |
| CH | H | CH3 | CH3 | H | H | H | ≦1 | ≦1 | ≦1 |
| C | | —(CH)4— | | H | H | H | ≦10 | ≦50 | ≦10 |
| N | H | H | —(CH2)4— | | H | H | ≦10 | >50 | ≦50 |

TABLE 5-continued

![Structure with R1, R2, R3, R4, R5, R6, X, N]

| X | R1 | R2 | R3 | R4 | R5 | R6 | iNOS | ecNOS | ncNOS |
|---|---|---|---|---|---|---|---|---|---|
| CH | H | CH3 | H | CH3 | H | H | ≦1 | ≦1 | ≦1 |
| S | H | — | H | H | H | H | ≦1 | ≦10 | ≦1 |
| CH2 | H | H | trans-(CH2)4— | | H | H | ≦1 | ≦10 | ≦1 |
| CH2 | H | H | cis-(CH2)4— | | H | H | ≦1 | ≦50 | ≦1 |
| N | H | H | cis-(CH2)4— | | H | H | ≦10 | >50 | >50 |
| CH2 | H | H | CF3 | H | H | H | ≦10 | >50 | >50 |
| CH | H | CH3 | cyclo-C6H12 | H | H | H | >50 | >50 | >50 |
| CH | C2H5 | CH3 | H | H | H | H | ≦50 | ≦50 | ≦10 |
| CH | CH3 | | —(CH2)3— | H | H | H | ≦10 | >50 | ≦10 |
| CH | H | CH3 | NHAc | H | H | H | ≦50 | >50 | >50 |
| CH | H | CH3 | CO2CH3 | H | H | H | ≦10 | >50 | ≦50 |
| CH2 | H | H | O-n-C3H7 | H | H | H | ≦1 | ≦10 | ≦10 |
| CH | n-C3H7 | CH3 | H | H | H | H | ≦50 | >50 | ≦50 |
| CH | H | CH3 | CH2NHAc | H | H | H | ≦50 | >50 | ≦50 |
| CH | H | CH3 | —(CH)4— | | H | H | ≦1 | ≦50 | ≦1 |
| N | H | CO2-t-C4H9 | H | H | H | H | ≦50 | >50 | >50 |
| N | H | H | H | H | H | H | ≦50 | >50 | ≦50 |
| CH | H | CH3 | CO2H | H | H | H | ≦10 | ≦50 | ≦10 |
| CH | H | (S)—CH3 | (S)—OH | H | H | H | ≦1 | ≦10 | ≦1 |
| CH | H | (S)—CH3 | (S)—OCH3 | H | H | H | ≦1 | ≦1 | ≦1 |

Several methods for preparing the compounds of this invention are illustrated in the following schemes and examples. Some of the compounds are known in the literature but none are reported to be inhibitors of NO Synthase. In one method outlined in scheme 1 and illustrated in Example 2, the compounds are prepared by reacting a cyclic iminoether with an appropriate amine or its salt such as a hydrochloride, hydrobromide, sulfate, alkyl sulfonate, acetate etc at a temperature between 0°–100° C. The required intermediate iminoether substrates can be prepared by O-alkylation of the corresponding lactam by reagents such as methyl trifluoromethanesulfonate, trimethyloxonium fluoborate, methyl sulfate etc. Other methods for preparation of iminoether known in the art of organic synthesis may also be employed. Many of the lactam starting materials are commercially available or they can be obtained by literature procedures. One useful method for the preparation of substituted lactams is illustrated in example 1.

-continued
SCHEME 1

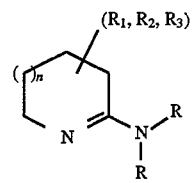

Another method for preparing compounds of this invention is shown in scheme 2. In this method a thiolactam is first reacted with an alkylating agent such as methyl iodide or methyl sulfate and the resulting iminothioether salt is reacted with an amine to furnish the desired amidines. The thiolactam substrates for this process are known in the literature or they can be prepared from the corresponding lactam by treatment with reagents such as $P_2S_5$ or Lawesson's reagent (2,4-bis(4-methoxyphenyl)-1,3-dithia-2,4-diphosphetane-2,4-disulfide) as illustrated in example 3.

SCHEME 1

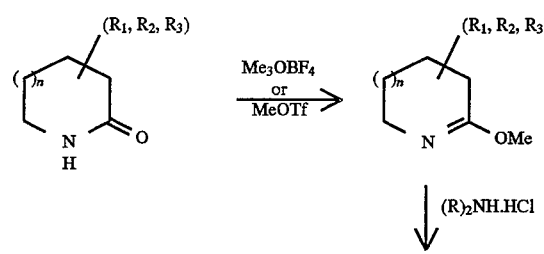

SCHEME 2

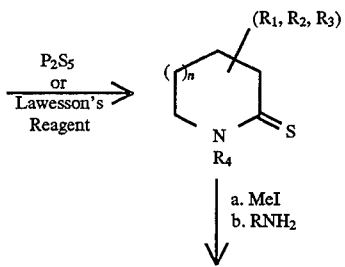

-continued
SCHEME 2

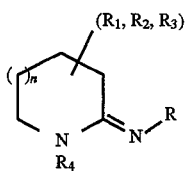

Alternatively, the cyclic amidine compounds may also be synthesized from acyclic precursors as described by Garigipati (*Tet. Lett.* 31, 1969–1972 (1990)). In this method (Scheme 3) an amino nitrile is converted to an aluminum amide by reaction with an alkylaluminum reagent such as trimethylaluminum and in situ cyclization of this intermediate furnishes the desired amidines.

2-aminopyridines by the method of Freifelder (M. Freifelder, R. W. Mattoon, Y. H. Ng, *J. Org. Chem.* 29, 3730–3732 (1964)) employing catalytic hydrogenation under acidic conditions (Scheme 4). The addition of acid during the hydrogenation is important (T. B. Grave, *J. Am. Chem. Soc.* 46, 1460–1470 (1924))

SCHEME 4

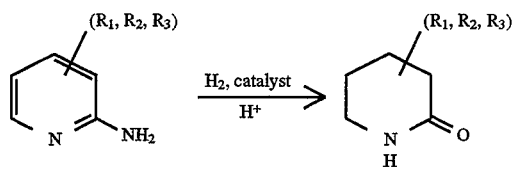

Cyclic amidines may also be prepared from acyclic precursors as shown in scheme 5 and demonstrated in example 6. Thus, a Michael addition of a nitroalkane to an acrylate ester by the method of Bunce and Drumright (*Org. Prod. Prep. Int.* 19, 471–475 (1987)) leads to an ester of 4-nitrobutyric acid. Reduction of the nitro group and cyclization gives a lactam which is converted to an amidine by the procedures described in scheme 1 or 2.

SCHEME 5

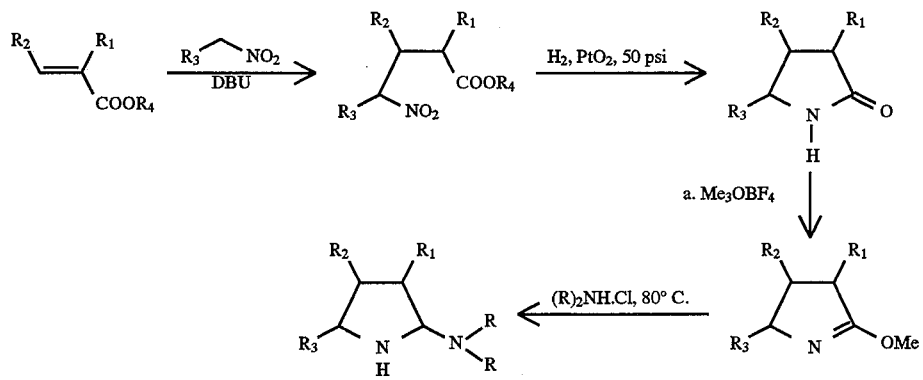

SCHEME 3

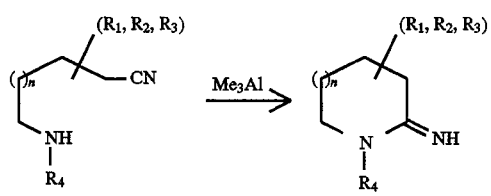

Alternatively, the cyclic amidine compounds may also be synthesized from substituted or unsubstituted Many cyclic amidines claimed in this specification can have stereoisomers and such individual stereoisomers may be prepared from chiral lactams. Numerous methods for the synthesis of stereochemically pure lactams have been described in literature. One such method using amino acids as starting materials is described by Reetz and Rohrig (*Angew. Chem. Int. Ed. Engl.* 28, 1706–1709 (1989)) and is shown in scheme 6. The key feature of this procedure is the stereospecific addition of organometallic reagents to an unsaturated ester and the reversal of the stereoselectivity with an unsaturated malonate, thus allowing synthesis of two diastereomers from the same aldehyde intermediate.

Scheme 6

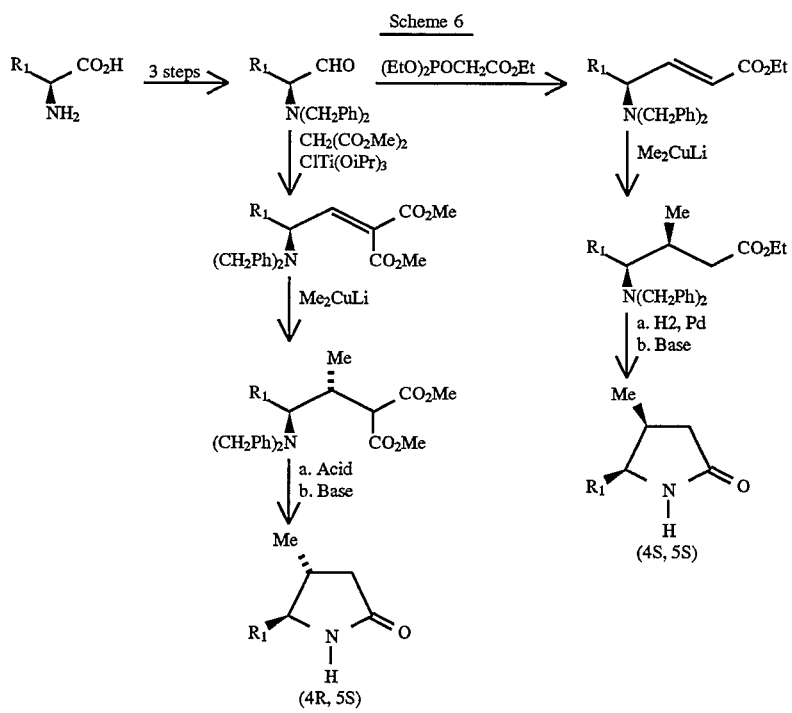

Synthetic methodology also exists for the preparation of chirally substituted 2-imino-piperidines. As shown in Scheme 7, addition of organocuprates to the O-tert-butyldimethylsilyl-protected (S)-(−)-5(hydroxymethyl)-2 (5H)-furanone B derived from A (available from Aldrich Chemical Co., Milwaukee, Wis.) will yield stereoisomer C (S. Hanessian and P. J. Murray, Tetrahedron, 43, 5055–5072 (1987)). Deprotection of C yields the free alcohol D which is converted to lactam F by described methodology (C. Herdeis and D. Waibel, Arch. Pharm. (Weinheim) 1991, 324, 269–274). Treatment with Meerwien's salt followed by reaction with ammonium chloride in refluxing ethanol yields chiral 2-imino-piperidines I and J. Other substituents and substitution patterns are available by analogous chemical manipulations from described intermediates (S. Hanessian, Aldrichimica Acta 22, 3–15 (1989)).

SCHEME 7

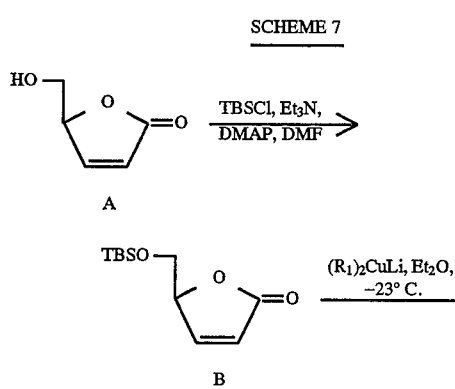

-continued
SCHEME 7

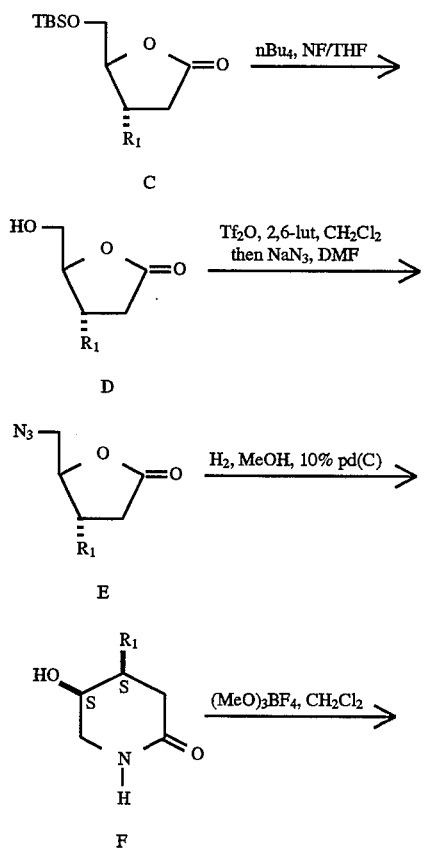

-continued
SCHEME 7

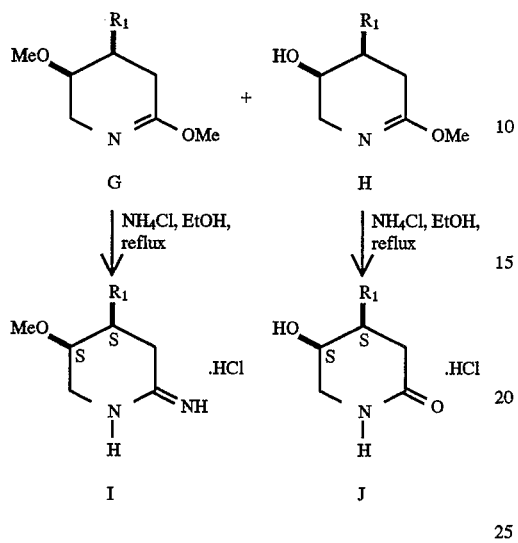

Another method for the synthesis of chiral amidines is shown scheme 8. This synthesis utilizes commercially available individual enantiomers of citronellic acid that allow preparation of chiral 2-iminopiperidines. Treatment of methyl citronellate with ozone and further oxidation of the intermediate gives an acid which was used in a Curtius reaction to furnish A upon reaction with benzyl alcohol. Hydrolysis, cyclization and removal of the Cbz group of A leads to a chiral lactam (B) and reaction of B with trimethyloxonium fluoroborate followed by NH$_4$Cl as detailed in scheme 1 furnishes a cyclic amidine. Citronellic acid is also a useful stagging material for chiral 5-methyl-2-iminopiperidines as shown in scheme 9. In this case citronellic acid is first subjected to the Curtius reaction to give a protected amine (C). Cleavage of the double bond of C by ozone and further oxidation directly leads to D and this lactam is converted to an enantiomerically pure amidine in 3 steps.

Scheme 8

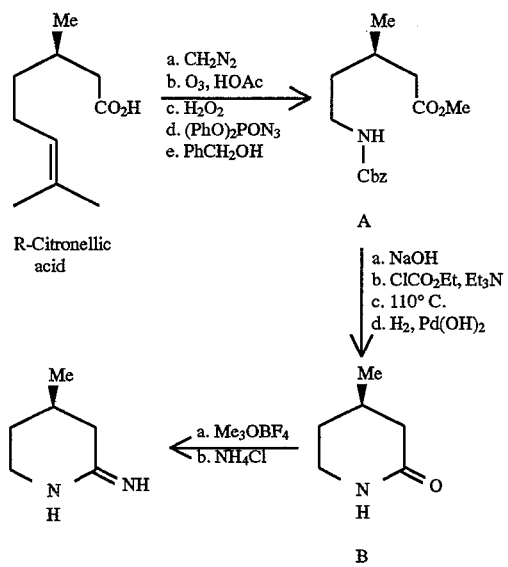

Scheme 9

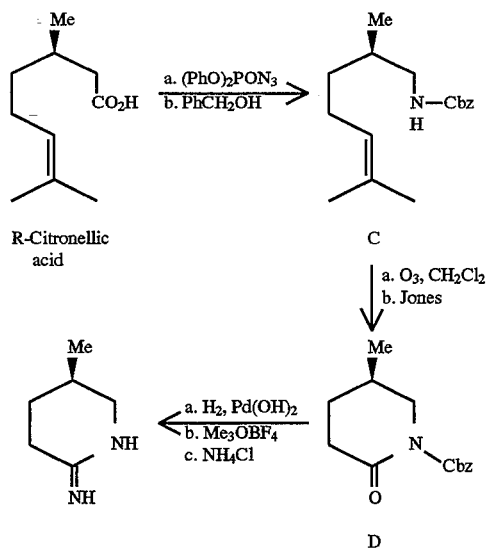

Citronellic acid can also be used in the synthesis of chiral 4,5-disubstituted 2-iminopiperidines as shown in shown in scheme 10. This method relies on stereoselective alkylation using the oxazolidone chiral auxiliary developed by Evans (*J. Amer. Chem. Soc.* 104, 1737–1739 (1982)) and the product is then converted to E. Ozonolysis of the double bond of E and cyclization of the resulting aldehyde gives F. Treatment of F with ozone followed by further oxidation gives an amino acid which is cyclized to a chiral lactam (G). Usual transformation of G furnishes cyclic amidine.

Scheme 10

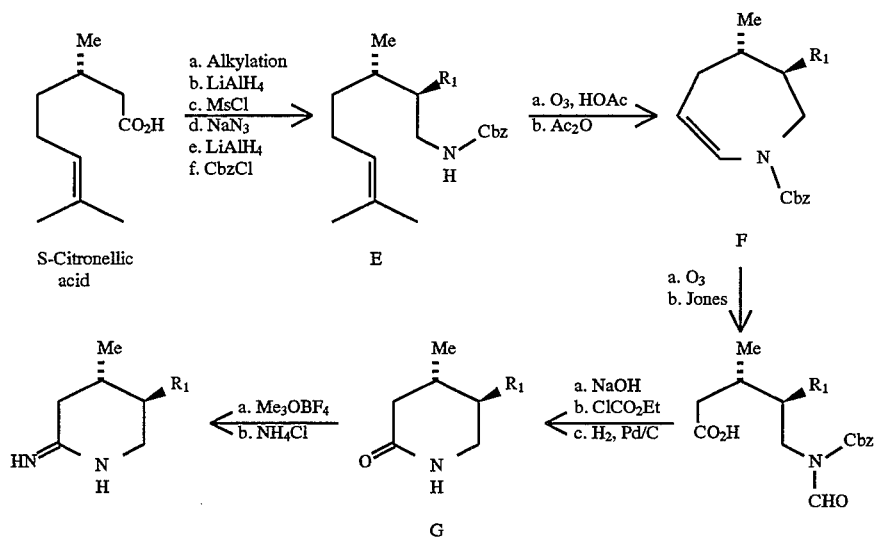

The invention will now be illustrated by the following nonlimiting examples in which, unless stated otherwise:

All operations were carried out at room or ambient temperature, that is, at a temperature in the range 18°–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta ($\delta$) values for major diagnostic protons, given in parts per million (ppm) relative to tetramethylsilane (TMS) as internal standard, determined at 400 MHz or 500 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

EXAMPLE 1

3-Methyl-2-piperidone and 5-methyl-2-piperidone

Step 1

1-(1,2-diphenyl-2-hydroxy)ethyl-3-methylpiperidine.

A mixture of 1.96 g (10 mmoles) of commercially available trans-stilbene oxide and 990 mg (10 mmoles) of 3-methyl piperidine was heated one day in refluxing ethanol. The solvent was then removed in vacuo to give the desired amino alcohol in quantitative yield.

Step B 1-(1,2-diphenyl-2-hydroxy)ethyl-3-methyl-2-piperidone & 1-(1,2-diphenyl-2-hydroxy)ethyl-5-methyl-2-piperidone A mixture of the crude amino alcohol (10 mmoles) from step A, 6.39 g (20 mmoles) of mercuric acetate and 7.5 g (20 mmoles) of ethylene diamine tetraacetic acid disodium salt in 80 mL of 1% acetic acid in water was heated to reflux 1.5 hrs. After cooling the reaction mixture, methylene chloride was added and the mixture was swirled around to dissolve all organic matter. The organic and aqueous layers were decanted from the shiny metallic mercury by-product. The aqueous layer was separated and extracted further with methylene chloride. The combined organic layers were washed with water and saturated sodium chloride solution. After drying over anhydrous magnesium sulfate, solvent was removed to give a brown crude product, which was purified on silica gel using 1:3 ethyl acetate and hexane mixture to give 639 mg of 1-(1,2-diphenyl-2-hydroxy)ethyl-3-methyl-2-piperidone and 1.5 g of 1-(1,2-diphenyl-2-hydroxy)ethyl-5-methyl-2-piperidone.

Step C 1-(1,2-diphenyl-2-oxo)ethyl-3-methyl-2-piperidone.

0.7 mL of 8N Jones reagent was added dropwise to an ice-cooled solution of 620 mg (2 mmoles) of 1-(1,2-diphenyl-2-hydroxy)ethyl-3-methyl-2-piperidone in 10 mL of acetone. The reaction mixture was then stirred one hour. 1 mL of isopropyl alcohol was added and the mixture was stirred 10 minutes. The solvent was then removed in vacuo. The residue was stirred with water and ethyl acetate until all solids dissolved. The aqueous phase was separated and extracted with ethyl acetate. The combined ethyl acetate phases were washed with water and saturated sodium chloride solution. After drying over anhydrous magnesium sulfate, the solvent was removed in vacuo to afford the desired lactam ketone as foam in quantitative yield.

Using a similar procedure, 1-(1,2-diphenyl-2-oxo)ethyl-5-methyl-2-piperidone was obtained from the oxidation of the corresponding alcohol.

Step D

3-Methyl-2-piperidone

A mixture of 550 mg (1.8 mmoles) of 1-(1,2-diphenyl-2-oxo)ethyl-3-methyl-2-piperidone and 715 mg (11 mmoles) of zinc dust in 8 mL of glacial acetic acid was heated to reflux for 1 day. The mixture was cooled and filtered and the solids washed with ethyl acetate. The filtrate was concentrated to ~5 mL. 25 mL of toluene was added and the solvents were removed in vacuo. The residue was dissolved in ethyl acetate and made basic with cautious addition of concentrated ammonium hydroxide. The initially formed precipitate dissolved upon further addition. After stirring 10 minutes, anhydrous magnesium sulfate was added in excess. After 20 minutes, the solids were filtered and washed with ethyl acetate. The filtrate was concentrated to give a residue which was purified on silica gel using 1:1 mixture of ethyl acetate and hexane first and then using 10% methanol in ethyl acetate to give 148 mg of 3-methyl-2-piperidone as fluffy solid.

$^1$H NMR(CDCl$_3$): 3.3 (m, CH$_2$N); 2.48 (m, CH$_2$C=O); 1.45–2.0 (m, CH$_2$'s); 1.24 (d, CH$_3$); 5.95 (b,NH)

Following the above procedures, the following lactams were synthesized:

5-Methyl-2-piperidone:

$^1$H NMR(CDCl$_3$): 3.3 & 2.92 (m, CH$_2$N); 2.35 (m, CH$_2$C=O); 1.4–2.0 (m, CH$_2$'s); 1.0 (d, CH$_3$); 6.1 (b,NH)

4-Methyl-2-piperidone:

$^1$H NMR(CDCl$_3$): 3.35 (m, CH$_2$N); 2.48 & 2.8 (m, CH$_2$C=O); 1.35–2.04 (m, CH$_2$'s); 1.04 (d, CH$_3$); 6.05 (b,NH)

4-Propyl-2-piperidone:

$^1$H NMR(CDCl$_3$): 3.32 (m, CH$_2$N); 2.5 & 1.98 (m, CH$_2$C=O); 1.25–1.95 (m, CH$_2$'s); 0.90 (t, CH$_3$); 6.1 (b,NH)

5,5-Dimethyl-2-piperidone:

$^1$H NMR(CDCl$_3$): 3.01 (s, CH$_2$N); 2.38 (t, CH$_2$C=O); 1.60 (t, CH$_2$); 1.04 (s, CH$_3$'s); 6.1(b,NH)

3,5-Dimethyl-2-piperidone:

$^1$H NMR(CDCl$_3$): 3.3 & 2.9 (m, CH$_2$N); 2.52 (m, CHC=O); 1.56–2.1 (m, CH$_2$'s); 1.0 & 1.28 (d, CH$_3$'s); 5.95(b,NH)

4-Benzyl-2-piperidone:

$^1$H NMR(CDCl$_3$): 3.3 (m, CH$_2$N); 2.62 (m, CH$_2$C=O); 1.35–2.48 (m, CH$_2$'s); 7.1–7.3 (m, Aromatic); 6.05 (b,NH)

4-Ethoxycarbonyl-2-piperidone:

$^1$H NMR(CDCl$_3$): 4.16 (q; CH$_2$O); 3.35 (m, CH$_2$N); 2.60 (d, CH$_2$C=O); 2.80 (CHCOOEt); 1.82–2.16 (m, CH$_2$'s); 1.24 (t, CH$_3$); 6.58 (b,NH)

1,2,3,4-Tetrahydro-1-quinolone:

$^1$H NMR(CDCl$_3$): 3.6 (t, CH$_2$N); 3.0 (t, CH$_2$); 7.2–8.05 (m, Aromatic); 6.6 (b,NH)

4-Ethoxycarbonyl-2-piperizinone:

$^1$H NMR(CDCl$_3$): 4.26 (q, CH$_2$O); 4.12 (s, NCH$_2$C=O); 3.38 & 3.66 (b, CH$_2$'s); 1.26 (t, CH$_3$); 6.66 (b, NH)

EXAMPLE 2

1-Aza-2-imino-1-cyclononane

Step A

1-Aza-2-methoxy-1-cyclononene

Trimethyloxonium tetrafluoroborate (750 mg; 5 mmol) was added in one portion to 2-azacyclononanone (700 mg; 5 mM) in 10 mL of anhydrous methylene chloride. The resulting mixture was stirred overnight at room temperature. The next morning 10% Sodium bicarbonate solution was cautiously added to neutralize fluoroboric acid and the mixture was then diluted with 20 mL of ethyl acetate. The organic layer was separated and the aqueous layer was extracted with ethyl acetate. The combined organic layers were washed with 10% sodium bicarbonate solution and with brine. After drying over anhydrous magnesium sulfate, the organic layer was concentrated to remove the solvents. The residue was taken up in hexane and filtered through a small bed of wet silica gel in hexane. The filtrate was concentrated to give 320 mg of the desired 1-aza-2-methoxy-1-cyclononene.

$^1$H NMR: 3.52 (s, OCH$_3$), 3.36 (m, CH$_2$N=), 2.24 (m, N=C—CH$_2$); 1.3–1.7(m).

The following iminoethers were synthesized according to the above general procedure. In the case of low molecular weight imino ethers such as 1-aza-2-methoxy-1-cyclopentene and its methyl analogs, 1-aza-2-methoxy-1-cyclohexene and its methyl analogs, it was necessary to use low vacuum to remove the solvents in order to reduce the loss of these more volatile products. All $^1$H NMR's are reported as δ values and were run in CDCl$_3$ 1-Aza-2-methoxy-1-cyclopentene:

$^1$H NMR: 3.72 (s, OCH$_3$), 3.58 (t, CH$_2$N=),2.36 (t, N=C—CH$_2$), 1.94 (m).

1-Aza-2-methoxy-5-methyl-1-cyclopentene:

$^1$H NMR: 3.7 & 3.73 (2s, OCH$_3$), 3.85 (m, CHN=), 2.38 (m, N=C—CH$_2$); 2.14(m) & 1.42(m)(2H), 1.12 (d, C—CH$_3$).

1-Aza-2-methoxy-3-methyl-1-cyclopentene:

$^1$H NMR: 3.68 & 3.70 (2s, OCH$_3$), 3.38 & 3.60 (21, CH$_2$N=), 2.13 & 2.58 (2m, N=C—CH), 1.40 (m), 1.16 (d, C—CH$_3$).

1-Aza-2-methoxy-1-cyclohexene:

$^1$H NMR: 3.55 (s, OCH$_3$), 3.40 (m, CH$_2$N=), 2.08 (m, N=C—CH$_2$), 1.48 & 1.64(m).

1-Aza-2-methoxy-3-methyl-1-cyclohexene:

$^1$H NMR: 3.51 (s, OCH$_3$), 3.35 (m, CH$_2$N=), 2.25 (m, N=C—CH$_2$), 1.34–1.74(m), 1.13 (d, C—CH$_3$).

1-Aza-2-methoxy-4-methyl-1-cyclohexene:

$^1$H NMR: 3.54 (s, OCH$_3$), 3.29 (m, CH$_2$N=), 2.15 (m, N=C—CH$_2$), 1.56–1.66 (m), 0.86 (d, C—CH$_3$).

1-Aza-2-methoxy-4-propyl-1-cyclohexene:

$^1$H NMR: 3.52 (br, OCH$_3$), 3.30 (m, CH$_2$N=), 2.16 (m, N=C—CH$_2$), 1.20–1.64 (m), 0.80 (t, C—CH$_3$).

1-Aza-2-methoxy-5-methyl-1-cyclohexene:

$^1$H NMR: 3.60 (b, OCH$_3$), 3.58 & 2.96 (2m, CH$_2$N=), 2.20 (m, N=C—CH$_2$), 1.32–1.77 (m), 0.92 (d, C—CH$_3$).

1-Aza-2-methoxy-5,5-dimethyl-1-cyclohexene:

$^1$H NMR: 3.62 (b, OCH$_3$), 3.17 (s, CH$_2$N=), 2.16 (t, N=C—CH$_2$), 1.47(t, CH$_2$), 0.90 (s, C—CH$_3$).

1-Aza-2-methoxy-3,5-dimethyl-1-cyclohexene:

$^1$H NMR: 3.52 (s, OCH$_3$), 2.86 (m, CH$_2$N=), 2.32 (m, N=C—CH$_2$), 1.46–1.72 (m, CH$_2$), 0.86(s, C—CH$_3$) 1.09 (s, C—CH$_3$).

1-Aza-2-methoxy-4-benzyl-1-cyclohexene:

¹H NMR: 3.61 (b, OCH₃), 3.36 (m, CH₂N=), 1.1–2.6 (m).

1-Aza-2-methoxy-1-cycloheptene:
¹H NMR: 3.34(s, OCH₃), 3.26 (m, CH₂N=), 2.23 (m, N=C—CH₂), 1.37–1.60(m).

1-Aza-2-methoxy-1-cyclooctene:
¹H NMR: 3.56 (b, OCH₃), 3.34 (m, CH₂N=), 2.24 (m, N=C—CH₂), 1.3–1.6(m).

3,4-Dihydro-2-methoxyquinoline:
¹H NMR: 6.9–7.1 (m, aromatic H), 3.78 (s, OCH₃), 2.32 (t, CH₂N=), 2.73 (t, N=C—CH₂).

3,4,5,6-Tetrahydro-4-ethoxycarbonyl-2-methoxy-pyrazine:
¹H NMR: 4.15 (q, 2H), 3.90 (s, 2H), 3.65 (s, OCH₃), 3.42 (m, 2H), 2.50 (m, 2H), 1.22 (t,3H).

Step B

2-Imino-1-azacyclononane hydrochloride.

A mixture of 1-aza-2-methoxy-1-cyclononene (62 mg; 0.4 mmol) and ammonium chloride (20.5 mg; 0.4 mmol) in 1 mL of anhydrous ethanol was heated to reflux 3 hours. The solvent was then removed in vacuo and the residue was triturated with Et2O to give almost a quantitative yield of 2-imino-1-azacyclononane hydrochloride as an amorphous solid.

¹H NMR(CDCl₃): 8.7, 9.0 & 9.6 (3 br,NH's), 3.4 (m, CH₂N), 2.7 (m, CH₂C=N), 1.5–2.0(m).

Mass Spectrum m/e=141

Note: In some cases a slight molar excess (5–10%) of the iminoether was used. The workup was effected by triturating the residual product with ethyl acetate or ether. In specified cases the products were obtained as thick oils.

The following cyclic amidines were synthesized according to the above general procedure by employing an appropriate iminoether instead of 1-aza-2-methyl-1-cyclononene and appropriate amine hydrochloride instead of ammonium chloride. All NMR's are reported as δ values.

1-Aza-2-imino-cyclopentane hydrochloride:
¹H NMR(CDCl₃): 9.44, 9.13 & 8.77 (3br, N—H's), 2.88 (t, CH₂N), 2.88 (t, CH₂C=N), 2.10(m).

Mass Spectrum m/e=84.9 (M+1).

1-Aza-2-imino-3-methylcyclopentane hydrochloride:
¹H NMR(CDCl₃): 9.48, 9.1 & 8.82 (3br, N—H's), 3.6–3.2 (m, CH₂N), 2.36 (t, CHC=N), 1.80 (m), 1.42 (d, C—CH₃).

Mass Spectrum m/e=99.1 (M+1).

1-Aza-2-imino-5-methylcyclopentane hydrochloride:
¹H NMR(CDCl₃): 9.5, 9.18 & 8.78 (3br, N—H's), 4.06 (t, CHN); 3.04–2.92 (m, CH₂C=N), 2.35 (m, CH₂), 1.32 (d,CCH₃).

Mass Spectrum m/e=99.1 (M+1).

1-Aza-2-methylamino-1-cyclopentene hydrochloride: (oil)
¹H NMR (CDCl₃): 10.1 & 10.03 (2br, N—H's), 3.66 (b, CH₂N), 3.08 (d, N—CH₃), 2.91 (t, CH₂C=N), 2.12 (m).

Mass Spectrum m/e=98.9 (M+1).

1-Aza-2-ethylamino-1-cyclopentene hydrochloride: (oil)
¹H NMR (D₆-DMSO): 10.13 & 9.9 (2br, N—H's), 3.7 (m, CH₂N), 3.58 (m, N—CH₃), 2.96 (m, CH₂C=N), 2.12 (m), 1.28 (t, CCH₃).

Mass Spectrum m/e=112.9 (M+1).

1-Aza-2-benzylamino-1-cyclopentene hydrochloride:
¹H NMR (D₆-DMSO): 10.16 (br,N—H's), 7.3–7.4 (m, aromatic H's), 4.54 (s, CH₂Ph), 3.56 (t, CH₂N), 2.84 (t, CH₂C=N), 2.06 (m).

Mass Spectrum m/e=175 (M+1).

1-Aza-2-cyclohexylamino-1-cyclopentene hydrochloride.
¹H NMR (D₆-DMSO): 9.8 & 9.5 (2br, N—H's), 3.55 (t, CH₂N), 2.78 (t, CH₂C=N), 2.04 (m), 1.2–1.88(m).

Mass Spectrum m/e=167 (M+1).

1-Aza-2-methoxycarbonylmethylamino-1-cyclopentene hydrochloride: (oil)
¹H NMR (D₆-DMSO): 10.0 (br, N—H's), 4.25 (s, —NCH₂COOMe), 3.7 (s, COOCH₃), 3.6 (t, CH₂N), 2.86 (t, CH₂C=N), 2.1(m).

Mass Spectrum m/e=156.9 (M+1).

1-Aza-2-((3,4-dihydroxyphenyl)ethyl)amino-1-cyclopentene hydrochloride:
¹H NMR (D₆-DMSO): 9.5 (b,N—H's), 6.46–6.76 (m, aromatic H), 3.54 (t, CH₂), 3.36 (t, CH₂), 2.74 (t, CH₂), 2.02(m).

Mass Spectrum m/e=220.9 (M+1).

1-Aza-2,2-dimethylamino-1-cyclopentene hydrochloride.
¹H NMR(CDCl₃): 11.24 (b, N—H's), 3.8 (t, CH₂N), 3.4 (s, N—CH₃), 3.16 (t, CH₂C=N), 2.86 (t, CH₂), 2.2(m).

Mass Spectrum m/e=113 (M+1).

2-Iminopiperidine hydrochloride

1-Aza-2-methylamino-1-cyclohexene hydrochloride: (oil)
¹H NMR(D₆-DMSO): 9.3 & 9.22 (2br, NH's), 3.30 (m, CH₃), 2.78 (d, CH₃), 2.52 (m, CH₂C=N); 1.70(m).

Mass Spectrum m/e=112.9 (M+1).

1-Aza-2-ethylamino-1-cyclohexene hydrochloride:
¹H NMR (D₆-DMSO): 9.3 (br, NH's), 3.28 (m, CH2N) 3.20 (m, CH₂N), 2.5 (m, CH₂C=N), 1.20 (t, CH₃).

Mass Spectrum m/e=127(M+1).

1-Aza-2-dimethylamino-1-cyclohexene hydrochloride.
¹H NMR (CDCl₃): 10.7 (br, NH's), 3.60 (m, CH₂N), 3.40 & 3.12 (2s, CH₃), 2.63–2.52 (m, CH₂), 1.85–1.77 (m).

Mass Spectrum m/e=127 (M+1).

2-Imino-3-methylpiperidine hydrochloride:
¹H NMR (D₆-DMSO): 9.5 & 8.6 (2br,NH's), 3.25 (m, CH₂N), 2.7 (m, CHC=N), 1.4–1.9 (m), 1.25 (d, CH₃).

Mass Spectrum m/e=113.1 (M+1).

2-Imino-4-methylpiperidine hydrochloride:
¹H NMR (D₆-DMSO): 9.5, 8.68 & 8.35 (3br, NH's), 3.24 (m, CH₂N), 2.55 & 2.15 (m, CH₂C=N), 1.35–1.85 (m), 0.96 (d,CH₃).

Mass Spectrum m/e=113.1 (M+1).

2-Imino-4-propylpiperidine hydrochloride:
¹H NMR (D₆-DMSO): 9.5 & 8.7 (2br, NH's), 3.22 (m, CH₂N), 2.6–2.16 (m, CH₂C=N), 1.3–1.8(m), 0.85 (t, CH₃).

Mass Spectrum m/e=141.1 (M+1).

b 2-Imino-4-benzylpiperidine hydrochloride:
¹H NMR (D₆-DMSO): 9.54, 8.64 & 8.36 (3br, NH's), 7.15–7.35 (m, aromatic H), 3.35 & 3.2 (m, CH₂N), 2.6(m, CH₂C=N), 1.4–2.06(m).

Mass Spectrum m/e=190.2 (M+1).

2-Imino-5-methylpiperidine hydrochloride:
¹H NMR (D₆-DMSO): 9.5, 8.7 & 8.4 (3br, NH's), 3.3 & 2.8 (m, CH₂N), 2.55 (m, CH₂C=N), 1.3–1.8 (m), 0.92 (d, CH₃).

Mass Spectrum m/e=113.1 (M+1).

2-Imino-5,5-dimethylpiperidine hydrochloride:
¹H NMR (D₆-DMSO): 9.5 & 8.4 (2br, NH's), 2.95 (s, CH₂N), 2.52 (t, CH₂C=N), 1.48 (t, CH₂), 0.92 (d, CH₃).

Mass Spectrum m/e=127.1 (M+1).

2-Imino-3,5-dimethylpiperidine hydrochloride:
¹H NMR (D₆-DMSO): 9.45, 8.7 & 8.5 (3br, NH's), 3.32 (m, CH₂N), 2.64 (m, CHC=N), 1.6–2.22(m).

Mass Spectrum m/e=112.9 (M+1).

1-Aza-2-iminocycloheptane hydrochloride:
¹H NMR (CDCl₃): 9.5, 9.0 & 8.45 (3br,NH's), 3.4 (m, CH₂N), 2.75 (m, CH₂C=N), 1.4–1.8(m).

Mass Spectrum m/e=127.1 (M+1).

1-Aza-2-methylamino-1-cycloheptene hydrochloride:
¹H NMR(CDCl₃): 10.0 & 9.5 (2br, NH's), 3.50 (m, CH₂), 3.0 (d, CH₃), 2.8 (m, CH₂C=N), 1.6–1.84(m).

Mass Spectrum m/e=127 (M+1).

1-Aza-2-ethylamino-1-cycloheptene hydrochloride: (oil)

$^1$H NMR (CDCl$_3$): 9.8 & 9.54 (2br, NH's), 3.52 (m, CH$_2$), 2.85 (m, CH$_2$C=N), 1.70 (m), 1.3 (t, CH$_3$).

Mass Spectrum m/e=141 (M+1).

1-Aza-2-dimethylamino-1-cycloheptene hydrochloride.

$^1$H NMR (CDCl$_3$): 3.65 (m, CH$_2$N), 3.42 & 3.25 (2s, CH$_3$), 2.72 (m,CH$_2$), 1.6–1.85(m).

Mass Spectrum m/e=141 (M+1).

1-Aza-2-benzylamino-1-cycloheptene hydrochloride:

$^1$H NMR (D$_6$-DMSO): 9.9 & 9.6 (2br, NH's), 7.4 (m, aromatic H), 4.48 (b, CH$_2$), 3.45 (m, CH$_2$N), 2.76 (m, CH$_2$C=N), 1.5–1.75 (m).

Mass Spectrum m/e=203 (M+1).

1-Aza-2-cyclohexylamino-1-cycloheptene hydrochloride.

1H NMR (D$_6$-DMSO): 9.2 (br, N—H's), 3.38 (m, CH$_2$N), 2.68 (t, CH$_2$C=N), 1.1–1.88 (m).

Mass Spectrum m/e=195 (M+1).

1-Aza-2-iminocyclooctane hydrochloride:

$^1$H NMR (CDCl$_3$): 9.6, 9.0 & 8.7 (3br, NH's), 3.45 (m, CH$_2$N), 2.7 (m, CH$_2$C=N), 1.5–2.0(m).

Mass Spectrum m/e=127 (M+1).

1-Aza-2-methylamino-1-cyclooctene hydrochloride:

$^1$H NMR (CDCl$_3$): 10.0 & 9.34 (2br, NH's), 3.55 (m,CH$_2$), 3.05 (d, CH$_3$), 2.75 (m, CH$_2$C=N), 1.48–1.95(m).

Mass Spectrum m/e=141 (M+1).

1-Aza-2-ethylamino-1-cyclooctene hydrochloride:

$^1$H NMR (CDCl$_3$): 8.2–10.0(br, NH's), 3.55 (m, CH$_2$), 2.5–2.76 (m, CH$_2$C=N), 1.26–2.05 (m), 1.3 (t, CH$_3$).

Mass Spectrum m/e=155.2 (M+1).

1-Aza-2-benzylamino-1-cyclooctene hydrochloride:

$^1$H NMR (D$_6$-DMSO): 9.9 & 9.3 (2br, NH's), 7.36 (m, aromatic H), 4.5 (b, CH$_2$), 3.5 (m, CH$_2$N), 2.7 (m, CH$_2$C=N), 1.3–1.75(m).

Mass Spectrum m/e=217 (M+1).

1-Aza-2-methylamino-1-cyclononene hydrochloride:

$^1$H NMR (D$_6$-DMSO): 9.64 & 8.95 (2br, NH's), 3.5 (m, CH$_2$), 3.05 (d, CH$_3$), 2.82 (d, CH$_3$), (2.64 (m, CH$_2$C=N), 1.25–1.8(m).

Mass Spectrum m/e=155 (M+1).

3,4-Dihydro-2-aminoquinoline hydrochloride:

$^1$H NMR (D$_6$-DMSO): 9.7 & 8.9 (2br, NH's), 7.1–7.3 (m, aromatic H), 2.9 (m, CH$_2$).

Mass Spectrum m/e=146.9 (M+1).

3,4-Dihydro-2-methylaminoquinoline hydrochloride:

$^1$H NMR (D$_6$-DMSO): 11.3 & 10.45 (2br, NH's), 7.1–7.5 (m, aromatic H), 3.1 (d, CH$_3$), 2.9 (CH$_2$).

Mass Spectrum m/e=160.9 (M+1).

3,4-Dihydro-2-ethylaminoquinoline hydrochloride:

$^1$H NMR (D$_6$-DMSO): 10.4 (br, NH's), 7.1–7.5 (m, aromatic H), 3.58 (m, CH$_2$), 2.9 (CH$_2$), 1.25 (t, CH$_3$).

Mass Spectrum m/e=174.9 (M+1).

3,4-Dihydro-2-benzylaminoquinoline hydrochloride:

$^1$H NMR (D$_6$-DMSO): 10.75 (br, NH's), 7.1–7.55 (m, aromatic H), 4.86 (b, CH$_2$), 3.1 (d, CH$_3$), 2.95 (m, CH$_2$).

Mass Spectrum m/e=236.9 (M+1).

3,4-Dihydro-2-cyclohexylaminoquinoline hydrochloride:

$^1$H NMR (D$_6$-DMSO): 10.2 (br, NH's), 7.1–7.6 (m, aromatic H), 2.9 (CH$_2$), 1.1–2.0(m).

Mass Spectrum m/e=229 (M+1).

3,4-Dihydro-2-dimethylaminoquinoline hydrochloride:

$^1$H NMR (D$_6$-DMSO): 8.8 (br, NH's), 7.1–7.6 (m, aromatic H), 3.4 & 3.3 (2s, CH$_3$), 2.95(CH$_2$).

Mass Spectrum m/e=174.9 (M+1).

4-Ethoxycarbonyl-2-imino-piperazine hydrochloride:

$^1$H NMR (D$_6$-DMSO): 9.1 & 8.8 (2br, NH's), 4.38 (br, CH$_2$), 4.1 (q, CH$_2$), 3.56 (br, CH$_2$), 3.35 (t, CH$_2$), 1.2 (t, CH$_3$).

Mass Spectrum m/e=172.1 (M+1).

EXAMPLE 3

5-(S)-2-Imino-1-aza-bicyclo(3.3.0)octane

Step A 1-t-butoxycarbonyl-2-(S)-pyrrolidinomethanol

To a vigourously stirring solution of 2.5 g (24.7 mmol) 2-(S)-pyrrolidinomethanol in 20 mL of saturated sodium bicarbonate solution at RT was added 6.25 mL (27.2 mmol) of di-t-butyl dicarbonate. Reaction was continued overnight at room temperature. Reaction mixture was diluted with water and extracted with EtOAc. EtOAc layer was washed with water, brine, dried, filtered and the filtrate was concentrated. Trituration of the white solid with hexane followed by filtration yielded 4.3 g of the desired compound.

$^1$H NMR (CDCl3): 4.76 (br s, 1H), 3.98 (br, 1H), 3.29–3.67 (m, 4H), 2.00–2.06(m, 1H), 1.78–1.84(m, 2H), 1.48 (s, 9H).

Step B 1-t-Butoxycarbonyl-2-(S)-formyl-pyrrolidine.

To a solution of 0.44 mL (6.2 mmol) of DMSO in 3 mL of CH$_2$Cl$_2$ at −78° C. was added 0.36 mL (4.1 mmol) of Oxalyl chloride. After 10 min 0.402 g (2 mmol) of 1-t-butoxycarbonyl-2-(S)-pyrrolidinomethanol was added and stirred for 20 min. Triethylamine (1.7 mL, 12.4 mmol) was added to the reaction mixture and it was allowed to warm to room temperature. After stirring for 15 min at room temperature, the reaction was diluted with water and extracted with CH$_2$Cl$_2$. The CH$_2$Cl$_2$ layer was washed with brine, dried and the filtrate was concentrated. The residue was chromatographed using 20% Et$_2$O-hexane to isolate 0.436 g (quantitative) of the title compound mixed with a small amount of DMSO which was used in the next step.

Step C 1-t-Butoxycarbonyl-2-(S)-methoxycarbonylethyl-pyrrolidine.

To a suspension of 0.16 g (4 mmol) of NaH in 10 mL of THF was added 0.73 mL (4 mmol) of methyl diethylphosphonoacetate. After 10 min a solution of 0.436 g (2 mmol) of 1-t-butoxycarbonyl-2-(S)-formyl-pyrrolidine prepared in step B was added. After stirring for 1 h the reaction was quenched by adding saturated NH4Cl and extracted with CH$_2$Cl$_2$. The CH$_2$Cl$_2$ layer was washed with brine, dried, concentrated and the residue was purified by chromatography using 20% EtOAc-hexane to furnish 0.383 g of an oil.

$^1$H NMR (CDCl$_3$): 6.82 (dd, J=15.5, 6 Hz, 1H), 5.83 (d, J=15.5, 1H), 4.4 (m, 1H), 3.72 (s, 3H), 3.40 (m, 2H), 2.08 (m, 1H), 1.86 (m, 1H), 1.77 (m, 1H), 1.43 (s, 9H). $^{13}$C NMR (CDCl$_3$ in ppm): 166.87, 148.84, 120.00, 57.81, 51.53, 46.18, 31.68, 28.35, 22.86.

A solution of 0.383 g of this oily product in 5 mL of methanol and 50 mg of 10% Pd/C was stirred under H2 atmosphere overnight. The next morning the catalyst was filtered through a plug of celite and the filtrate was concentrated to obtain 0.368 g (72%) of the title compound sufficiently pure for use in the next step.

¹H NMR (CDCl₃): 3.78(m, 1H), 3.65 (s, 3H), 3.28 (m, 2H), 2.32 (t, J=7.5 Hz, 2H), 1.45 (s, 9H).

Step D 5-(S)-1-Aza-bicyclo(3.3.0)octan-2-one

A solution of 0.201 g (0.78 mmol) of 1-t-butoxycarbonyl-2-(S)-methoxycarbonylethyl-pyrrolidine in 3 mL of CH₂Cl₂ at 0° C. was treated with 1 mL of trifluoroacetic acid. During the next 1 h as the solution warmed to room temperature the reaction was complete. The reaction was concentrated and saturated K₂CO₃ solution was added to the residue until it was basic. The mixture was heated in a 75° C. for 18 h. The reaction was cooled and extracted with CH₂Cl₂ and the organic layer was washed with brine, dried and concentrated. The residue was chromatographed on a flash column using 10:45:45 mixture of MeOH:EtOAc:hexane to isolate 96 mg (98%) of the title compound.

¹H NMR (CDCl₃): 3.88 (m, 1H), 3.53 (m, 1H), 3.03 (m, 1H), 2.72 (m, 1H), 2.31 (m, 1H), 2.02–2.28 (m, 3H), 1.73 (m, 1H), 1.32 (m, 1H). ¹³C NMR (CDCl₃ in ppm): 174.71, 62.04, 40.94, 35.35, 32.18, 27.15, 26.97.

Step E 5-(S)-1-Aza-bicyclo(3.3.0)octan-2-thione

To a solution of 80 mg (0.64 mmol) of 5-(S)-1-aza-bicyclo(3.3.0)octan-2-one in 4 mL of toluene was added 0.388 g (0.96 mmol) of Lawesson's reagent and the mixture was heated in a 90° C. bath. After 18 h the reaction was cooled, concentrated and the residue was chromatographed using 20% EtOAc-hexane to furnish 83 mg (92%) of the title compound.

¹H NMR (CDCl₃): 4.17 (m, 1H), 3.72 (m, 1H), 3.40–3.23 (m, 3H), 2.38–2.21 (m, 4H), 1.78 (m, 1H), 1.47 (m, 1H). ¹³C NMR (CDCl₃ in ppm): 69.68, 49.36, 44.56, 31.60, 29.36, 27.50.

Step F 5-(S)-2-Imino-1-aza-bicyclo(3,3,0)octane.

Methyl iodide (1.5 mL) was added to 83 mg (0.59 mmol) of 5-(S)-1-aza-bicyclo(3,3,0)octan-2-thione and the mixture was stirred overnight. Next morning excess methyl iodide was removed in vacuo leaving a solid residue.

¹H NMR (D2O): 4.66 (m, 1H), 3.53 (m, 1H), 3.68–3.57 (m, 4H), 2.76 (s, 3H), 2.53–2.41 (m, 3H), 2.26 (m, 1H), 2.03 (m, 1H), 1.66 (m, 1H). ¹³C NMR (D2O in ppm): 187.28, 75.86, 45.84, 43.19, 29.53, 27.52, 27.05, 15.40.

The solid obtained from above reaction was dissolved in 5 mL of MeOH and the solution was saturated with NH₃. After stirring for 18 h the reaction mixture was concentrated leaving a white solid residue. The solid was triturated with ether and dried to isolate 0.161 g (quantitative) of the title compound as a hydroiodide salt.

¹H NMR (D₂O): 4.31 (m, 1H), 3.40 (m, 2H), 3.25 (m, 1H), 3.04 (m, 1H), 2.36–2.27 (m, 4H), 1.94 (m, 1H), 1.53 (m, 1H). ¹³C NMR (D₂O in ppm): 165.37, 69.08, 49.03, 42.66, 35.96, 30.38, 27.83, 27.18.

EXAMPLE 4

2-Imino-1-aza-bicyclo(4.3.0)nonane

Step A 1-t-butoxycarbonyl-2-(R+S)-piperidinomethanol

Starting from 5 gm (43.4 mmol) of 2-(R+S)-piperidinomethanol and following the procedure as in example 3, step A gave 7.06 gm of the title product.

¹H NMR (CDCl₃): 4.26 (m, 1H), 3.92 (m, 1H), 3.77(m, 1H), 3.59 (m, 1H), 2.84 (m, 1H), 1.49–1.60 (m, 3H), 1.44 (s, 9H). ¹³C NMR (CDCl₃ in ppm): 79.72, 61.40, 52.37, 39.95, 33.88, 28.37, 25.19, 25.11, 19.50.

Step B 1-t-Butoxycarbonyl-2-(R+S)-formyl-piperidine

Starting from 0.7 gm (3.2 mmol) of 1-t-butoxycarbonyl-2-(R+S)-piperidinomethanol and following the procedure as in example 3, step B, gave 0.675 gm of the desired compound.

¹H NMR (CDCl₃): 9.60 (d, J=5.7 Hz, 1H), 4.55 (br s,1H), 3.95 (br s, 1H), 2.94 (br s, 1H), 2.17 (m, 1H), 1.67–1.28 (m, 5H), 1.48 (s, 9H).

Step C 1-t-Butoxycarbonyl-2-(R+S)-methoxycarbonylethyl-piperidine

To a suspension of 0.088 g (3.7 mmol) of NaH in 5 mL of THF was added 0.68 mL (4 mmol) of methyl diethylphosphonoacetate at −10° C. After 10 min a solution of 0.528 g (2.47 mmol) of 1-t-butoxycarbonyl-2-(R+S)-formyl-piperidine prepared in step B was added. After stirring for 1 h the reaction was quenched by adding saturated NH₄Cl and extracted with EtOAc. The EtOAc layer was washed with brine, dried, concentrated and the residue was purified by chromatography using 5% EtOAc-hexane to furnish 0.579 g of oil.

¹H NMR (CDCl₃): 6.88 ( m, 1H), 5.81 (d, J=15.8, 1H), 4.94 (m, 1H), 3.98 (m, 2H), 3.74 (s, 3H), 2.81 (m, 1H), 1.81–1.60 (m, 5H), 1.45 (s, 9H). ¹³C NMR (CDCl₃in ppm): 166.61, 154.94, 121.56, 79.79, 51.53, 28.89, 28.33, 25.22, 19.81.

A solution of 0.570 g of this oily product in 5 mL of methanol and 50 mg of PtO₂ was stirred under H₂ atmosphere overnight. The next morning the catalyst was filtered through a plug of celite and the filtrate was concentrated to obtain 0.548 g of the title compound sufficiently pure for use in the next step.

¹H NMR (CDCl₃): 4.24(m, 1H), 3.66 (s, 3H), 2.73 (m, 1H), 2.31–2.25 (m, 2H), 2.13–2.07 (m, 1H), 1.69–1.50 (m, 6H 1.45 (s, 9H). ¹³C NMR (CDCl₃ in ppm): 174.00, 154.96, 79.20, 51.49, 49.88, 30.89, 28.85, 28.37, 28.27, 25.50, 24.96, 19.01.

Step D 5-(R+S)-1-Aza-bicyclo(4.3.0)nonan-2-one

A solution of 0.548 g (2.02 mmol) of 1-t-butoxycarbonyl-2-(R+S)-methoxycarbonylethyl-piperidine in 3 mL of CH₂Cl₂ at 0° C. was treated with 1 mL of trifluoroacetic acid. During the next 1 h as the solution warmed to room temperature the reaction was complete. The reaction was concentrated and saturated K₂CO₃ solution was added to the residue until it was basic. The mixture was heated in a 75° C. for 2 h. The reaction was cooled and extracted with CH₂Cl₂ and the organic layer was washed with brine, dried and concentrated. The residue was chromatographed on a flash column using 10:45:45 mixture of MeOH:EtOAc:hexane to isolate 0.187 g (67%) of the title compound.

¹H NMR (CDCl₃): 4.04 (m, 1H), 3.34 (m, 1H), 2.54 (m, 1H), 2.27 (m, 1H), 2.14 (m, 1H), 1.80 (m, 2H), 1.63 (m, 1H), 1.50 (m, 1H), 1.36–1.23 (m, 2H), 1.09 (m, 1H). ¹³C NMR (CDCl₃ in ppm): 173.47, 57.17, 40.11, 33.48, 30.20, 25.23, 24.35, 23.58.

Step E 5-(R+S)-1-Aza-bicyclo(4.3.0)nonan-2-thione

To a solution of 90 mg (0.64 mmol) of 5-(R+S)-1-aza-bicyclo(4.3.0)nonan-2-one in 4 mL of toluene was added 0.392 g (0.97 mmol) of Lawesson's reagent and the mixture was heated in a 90° C. bath. After 18 h the reaction was cooled, concentrated and the residue was chromatographed using 70% CH2Cl2-hexane to furnish 95 mg (96%) of the title compound.

¹H NMR (CDCl₃): 4.85 (m, 1H), 3.71 (m, 1H), 3.05 (m, 1H), 2.94 (m, 1H), 2.83 (m, 1H), 2.26 (m, 1H), 2.00 (m, 1H), 1.89 (m, 1H), 1.83 (m, 1H), 1.65 (m, 1H), 1.53–1.42 (m, 2H), 1.28 (m, 1H). ¹³C NMR (CDCl₃ in ppm): 199.15, 65.13, 45.53, 43.40, 33.34, 26.66, 24.23, 22.99.

Step F 5-(R+S)-2-Imino-1-aza-bicyclo(4.3.0)nonane.

Methyl iodide (1 mL) was added to 50 mg (0.32 mmol) of 5-(R+S)-1-aza-bicyclo(4.3.0)nonan-2-thione and the mixture was stirred for 5 hr. Excess methyl iodide was removed in vacuo leaving a solid residue.

¹H NMR (D₂O): 4.20 (m, 1H), 4.07 (m, 1H), 3.45–3.26 (m, 3H), 2.74(s, 3H), 2.51 (m, 1H), 2.11 (m, 1H), 1.90 (m, 2H), 1.58–1.49 (m, 3H). ¹³C NMR (D₂O in ppm): 70.41, 48.57, 37.01, 32.30, 25.43, 23.66, 21.73, 14.91.

The solid obtained from the above reaction was dissolved in 5 mL of MeOH and the solution was saturated with NH₃. After stirring for 18 h the reaction mixture was concentrated leaving a white solid residue. The solid was triturated with ether and dried to isolate 83 mg (quantitative) of the title compound as a hydroiodide salt.

¹H NMR (D₂O): 3.84–3.78 (m, 2H), 3.07 (m, 1H), 2.85 (m, 2H), 2.32(m, 1H), 2.01 (m, 1H), 1.86–1.72 (m, 4H), 1.48 (m, 2H), 1.34 (m, 1H). ¹³$_C$ NMR (D₂O in ppm): 166.27, 63.61, 43.14, 31.94, 29.93, 25.30, 23.30, 21.97.

EXAMPLE 5 cis-4,6-Dimethyl-2-imino-piperidine, acetic acid salt

2-Amino-4,6-dimethyl-pyridine (2.00 g, 16.4 mmol) was dissolved in 10.0 mL of glacial acetic acid and 0.90 g of 5% rhodium on alumina was added. The mixture was shaken under a hydrogen atmosphere at 40 psi for 16 h. After filtering the mixture through Celite and washing the catalyst with an additional 25 mL of acetic acid, the filtrate was concentrated to a weight of 4.5 g. Toluene (3×10 mL) and then ethyl acetate (20 mL) were added sequentially, with evaporation of the solvent under vacuum following the addition of each portion. The residue was dissolved in methanol and filtered through a 0.45 micron membrane. The filtrate was evaporated and the residue was dissolved in 20 mL of ethyl acetate and cooled to 0° C. Filtration and drying under vacuum yielded 958 mg (31% yield) of cis-4,6-dimethyl-2-imino-piperidine, acetic acid salt.

¹H-NMR (400 MHz, CD₃OD) δ3.58 (m, 1H), 2.62 (ddd, 1H, J=17.5, 4.5, 2 Hz), 2.16 (ddd, J=17.5, 12, 1.5 Hz), 2.00–1.90 (m, 2H), 1.89 (s, 3H), 1.27 (d, 3H, J=6 Hz), 1.11 (q, 1H, J=12 Hz), 1.06 (d, 3H, J=6 Hz).

Mass spectrum: 127 (M+1).

Following the above procedures, the following 2-iminopiperidines were synthesized from the appropriate 2-aminopyridine:

2-Imino-4-methyl-piperidine, acetic acid salt

¹H-NMR (400 MHz, CD₃OD) δ3.24 (ddd, 1H, J=13, 5.5, 2.5 Hz), 3.14 (ddd, 1H, J=13, 10, 5 Hz), 2.45 (ddd, 1H, J=17.5, 5, 1.5 Hz), 2.04 (dd, J=17.5, 10 Hz), 1.88–1.68 (m, 2H), 1.64 (s, 3H), 1.30 (dtd, 1H, J=13, 10, 5.5 Hz), 0.95 (d, 3H, J=6 Hz). Chemical Analysis. Calc. for C₈H₁₆N₂O₂: 55.79% C, 9.36% H, 16.27% N. Found: 55.95% C, 9.29% H, 16.33% N.

6-Ethyl-2-imino-4-methyl-piperidine, acetic acid salt.

¹H-NMR (400 MHz, CD₃OD) δ3.48–3.39 (m, 1H), 2.63 (ddd, 1H, J=17.5, 4.5, 2 Hz), 2.17 (ddd, 1H, J=17.5, 12, 1.5 Hz), 2.03–1.90 (m, 2H), 1.90 (s, 3H), 1.69 (dqd, J=14, 7, 5 Hz), 1.56 (dq, J=14, 7 Hz), 1.10 (q, J=12 Hz), 1.07 (d, 3H, J=7 Hz), 0.98 (t, J=7 Hz).

4-Imino-5-cis-methyl-3-azabicyclo[4.3.0]nonane, hydrochloride.

¹H NMR (400 MHz, CDCl₃) δ3.42 (dm, 1H, J=13 Hz), 3.23 (d, 1H, J=13 Hz), 2.84–2.87 (m, 1H), 2.62–2.49 (1H, m), 2.02–1.95 (1H, m), 1.93–1.86 (1H, m), 1.76–1.69 (1H, m), 1.41-1.28 (2H, m), 1.249 (3H, d, J=7 Hz), 0.95–0.86 (1H, m). Mass spectrum: 153 (M+1).

cis-5-Aminomethyl-4,6-dimethyl-2-imino-piperidine, dihydrochloride.

¹H NMR (400 MHz, CDCl₃) δ3.95–3-88 (m, 1H), 3.05(t, 2H, J=5 Hz), 2.73 (dd, 1H, J=17 Hz, J=5.5 Hz), 3.05 (t, 2H J=4.5 Hz), 2.73 (dd, 1H, J=18 Hz, J=5.5 Hz), 2.37 (dd, 1H, J=18 Hz, J=9.5 Hz), 2.4–2.3 (m, 1H), 2.25–2.20 (m, 1H,), 1.37 (d, 3H, J=7.1 Hz), 1.15 (d, 3H, J=6.7 Hz). Mass spectrum: 156 (M+1).

cis-3-Ethyl-2-imino-4-methyl-piperidine, hydrochloride.

¹H NMR (500 MHz, CD₃OD) δ3.44 (m, 1H), 3.38 (m, 1 H), 2.48 (dd, J=4 Hz, 1H), 2.16 (m, J=10 & 4 Hz, 1H), 1.83 (m, 1H), 1.74 (m, 2H), 1.67 (m, 1H), 1.06 (t, J=8 Hz, 3H), 1.05 (d, J=7 Hz, 3H). Mass spectrum: 141 cis-2-Imino-4-methyl-3-n-propyl-piperidine, hydrochloride.

¹H NMR (500 MHz, CD₃OD) δ3.44 (m, 1H), 3.38 (m, 1H), 2.55 (dd, J=5 Hz, 1H), 2.15 (m, J=10 & 4 Hz, 1H), 1.83 (m, 1H, H₅), 1.76 (m, 1H), 1.59 (m, 2H), 1.45 (m, 2H), 1.05 (d, J=7 Hz, 3H), 0.99 (t, J=7 Hz, 3H). Mass spectrum: 155 cis/trans-2-Imino-4-methyl-piperidine-5-carboxylic acid, acetic acid salt.

¹H NMR (400 MHz, CD₃OD) δ1.04 (d, 1.5H), 1.08 (d, 1.5H). Mass spectrum: 156 (M).

cis/trans-2-Imino-4-methyl-piperidine-5-carboxylic acid, methyl ester, acetic acid salt.

¹H NMR (400 MHz, CD₃OD) δ1.05 (d, 1.5H), 1.09 (d, 1.5H), 3.74 (d, 3H). Mass spectrum: 171 (M+1).

cis/trans-5-Acetamidomethyl-2-imino-4-methyl-piperidine, acetic acid salt.

¹H NMR (400 MHz, CD₃OD) δ1.02 (d, 1.5H), 1.10 (d, 1.5H). Mass spectrum: 184 (M+1).

2-Imino-5-n-propyloxy-piperidine, acetic acid salt.

¹H NMR (400 MHz, CD₃OD) δ0.95 (t, 3H), 1.59 (m, 2H). Mass spectrum: 157 (M+1).

cis/trans-5-Acetamido-2-imino-4-methyl-piperidine, acetic acid salt.

¹H NMR (400 MHz, CD₃OD) δ1.00 (d, 1.5H), 1.05 (d, 1.5H), 1.97 (d, 3H). Mass spectrum: 170 (M+1).

5-Cyclohexyl-2-imino-piperidine, acetic acid salt.

$^1$H NMR (400 MHz, CD$_3$OD) δ1.00–1.85 (br m, 11H). Mass spectrum: 181 (M+1).

cis/trans-5-Cyclohexyl-2-imino-4-methyl-piperidine, acetic acid salt.

$^1$H NMR (400 MHz, CD$_3$OD) δ0.90 (d, 1.5H), 1.05 (d, 1.5H). Mass spectrum: 195 (M+1).

2-Imino-5-trifluoro-piperidine.

$^1$H NMR (400 MHz, CD$_3$OD) δ1.83–1.97 (br m, 1H), 2.14–2.20 (br m, 1H), 2.74–2.80 (br m, 2H), 2.86–3.00 (br m, 1H), 3.337–3.44 (m, 1H), 3.62–3.68 (q, 1H). Mass spectrum: 167 (M+1).

EXAMPLE 6

2-Imino-5-ethyl-4-methylpyrrolidine hydrochloride

Step A

Methyl 3-methyl-4-nitrohexanoate

A solution of 4 g (40 mmol) of methyl crotonate and 4.72 g (53 mmol) of 1-nitropropane in 20 mL of acetonitrile was treated with 6 mL (40 mmol) of 1,8-diazobicyclo[5.4.0]undec-7-ene (DBU). After stirring for 22 h at room temperature the reaction mixture was diluted with water and acidified with 2N HCl. The solution was extracted with Et2O and the Et2O layer was washed with brine, dried and concentrated. The residue was chromagraphed on a flash column using 10% Et2O-Hexane to isolate 6.41 g (85%) of the title compound.

$^1$H NMR (CDCl$_3$, since stereoisomers were present multiple peaks were observed and ppm ranges are given): 4.44 & 4.38 (2m, 1H), 3.70 & 3.69 (2s, 3H), 1.7–2.65 (m, 5H), 1.06 & 1.01 (2d, 3H, J=7 Hz), 0.97 (t, 3H, J=7 Hz).

Step B

5-Ethyl-4-methyl-2-pyrrolidone

A solution of 4.0 g (21 mmol) of methyl 3-methyl-4-nitrohexanoate (from step A) in 20 mL of EtOH containing 0.4 g of PtO2 was hydrogenated on a Parr apparatus for 3 days. The catalyst was filtered and washed with EtOH and the filtrate was concentrated. Vacuum distillation of the residue furnished 1.6 g (61%) of the title compound: bp 102°–107° C./2 mm.

$^1$H NMR (CDCl$_3$, since stereoisomers were present multiple peaks were observed and ppm ranges are given): 6.9 (br s, 1H), 3.50 & 3.11 (2 m, 1H), 1.3–2.65 (m, 5H), 1.14 & 1.04 (2d, 3H, J=7 Hz), 0.96 (t, 3H, J=7 Hz).

Step C 1-aza-5-ethyl-2-methoxy-4-methyl-1-cyclopentene

To a solution of 0.254 g (2 mmol) of 5-ethyl-4-methyl-2-pyrrolidone (from step B) in 3 mL of CH$_2$Cl$_2$ was added 0.355 g (2.4 mmol) of trimethyloxonium tetrafluoroborate under a N$_2$ atmosphere. After stirring overnight the reaction mixture was quenched with saturated K$_2$CO$_3$ solution and diluted with Et$_2$O. The solution was filtered and the filtrate was concentrated. The residue was purified by flash chromatography using Et$_2$O-hexane to isolate 0.224 g (79%) of the title compound.

$^1$H NMR (CDCl$_3$, since stereoisomers were present multiple peaks were observed and ppm ranges are given): 3.8 (s, 3H), 3.4–3.6 (m, 1H), 0.8–2.7 (m, 10H).

Step D

2-Imino-5-ethyl-4-methylpyrrolidine hydrochloride

A mixture of 0.1 g (0.71 mmol) in 3 mL of EtOH containing 0.03 g (0.56 mmol) of NH4Cl was heated to reflux. After 4 h the solution was cooled and concentrated and the residue was suspended in EtOAc. The precipitated solid was filtered washed with EtOAc and dried to furnish 0.072 g (79%) of the title compound.

$^1$H NMR (D$_2$O, since stereoisomers were present multiple peaks were observed and ppm ranges are given): 3.82 & 3.50 (2 q, 1H), 2.45–3.1 (m, 2H), 2.31 & 1.64 (2 m, 1H), 1.45–1.6 (m, 2H), 1.11 & 1.0 (2 d, 3H, J=7 Hz), 0.92 (t, 3H, J=7 Hz).

Mass spectrum m/e=127 (M+1)

The following 2-imino-pyrrolidines were prepared by the method of Example 6 by substituting appropriate nitroalkane and acrylate esters.

2-Imino-4-methylpyrrolidine hydrochloride (L-770,552)

$^1$H NMR (D$_2$O): 3.73 (t, 1H), 3.22 (dd, 1H), 2.97 (dd, 1H), 2.65 (m, 1H), 2.47 (dd, 1H), 1.08 (d, 3H).

Mass spectrum m/e=99 (M+1)

2-Imino-4-ethylpyrrolidine hydrochloride $^1$H NMR (D$_2$O): 3.75 (dd, 1H), 3.31 (dd, 1H), 2.98 (q, 1H), 2.54 (m, 2H), 1.49 (m, 2H), 0.89 (t, 3H).

Mass spectrum m/e=113 (M+1)

2-Imino-4,5-dimethylpyrrolidine hydrochloride $^1$H NMR (D$_2$O, since stereoisomers were present multiple peaks were observed and ppm ranges are given): 4.05 & 3.69 (2 m, 1H), 2.99 & 2.94 (2 dd, 1H), 2.66 & 2.17 (2m, 1H), 2.54 & 2.51 (2l, 1H), 1.25, 1.13, 1.1 & 0.99 (4d, 6H).

Mass spectrum m/e=113 (M+1)

2-Imino-4-methyl-5-propylpyrrolidine hydrochloride $^1$H NMR (D$_2$O, since stereoisomers were present multiple peaks were observed and ppm ranges are given): 3.69 & 3.30 (2 q, 1H), 1.95–2.6 (m, 3H), 1.2–1.6 ( m, 4H), 1.08 & 0.96 (2 d, 3H), 0.90 (t, 3H).

Mass spectrum m/e=142 (M+1)

2-Imino-5-methyl-4-propylpyrrolidine hydrochloride

Mass spectrum m/e=141 (M+1)

2-Imino-5-ethyl-4-propylpyrrolidine hydrochloride

Mass spectrum m/e=155 (M+1)

2-Imino-5-ethyl-3-methylpyrrolidine hydrochloride

Mass spectrum m/e=127 (M+1)

2-Imino-5,5-dimethylpyrrolidine hydrochloride $^1$H NMR (D$_2$O): 2.91 (t, 2H), 2.04 (t, 2H), 1.33 (s, 6H).

Mass spectrum m/e=113 (M+1)

2-Imino-3,5,5-trimethylpyrrolidine hydrochloride

Mass spectrum m/e=127 (M+1)

2-Imino-4-ethyl-5-methylpyrrolidine hydrochloride $^1$H NMR (D$_2$O, since stereoisomers were present, multiple peaks were observed and ppm ranges are given): 4.08 & 3.71 (2 m, 1H), 2.4–3.1 (m, 3H), 1.2–1.6 (m, 2H), 1.26 & 1.11 (2 d, 3H), 0.90 (t, 3H).

Mass spectrum m/e=127 (M+1)

2-Imino-4-propylpyrrolidine hydrochloride $^1$H NMR (D$_2$O): 3.74 (dd, 1H), 3.30 (dd, 1H), 2.97 (dd, 1H), 2.6 (m, 2H), 1.45 (q,2H), 1.31 (m, 2H), 0.88 (t, 3H).

Mass spectrum m/e=127 (M+1)

2-Imino-4-(2-methyl-ethyl)pyrrolidine hydrochloride $^1$H NMR (D$_2$O): 3.72 (t, 1H), 3.37 (dd, 1H), 2.91 (dd, 1H), 2.63 (dd, 1H), 2.39 (m, 1H), 1.66 (m, 1H), 0.88 (2d, 6H).

Mass spectrum m/e=127 (M+1)

2-Imino-4-phenylpyrrolidine hydrochloride $^1$H NMR (D$_2$O): 7.4 (m, 2H), 7.32 (m, 3H), 4.02 (dd, 1H), 3.82 (m, 1H), 3.62 (m, 1H), 3.25 (dd, 1H), 2.97 (dd, 1H).

Mass spectrum m/e=161 (M+1)

2-Imino-3,4-dimethylpyrrolidine hydrochloride $^1$H NMR (D$_2$O, since stereoisomers were present multiple peaks were observed and ppm ranges are given): 3.74 & 3.68 (2 dd, 1H), 3.25 & 3.19 (2 dd, 1H), 3.12 & 2.23 (2 m, 1H), 2.68 (m, 1H), 1.27 & 1.17 (2 d, 3H,), 1.12 & 1.0 (2 d, 3H).

Mass spectrum m/e=113 (M+1)

2-Imino-4-ethyl-3-methylpyrrolidine hydrochloride $^1$H NMR (D$_2$O, since stereoisomers were present, multiple peaks were observed and ppm ranges are given): 3.77 & 3.67 (2 t, 1H), 3.32 & 3.26 (2t, 1H), 1.6–3.1(m, 2H), 1.51 & 1.40 (2m, 2H), 1.29 & 1.17 (2 d, 3H,), 0.90 (m, 3H).

Mass spectrum m/e=127 (M+1)

2-Imino-5-methyl-4-propylpyrrolidine hydrochloride $^1$H NMR (D$_2$O, since stereoisomers were present, multiple peaks were observed and ppm ranges are given): 3.82 & 3.50 (2 q, 1H), 2.45–3.1 (m, 2H), 2.31 & 1.64 (2 m, 1H), 1.45–1.6 (m, 2H), 1.11 & 1.0 (2 d, 3H, J=7 Hz), 0.92 (t, 3H, J=7 Hz).

Mass spectrum m/e=127 (M+1)

2-Imino-3-azabicyclo(4.3.0)nonane hydrochloride $^1$H NMR (D$_2$O): 3.56 (dd, 1H), 3.32 (dd, 1H), 3.02 (q, 1H), 2.56 (q, 1H), 1.2–2.0 (m, 8H).

Mass spectrum m/e=139 (M+1)

2-Imino-3-azabicyclo(3.3.0)octane hydrochloride $^1$H NMR (D$_2$O): 3.82 (dd, 1H), 3.48 (dt, 1H), 3.32 (dd, 1H), 2.98 (m, 1H), 1.4–2.1 (m, 6H).

Mass spectrum m/e=125 (M+1)

The following compounds were synthesized from the commercially available pyrrolidone intermediates by the procedure outlined in step C and D in example 6.

2-Imino-3-methylpyrrolidine hydrochloride $^1$H NMR (D$_2$O): 9.48 (s, 1H), 9.1 (s, 1H), 8.82 (s, 1H), 3.6 (m, 1H), 3.28 (m, 1H), 2.37 (m, 1H), 1.78 (m, 1H), 1.40 (d, 3H).

2-Imino-5-methylpyrrolidine hydrochloride $^1$H NMR (D$_2$O): 9.49 (s, 1H), 9.18 (s, 1H), 8.79 (s, 1H), 4.05 (m, 1H), 3.02 (m, 1H), 2.92 (m, 1H), 2.33 (m, 1H), 1.73 (m, 1H), 1.32 (d, 3H).

EXAMPLE 7

2-Imino-5-(S)-acetyloxymethylpyrrolidine hydrochloride

The commercially available (S)-5-(hydroxymethyl)-2-pyrrolidone was acylated with acetic anhydride and the product was subjected to the procedure of Example 6, steps C and D to isolate the title compound.

$^1$H NMR (D$_2$O): 4.28 (m, 2H), 4.07 (m, 1H), 2.92 (m, 2H), 2.37 (m, 1H), 2.11 (s, 3H), 2.0 (m, 1H).

2-Imino-5-(R)-acetyloxymethylpyrrolidine hydrochloride

The title compound was prepared by the procedure of Example 7 starting from (R)-5-(hydroxymethyl)-2-pyrrolidone.

$^1$H NMR (D$_2$O): 4.3(m, 2H), 4.09 (q, 1H), 2.92 (m, 2H), 2.39 (m, 1H), 2.10 (s, 3H), 2.0 (m, 1H).

Mass spectrum m/e=157 (M+1)

EXAMPLE 8

2-Imino-5-(S)-hydroxymethylpyrrolidine hydrochloride

A solution of 15 mg (0.078 mmol) of 2-imino-5-(S)-acetyloxymethylpyrrolidine hydrochloride prepared in example 7 in 3 mL of methanol was saturated with NH3 and the solution was stirred for 3 h. The reaction mixture was concentrated and the residual solid was suspended in Et2O-EtOAc, filtered and washed with Et$_2$O and dried to isolate 6 mg of the title compound.

$^1$H NMR (D$_2$O): 4.10 (m, 1H), 3.70 (m, 1H), 3.57 (m, 1H), 2.87 (m, 2H), 2.29 (m,1H), 1.97 (m, 1H).

Mass spectrum m/e=115 (M+1)

2-Imino-5-(R)-hydroxymethylpyrrolidine hydrochloride

The title compound was obtained from 2-imino-5-(R)-acetyloxymethylpyrrolidine hydrochloride (Example 7) by the method above.

$^1$H NMR (D$_2$O): 4.12 (m, 1H), 3.72 (dd, 1H), 3.57 (dd, 1H), 2.88 (m, 2H), 2.3 (m, 1H), 1.96 (m, 1H).

Mass spectrum m/e=115 (M+1)

EXAMPLE 9

2-Imino-4(S)-methoxy-5(S)-methyl-piperidine, hydrochloride

STEP A

5-O-tert-Butyldimethylsilyl-2,3-dideoxy-D-glycero-pent-2-eno-1,4-lactone

To a solution of 2,3-dideoxy-D-glycero-pent-2-eno-1,4-lactone (580 mg, 5.08 mmol) in dry N,N-dimethylformamide (DMF) (7 mL) were added triethyamine (1.06 mL, 7.60 mmol) and 4-dimethylaminopyridine (63 mg, 0.51 mmol). The reaction mixture was cooled in an ice-bath, and tert-butyldimethylsilyl chloride (1.02 g, 6.77 mmol) was added. The mixture was allowed to attain room temperature and stirred an additional 3 hours. The mixture was then diluted with diethyl ether, washed with water, 2N hydrochloric acid, saturated sodium hydrogencarbonate solution, saturated brine solution, dried (Na$_2$SO$_4$), and evaporated. This procedure was repeated with 600 mg (5.26 mmol) of 2,3-dideoxy-D-glycero-pent-2-eno-1,4-lactone. The two runs were combined after workup, and the product was purified by flash silica gel chromatography eluting with 15% acetone in hexane. The resulting oil crystallized upon standing; yield 1.65 g (70%); $^1$H NMR (400 MHz, CDCl$_3$): δ0.03 (s, 3H), 0.05 (s, 3H), 0.85 (s, 9H), 3.78 (dd, 1H), 3.91 (dd, 1H), 5.03 (m, 1H), 6.14 (dd, 1H), 7.48 (dd, 1H).

STEP B 2,3-Dideoxy-3-C-methyl-5-O-tert-butyldimethylsilyl-D-erythro-pentono-1,4-lactone To a vigorously stirred suspension of copper(I) bromide-dimethyl sulfide complex (7.42 g, 36.1 mmol) in diethyl ether (80 mL) was added methyl lithium (51 mL of a 1.4M solution in hexane, 71.4 mmol) over 5–6 minutes. The resulting solution was cooled to –23° C. (CCl$_4$/dry ice bath), and a solution of 5-O-tert-butyldimethylsilyl-2,3-dideoxy-D-glycero-pent-2-eno-1,4-lactone (1.65 g, 7.22 mmol) was added in one portion. The suspension was stirred at –23° C. for 20 minutes and quenched by the cautious addition of saturated aqueous ammonium chloride (39 mL). The mixture was transferred to a separatory funnel and shaken vigorously to break down excess reagent. The organic layer was washed with saturated brine solution, dried (MgSO$_4$), and evaporated. The product was purified by flash silica gel chromatography eluting initially with 5% ethyl acetate in hexane and subsequently with 10% ethyl acetate in hexane; yield 1.42 g (80%); $^1$H NMR (400 MHz, CDCl$_3$): δ0.04 (s,3H), 0.06 (s, 3H), 0.88 (s, 9H), 1.16 (d, 3H), 2.11 (dd, 1H), 2.52 (m, 1H), 2.77 (m, 1H), 3.71 (dd, 1H), 3.82 (dd, 1H), 4.08 (m, 1H).

STEP C 2,3-Dideoxy-3-C-methyl-D-erythro-pentono-1,4-lactone 2,3-Dideoxy-3-C-methyl-5-O-tert-butyldimethylsilyl-D-erythro-pentono-1,4-lactone (1.4 g, 6.13 mmol) was treated with tetra-n-butylammonium fluoride (8.7 mL of a 1.0M solution in tetrahydrofuran, 8.7 mmol) for 90 minutes at room temperature. The reaction mixture was evaporated, and the crude product subjected to flash silica gel chromatography eluting initially with 15% acetone in hexane and subsequently with 25% acetone in hexane. Pure title compound was obtained as an oil; yield 710 mg (89%); $^1$H NMR (400 MHz, CDCl$_3$): δ1.16 (d, 3H), 2.21 (dd, 1H), 2.50 (m, 1H), 2.72 (dd, 1H).

STEP D

5-Azido-2,3,5-trideoxy-3-C-methyl-D-erythro-pentono-1,4-lactone

To a solution of 2,3-dideoxy-3-C-methyl-D-erythro-pentono-1,4-lactone (490 mg, 3.76 mmol) in methylene chloride (10 mL) cooled in an ice-bath were added 2,6-lutidine (501 mL, 4.30 mmol) and trifluoromethanesulfonic anhydride (682 mL, 4.05 mmol). The reaction mixture was stirred at 0° C. for 30 minutes, diluted with methylene chloride, washed with water, 2N hydrochloric acid, saturated sodium hydrogencarbonate solution, saturated brine solution, dried (Na$_2$SO$_4$), and evaporated. The crude product was taken up in DMF (6 mL) and treated with sodium azide (856 mg, 13.2 mmol) at room temperature for 30 minutes. The mixture was diluted with ethyl acetate, washed with water, dried (Na$_2$SO$_4$), and evaporated. The pure title compound was obtained after flash silica gel chromatography eluting with 25% ethyl acetate in hexane; yield 358 mg (61%); $^1$H NMR (400 MHz, CDCl$_3$): δ1.15 (d, 3H), 2.21 (dd, 1H), 2.42 (m, 1H), 2.74 (dd, 1H), 3.44 (dd, 1H), 3.60 (dd, 1H), 4.15 (m, 1H); mass spectrum: 128 (M+1–N$_2$).

STEP E

4(S)-Hydroxy-5(S)-methyl-2-piperidone

A solution of 5-azido-2,3,5-trideoxy-3-C-methyl-D-erythro-pentono-1,4-lactone (358 mg, 2.31 mmol) in methanol (4 mL) was hydrogenated under a balloon atmosphere of hydrogen gas in the presence of 10% palladium-on-charcoal (50 mg) overnight at room temperature. The catalyst was then removed by filtration through Celite, and the filter washed with methanol. The combined filtrate and washings were evaporated, and the resulting product crystallized upon standing; yield 128 mg (43%); $^1$H NMR (400 MHz, CDCl$_3$): δ1.03 (d, 3H), 2.05 (m, 1H), 2.17–2.28 (m, 2H), 3.27 (dd, 1H), 3.40 (dd, 1H), 3.86 (m, 1H); mass spectrum: 130 (M+1).

STEP F

2-Imino-4(S)-methoxy-5(S)-methyl-piperidine, hydrochloride.

To a solution of 4(S)-hydroxy-5(S)-methyl-2-piperidone (119 mg, 0.921 mmol) in methylene chloride (3 mL) was added trimethyloxonium tetrafluoroborate (285 mg, 1.93 mmol). The reaction mixture was stirred for 24 hours at room temperature. Thin-layer chromatography (10% MeOH/CH$_2$Cl$_2$) indicated the formation of two more mobile products: the 4-methoxy-5-methyl imino-methyl ether and the 4-hydroxy-5-methyl imino-methyl ether. The mixture was diluted with ethyl acetate, washed with saturated sodium hydrogencarbonate solution, saturated brine solution, dried (MgSO$_4$), and carefully evaporated (bath temperature <15° C.) to avoid loss of the volatile imino ethers. The crude product mixture in ethyl acetate was applied to a column of silica gel (packed as a slurry in 4% methanol/CH$_2$Cl$_2$). Rapid elution with 4% methanol/CH$_2$Cl$_2$ afforded the 4-methoxy-5-methyl imino-methyl ether (yield ~16.7 mg), and subsequent elution with 10% MeOH/CH$_2$Cl$_2$ afforded the 4-hydroxy-5-methyl imino-methyl ether (yield ~13.6 mg). Evaporations of the column fractions containing product was performed with extreme caution to avoid loss of the volatile imino ethers.

The 4-methoxy-5-methyl imino-methyl ether (~16.7 mg) was treated with ammonium chloride (4.5 mg) for 4 hours at reflux temperature. The reaction mixture was evaporated, and the resulting solid dried in vacuo; yield 14.3 mg; $^1$H NMR (400 MHz, CDCl$_3$): δ1.10 (d, 3H), 2.12 (m, 1H), 2.40 (dd, 1H), 2.53 (dd, 1H), 3.40 (s, 3H), 3.52 (m, 1H), 3.67 (dd, 1H); mass spectrum: 143 (M+1).

EXAMPLE 10

2-Imino-5(S)-hydroxy-4(S)-methyl-piperidine, hydrochloride

The 4-hydroxy-5-methyl-imino methyl ether from Step 6 of Example 6 (~13.6 mg) was treated with ammonium chloride ((4.4 mg) for 4 hours at reflux temperature. The reaction mixture was evaporated, and resulting solid dried in vacuo; yield 9.5 mg; $^1$H NMR (400 MHz, CDCl$_3$): δ1.10 (d, 3H), 2.08 (m, 1H) ,2.47 (dd, 1H), 2.55 (dd, 1H), 3.40 (dd, 1H), 3.50 (dd, 1H), 3.93 (m, 1H); mass spectrum: 129 (M+1).

EXAMPLE 11

4(S),5(R)-Dimethyl-2-imino-piperidine hydrochloride

Step A (S)-Citronelloyl chloride

Oxalyl chloride (8.1 mL, 92 mmol) of was added to 14.4 g (83.75 mmol) of (S)-Citronellic acid in 150 mL of methylene chloride at 0° C. 12.9 mL (92 mmol) of triethylamine was then added dropwise cautiously so that the gases evolved can be vented effectively. After the addition was comlete, the mixture was stirred 1 hour at the same temperature. After dilution with 300 mL of ether, the solids precipitated were filtered and washed with ether. The filtrate was concentrated to give a brown liquid. This was dissolved in ether and the small amount of solid was filtered and washed with ether. The filtrate was concentrated in vacuo to give almost quantitative yield of the desired acid chloride as brown oil.

$^1$H NMR (CDCl$_3$): 1.0(d, 3H); 1.58(s,3H); 1.68(s,3H); 2.66 & 2.88(2q; 2H); 5.05(t,1H)

Step B

3(3(S),7-Dimethyl-6-octenoyl)-4(R)-phenylmethyl-2-oxazolidinone

A 1.6M solution of n-butyllithium (52 mL, 83 mmol) was added dropwise to a solution of 4(R)-phenylmethyl-2-oxazolidinone (13.3 g, 75 mmol) in 150 mL of THF at –78° C. The reaction mixture was stirred for 15 min after the addition and a solution of the above S-citronelloyl chloride in 50 mL of THF was added dropwise and the mixture was stirred for 15 min at that temperature. The cooling bath was removed and the mixture was allowed to warm to room temperature and stirred 1 hr at room temperature. After quenching with saturated ammonium chloride solution, the reaction mixture was partitioned between 1N hydrochloric acid and ethyl acetate. The ethyl acetate extracts were washed with saturated sodium chloride solution and dried over anhydrous magnesium sulfate. Solvent removal gave an oil which was chromatographed on silica gel using 10% ethyl acetate in hexane as solvent to give the title compound in 65% yield.

$^1$H NMR (CDCl$_3$): 1.0(d,3H); 1.6(s,3H); 1.66(s,3H); 2.74(q,1H); 2.85(m;2H); 3.3(q,1H); 4.15(m,2H); 4.66(m, 1H); 5.08(t,1H); 7.28(m,5H)

Step C

3(2(R),3(S),7-Trimethyl-6-octenoyl)-4(R)-phenylmethyl-2-oxazolidinone 55 mL (55 mmol) of 1M solution of sodium bis(trimethylsilyl)amide in THF was added dropwise to a solution of 15 g (45.4 mmol) of 3(3(S),7-dimethyl-6-octenoyl)-4(R)-phenylmethyl-2-oxazolidinone in 120 mL of THF at –78° C. The reaction mixture was stirred 30 mins at that temperature and 21 mL (333 mmol) of methyl iodide in 20 mL of THF was added dropwise. The resulting mixture was stirred 1 day at –78° C. After warming to room temperature, the reaction mixture was quenched with ammonium chloride solution and partitioned between 1N hydrochloric acid and ethyl acetate. The ethyl acetate extracts were washed with sodium thiosulfate solution, saturated sodium bicarbonate solution, brine and dried over anhydrous magnesium sulfate. Solvent removal afforded essentially pure desired methylated oxazolidinone derivative in quantitative yield.

$^1$H NMR (CDCl$_3$): 0.88(d, 2H); 1.13(d,3H); 1.58(s,3H); 1.66(s,3H); 2.75(q,1H); 3.26(q,1H); 3.68(m,1H); 4.15(m, 2H); 4.63(m,1H); 5.08(t,1H)7.25(m,5H)

Step D

2(R),3(S),7-Trimethyl-6-octen-1-ol

A solution of 6.8 g (20 mmol) of 3(2(R),3(S),7-trimethyl-6-octenoyl)-4(R)-phenylmethyl-2-oxazolidinone in 30 mL of THF was added dropwise to a suspension of 1.634 g (43 mmol) of lithium aluminum hydride in 40 mL of THF at 0° C. The reaction mixture was then stirred 6 h at ambient temperature The reaction mixture was then recooled in ice bath and 5 mL of methanol was added dropwise very cautiously. After the effervescence subsided, the reaction mixture was concentrated to about 30% of the original volume The reaction mixture was then stirred with saturated solution of potassium sodium tartrate and extracted with ethyl acetate. The combined ethyl acetate extracts were dried over anhydrous magnesium sulfate. Solvent removal afforded a crude oil, which was purified on silica gel using 10% ethyl acetate in hexane as solvent to give 2.0 g (62%) of the desired alcohol as a colorless oil.

$^1$H NMR (CDCl$_3$): 0.78(d, 2H); 0.79(d,2H); 1.6(s,3H); 1.66(s,3H); 3.44(q,1H); 3.54(q,1H); 5.1(t,1H)

Step E

2(R),3(S),7-Trimethyl-6-octen-1-methanesulfonate

To a solution of 510 mg (3 mmol) of 2(R),3(S),7-trimethyl-6-octen-1-ol in 3 mL of pyridine at ice bath temperature 0.7 mL (9 mmol) of methanesulfonyl chloride was dropwise added. The mixture was then stirred for 8 hrs at room temperature. After diluting with ethyl acetate, the reaction mixture was washed with saturated sodium bicarbonate, 1N citric acid and water. After drying over anhydrous magnesium sulfate, the solvent was removed to give 722 mg of the desired mesylate as a yellow oil.

$^1$H NMR (CDCl$_3$): 0.8(d,3H); 0.87(d,3H); 1.6(s,3H); 1.67(s,3H); 2.98(s,3H); 4.02(q,1H); 4.13(q,1H); 5.06(t,1H)

Step F

2(R),3(S),7-Trimethyl-1-azido-6-octene 975 mg (15 mmol) of sodium azide was added to a solution of 2(R),3(S),7-trimethyl-6-octen-1-methane sulfonate (720 mg, ~3 mmol) in 6 mL of N,N-dimethylformamide and the mixture was heated overnight at 80° C. The reaction mixture was diluted with ethyl acetate and washed several times with saturated sodium chloride solution. After drying over anhydrous magnesium sulfate, the solvents were removed in vacuo to give crude azide as an oil. This material was purified on silica gel using 30% ether in hexane as solvent to give 545 mg of the desired azide as a colorless oil.

$^1$H NMR (CDCl$_3$): 0.78(d,3H); 0.84(d,3H); 1.59(s,3H); 1.66(s,3H); 3.1(q,1H); 3.21(q,3H); 5.07(t,1H)

Step G

2(R),3(S),7-Trimethyl-1-amino-6-octene 6.3 mL (6.3 mmol) of 1M lithium aluminum hydride in THF was added dropwise to a solution of 2(R),3(S),7-trimethyl-1-azido-6-octene in 10 mL of THF at 0° C. The reaction mixture was heated to reflux 18 hrs. After cooling in ice bath, ~1 mL of methanol was added dropwise cautiously. After the effervescence stopped, the reaction mixture was concentrated to 30% of the volume and 1N solution of potassium sodium tartrate was added. After stirring 15 mins, the reaction mixture was extracted with ethyl acetate. The combined ethyl acetate layers were dried over anhydrous magnesium sulfate and the solvent was removed to give 399 mg of the desired amine as an oil.

$^1$H NMR (CDCl$_3$): 0.76(d,3H); 0.78(d,3H); 1.60(s,3H); 1.67(s,3H); 2.49(q.1H); 2.62(q,1H); 5.1(t,1H)

Step H

2(R),3(S),7-Trimethyl-1-benzyloxycarbonylamino-6-octene

Separate solutions of 2(R),3(S),7-trimethyl-1-amino-6-octene (0.87 g, 5.2 mmol) in 8 mL of dioxane, and benzyl chloroformate (0.86 mL, ~6 mmol) in 8 mL of dioxane were added dropwise simultaneously to a stirred solution of 1.05 g (10.5 mmol) of potassium hydrogen carbonate in 20 mL of water at 0° C. After the additions, the mixture was stirred 8 hrs at room temperature. Most of the volatile solvents were removed in vacuo. The remaining reaction mixture was extracted with ethyl acetate. The combined organic phases were dried over anhydrous magnesium sulfate. Solvent removal gave the crude product which was purified on silica gel using 10% ethyl acetate in hexane as solvent to give 1.4 g of the desired carbamate as a colorless oil.

$^1$H NMR (CDCl$_3$): 0.77(d,6H); 1.18(m,1H); 1.3(m,1H); 1.5(m,1H); 1.6(s,3H); 1.66(s,3H); 1.95(m,2H); 3.04(m,1H); 1.12(m,1H); 4.7(b,1H); 5.08(s & m,3H)7.34(m,5H)

Step I

4(S),5(R)-Dimethyl-6-benzyloxycarbonylamino-hexan-1-al

A stream of 4% ozone in oxygen was bubbled through a solution of 1.79 g (~6 mmol) of 2(R),3(S),7-trimethyl-1-benzyloxycarbonylamino-6-octene in 25 mL of methylene chloride at -78° C. until blue color persisted. Nitrogen gas was bubbled through the reaction mixture at the same temperature for 15 min. 3 mL of dimethyl sulfide was added and the mixture was stirred 15 mins and then warmed to 0° C. The solvents and other volatile materials were removed under house vacuum. Traces of solvent were then removed in vacuo to give 1.3 g of the desired aldehyde as a thick oil.

$^1$H NMR (CDCl$_3$): 0.8(2d,6H); 1.48 & 1.54(m,4H); 2.42(m,2H); 3.04(m,1H); 3.14(m,1H); 5.08(s,2H); 7.34(m, 5H); 9.74(s,1H)

Step J

3(R),4(S)-Dimethyl-1-benzyloxycarbonyl-2,3,4,5-tetrahydroazepine

A mixture of 1.2 g (~4.2 mmol) of 4(S),5(R)-dimethyl-6-benzyloxycarbonylamino-hexan-1-al, 1.26 mL (13.2 mmol) of acetic anhydride and 120 mg (1.2 mmol) of potassium acetate was heated at 160° C. for 2 hours. Excess acetic anhydride was removed in vacuo and the residue was purified on silica gel using 20% ethyl acetate in hexane as solvent to give ~190 mg of the desired azepine derivative as an oil.

$^1$H NMR (CDCl$_3$): 0.95 & 1.0 (2d,6H); 2.0(m,1H); 2.17(m,1H); 3.64(m,1H); 3.74(m,1H); 4.9(m,1H); 5.1(s, 2H); 6.6(m,1H); 7.35(m,1H)

Step K

3(S),4(R)-Dimethyl-6-(benzyloxycarbonyl)formimido-1-pentanoic acid

A stream of 4% ozone in oxygen was bubbled through a solution of 130 mg (0.5 mmol) of 3(R),4(S)-dimethyl-1-benzyloxycarbonyl-2,3,4,5-tetrahydroazepine in 5 mL of glacial acetic acid at room temperature for 10 mins. 0.3 mL of 30% hydrogen peroxide was added and the mixture was heated to reflux 2 hrs. The solvent was removed and the traces were azeotroped with toluene to give 100 mg of the desired acid as a thick oil.

$^1$H NMR (CDCl$_3$): 0.76(d,3H); 0.87(d,3H); 1.9(m,1H); 2.0(m,1H); 2.18(q,1H); 2.32(q,1H); 3.5(q,1H); 3.6(q,1H); 5.28(s,2H); 7.37(m,5H); 9.26(s,1H)

Step L

3(S),4(R)-Dimethyl-6-benzyloxycarbonylamino-1-pentanoic acid

A solution of 2N sodium hydroxide (0.4 mL, 0.8 mmol) was added to a solution of 90 mg (0.3 mmol) of 3(S),4(R)-dimethyl-6-(benzyloxycarbonyl)formamido-1-pentanoic acid in a mixture of 2 mL of methanol and 1 mL of water. This mixture was heated 2 hrs at 60° C. The reaction mixture was cooled and 0.4 mL of 2N hydrochloric acid was added. Solvents were removed and the residue was extracted with ethyl acetate. The organic layer was dried over anhydrous magnesium sulfate and the solvent removal afforded 62 mg of the desired acid as an oil.

$^1$H NMR (CDCl$_3$): 0.82(d,3H); 0.88(d,3H); 1.68(m,1H); 2.08(m,1H); 2.2(m.1H); 2.35(m,1H); 3.1(m,2H); 5.1(2H); 7.3(m,5H)

Step M

4(S),5(R)-Dimethyl-2-piperidone

Ethyl chloroformate (0.048 mL, 0.5 mmol) was added to a solution of 3(S),4(R)-dimethyl-6-benzyloxycarbonylamino-1-pentanoic acid (62 mg, 0.25 mmol) and triethylamine (0.07 mL, 0.5 mmol) in 2 mL of ethyl acetate cooled in ice bath. After stirring 1 hr, the solids were filtered and washed with ethyl acetate. The filtrate was concentrated to give the carbonate as oil. 2 mL of toluene was added to this residue and heated to reflux 5 hrs. The solvent was then removed in vacuo to give the N-protected lactam as oil. 25 mg of palladium hydroxide was added to a solution of the above residue in 2 mL of methanol and the mixture was hydrogenated 4 hrs on a Parr shaker. The catalyst was filtered and washed with methanol. The filtrate was concentrated to give 31 mg of the desired lactam as a waxy solid.

$^1$H NMR (CDCl$_3$): 0.95(d,3H); 0.97(d,3H); 1.54(m,2H); 1.98(m,1H); 2.44(m,1H); 2.9(m,1H); 3.25(m,1H).

Step N

4(S),5(R)-Dimethyl-2-iminopiperidine hydrochloride

The title compound was prepared from 4(S),5(R)-Dimethyl-2-piperidone according to the procedure described in Example 2 steps A and B.

$^1$H NMR (DMSO): 0.89(d,3H); 0.93(d,3H); 1.50(m,2H); 2.20(m,1H); 2.55(m,1H); 2.83(m,1H); 8.3(b,1H); 8.65(b, 1H); 9.40(b,1H)

EXAMPLE 12

4(R),5(S)-Dimethyl-2-imino-piperidine hydrochloride

The title compound is prepared according to the procedure of Example 11 starting with (R)-citronellic acid and 4(S)-phenylmethyl-2-oxazolidinone.

EXAMPLE 13

4(S),5(S)-Dimethyl-2-imino-piperidine hydrochloride

The title compound is prepared according to the procedure of Example 11 starting with (S)-citronellic acid and 4(S)-phenylmethyl-2-oxazolidinone.

EXAMPLE 14

4(R),5(R)-Dimethyl-2-imino-piperidine hydrochloride

The title compound is prepared according to the procedure of Example 11 starting with (R)-citronellic acid and 4(R)-phenylmethyl-2-oxazolidinone.

EXAMPLE 15 cis-Decahydro-2-iminoquinoline hydrochloride

Step A cis-Decahydro-2-quinolinone

A suspension of 1 g of 3,4,5,6,7,8-hexahydro-2(1H)-quinolinone in 1:1 mixture of dioxane and ethanol was hydrogenated in presence of 250 mg of 10% palladium on carbon at 60 psi and room temperature for 4 hours. The catalyst was filtered on a bed of filter cell and washed with dioxane-ethanol mixture. The filtrate was concentrated to give a residue which was purified on silica gel using ethyl acetate as solvent to give 510 mg of the desired product containing about 10% trans-isomer. Recrystallization from hexane did not improve the isomer ratio.

$^1$H NMR (CDCl$_3$): 3.49(m,1H); 2.33(m,2H)1.2–2.0(m, 11H)

Step B cis-Decahydro-2-iminoquinoline hydrochloride

The title compound was synthesized as described in Example 2 from cis-decahydro-2-quinolinone.

$^1$H NMR (DMSO): 3.49(m,1H); 2.53(m,2H); 1.25–2.0(m, 11H); 8.16(b,1H); 8.7(b,1H); 9.65(b,1H)

EXAMPLE 16 cis-2-Imino-4-methyl-decahydroquinoline hydrochloride

Step A

4-Methyl-decahydro-cis-quinolin-2-one

A mixture of 2 g (12.5 mmol) of 2-hydroxy-4-methylquinoline in 25 mL of acetic acid containing 1 g of PtO2 was hydrogenated on a Parr apparatus for 36 h. The catalyst was filtered through celite and washed with acetic acid and the combined filtrate was concentrated. The residue was triturated with Et2O and the solid formed was filtered and dried to isolate 1.2 g (57%) of the title compound.

$^1$H NMR (CDCl$_3$): 0.94 (d, 3H), 1.1–2.35 (m, 12H), 3.6 (m, 1H), 5.68 (br s, 1H).

Step B cis-2-Imino-4-methyl-decahydroquinoline hydrochloride

The title compound was prepared from 4-methyl-decahydro-cis-quinolin-2-one by the method of example 2.

$^1$H NMR (DMSO): 0.94 (d, 3H), 1.1–2.5 (m, 12H), 3.60 (m, 1H), 8.1 (br s, 1H), 8.75 (br s, 1H), 9.65 (br s, 1H)

EXAMPLE 17 trans-Decahydro-2-iminoquinoline hydrochloride

Step A trans-Decahydro-2-quinolinone

A mixture of 1 g (6.62 mmol) of 3,4,5,6,7,8,-hexahydro-2(1H)-quinolinone, 2.8 g (41 mmol) of sodium formate and 5 mL of formic acid was heated to reflux for 1 day The reaction mixture was then cooled and 20% sodium hydroxide solution was added to make it basic. This mixture was then extracted with ethyl acetate. The combined ethyl acetate extracts were dried over anhydrous magnesium sulfate and the solvent was removed to give a crude product. This was purified on silica gel using ethyl acetate as solvent to provide 752 mg of the desired product with about 10% of the cis-isomer. Recrystallization of this material from cyclohexane did not improve the ratio of the isomers.

$^1$H NMR (CDCl$_3$): 2.88(m,1H); 2.4(m,2H)1.0–1.9(m, 11H)

Step B trans-Decahydro-2-iminoquinoline hydrochloride

The title compound was synthesized from trans-decahydro-2-quinolinone as described in example 2 steps A and B.

$^1$H NMR (DMSO): 2.95(m,1H); 2.58(m,2H); 1.0–2.0(m, 11H); 8.12(b,1H); 8.76(b,1H); 9.70(b,1H)

EXAMPLE 18

4(R)-Methyl-2-iminopiperidine hydrochloride

Step A

Methyl (R)-citronellate

Diazomethane in ether was cautiously added to a solution of (R)-citronellic acid (17.2 g, 0.1M) in ether at 0° C. until yellow color persisted. After the addition was complete, the reaction mixture was stirred 30 mins and the solvent was removed in vacuo to give the quantitative yield of the desired methyl ester as a colorless oil.

$^1$H NMR (CDCl$_3$): 0.92(d,3H); 1.2(m,1H); 1.32(m,1H); 1.58(s,3H); 1.65(s,3H); 1.95(m,2H); 2.1(q,1H); 2.4(q,1H); 3.64(s,3H); 5.06(t,1H)

Step B

Methyl 3(R)-methyl-5-hydroxycarbonylpentanoate

A stream of 4% ozone in oxygen was passed through a solution of methyl (R)-citronellate (7 g, 39 mmol) in 140 mL of glacial acetic acid at room temperature for 45 mins. 14 mL of 30% hydrogen peroxide was then added and the reaction mixture was heated to reflux 2 hrs. Solvent was removed in vacuo to afford 6.5 g of the desired acid as a colorless oil.

$^1$H NMR (CDCl$_3$): 0.94(d,3H); 1.52(m,1H); 1.69(m,1H); 1.98(m,1H); 2.15(q,1H); 2.3(q,1H); 2.36(m,2H)

Step C

Methyl 3(R)-methyl-5-benzyloxycarbonylamino pentanoate

Diphenyl phosphoryl azide (5.3 mL, 24.53 mmol) was added to a mixture of methyl 3(R)-methyl-5-hydroxycarbonyl pentanoate (3.88 g, 22.3 mmol) and triethylamine (3.45 mL, 24.53 mmol) in 22 mL of p-xylene. The mixture was then stirred 1 hr at 80° C. 4.5 mL (45 mmol) of benzyl alcohol was then added and the mixture was heated at reflux for 4 hr. The reaction mixture was cooled, diluted with ethyl acetate and washed with water, and sodium chloride and dried over ahydrous magnesium sulfate. Solvent removal gave a crude product, which was purified on silica gel using 10% ethyl acetate in hexane as solvent to afford 3.9 g of the desired carbamate as an oil.

$^1$H NMR (CDCl$_3$): 0.95(d,3H); 1.4(m,1H); 1.62(m,1H); 2.02(m,1H); 2.18(q,1H); 2.3(q,1H); 3.22(m,2H); 3.65(s, 3H); 5.07(s,2H); 7.3(m,5H)

Step D

3(R)-Methyl-5-benzyloxycarbonylamino pentanoic acid

A 2N sodium hydroxide (7.5 ml, 15 mmol) solution was added to 3.9 g (14 mmol) of methyl 3R-methyl-5-benzyloxycarbonylamino pentanoate in 70 mL of 2:1 mixture of methanol:water. This mixture was then heated 1 hr at 60° C. and 7.5 mL of 2N hydrochloric acid was added after cooling. Most of the volatiles were removed in vacuo. The remaining mixture was extracted with ethyl acetate. The combined ethyl acetate extracts were dried over anhydrous magnesium sulfate. Solvent removal afforded 2.9 g of the desired acid as an oil.

$^1$H NMR (CDCl$_3$): 0.98 (d,3H); 1.42(m,1H); 1.56(m,1H); 2.02(m,1H); 2.2(m,1H); 2.35(m,1H); 3.2(m,2H); 5.08(s, 2H); 7.3(m,5H)

Step E

4(R)-Methyl-1-benzyloxycarbonyl-2-piperidone

Ethyl chloroformate (1.92 mL, 20 mmol) was added dropwise to a solution of 3(R)-methyl-5-benzyloxycarbonylamino pentanoic acid (2.65 g, 10 mmol) and triethyl amine (2.8 mL, 20 mmol) in 50 mL of ethyl acetate at 0° C. After stirring 1 hr at room temperature, the solids formed were filtered and washed with ethyl acetate. The filtrate was concentrated to give an oil which was taken up in 45 mL of toluene. This solution was heated to reflux for 4 hr. Solvent was then removed in vacuo and the residue was purified on silica gel using 20% ethyl acetate in hexane as solvent to give 1.39 g of the desired lactam as an oil.

$^1$H NMR (CDCl$_3$): 1.02(d,3H); 1.44(m,1H); 2.0(m,3H); 3.62(q,1H); 3.55(q,1H); 3.88(q,1H); 5.28(2H); 7.35(m,5H)

Step F

4(R)-Methyl-2-piperidone 10% Palladium hydroxide on carbon (350 mg) was added to a solution of 4(R)-Methyl-1-benzyloxycarbonyl-2-piperidone (1.3 g) in 20 mL of methanol and the mixture was hydrogenated on Parr shaker at 50 psi and room temperature. After 4 hrs, the catalyst was filtered and washed with methanol. The filtrate was concentrated to give 700 mg of the crude product which was purified on silica gel using 5% methanol in ethyl acetate as solvent to give 510 mg of the desired lactam as a white solid.

$^1$H NMR (DMSO): 0.92 (d,3H); 1.26 (m,1H); 1.75(m, 3H); 2.18(q,1H); 3.12 (m,2H)

Step G

4(R)-Methyl-2-imino piperidine hydrochloride

The title compound was prepared from 4R-methyl-2-piperidone as described in steps A and B of Example 2.

$^1$H NMR (DMSO): 0.96(d,3H); 1.25(m,1H); 1.75(m,1H); 1.85(m,1H); 2.15(q,1H); 2.55(q,1H0; 3.24(m,1H); 3.34(m, 1H); 8.28(b,1H); 8.62(b,1H); 9.35(b,1H)

EXAMPLE 19

4(S)-Methyl-2-iminopiperidine hydrochloride

The title compound was synthesized according to the procedure of Example 18 starting with (S)-citronellic acid.

EXAMPLE 20

5(R)-Methyl-2-iminopiperidine hydrochloride

Step A

2(R),6-Dimethyl-1-benzyloxycarbonylamino-5-heptene

Diphenylphosphoryl azide (14 mL, 65 mmol) was added dropwise to a solution of (R)-citronellic acid (10 g, 59 mmol) and triethylamine (9.1 mL, 65mmol) in 60 mL of toluene. The mixture was heated for 1 hr at 80° C. 12 mL (120 mmol) of benzyl alcohol was added and the mixture was heated to reflux for 4 hrs. The reaction mixture was cooled, diluted with ethyl acetate and washed with water, saturated sodium chloride solution. After drying over anhydrous magnesium sulfate, the solvent was removed in vacuo to give a crude product which was purified on silica gel using 5% ethyl acetate in hexane as solvent to afford 9.8 g of the desired carbamate as a thick oil.

$^1$H NMR (CDCl$_3$): 0.89(d,3H); 1.13(m,1H); 1.35(m,1H); 1.5(m,1H); 1.6(m,1H); 1.58(s,3H); 1.66(s,3H); 1.98(m,1H); 3.0(m,1H); 3.14(m,1H); 5.06(m,1H); 5.08(s,2H); 7.35(m, 5H)

Step B

5(R)-Methyl-1-benzyloxycarbonyl-2-piperidone

Ozone in oxygen (4%) was passed through a solution of 2-(R),6-dimethyl-1-benzyloxycarbonylamino-5-heptene (9.8 g) in 150 mL of methylene chloride at –78° C. until the blue color persisted. Nitrogen was then bubbled for 15 mins. 16 mL of dimethyl sulfide was added and the mixture was stirred 1 hr as it warmed to room temperature and then concentrated to give a residual oil. This was taken up in 100 mL of acetone and cooled in ice bath. Jones reagent was added dropwise until orange color was sustained. After stirring 30 mis, 4 mL of isoprpopyl alcohol was added and the mixture was stirred for an additional 15 mins. Solvent was then removed in vacuo and the residue was stirred with water and ethyl acetate. The organic phase was separated and the aqueous phase was extracted with ethyl acetate. The combined ethyl acetate extracts were dried over anhydrous magnesium sulfate and the solvent was removed in vacuo. The resulting residue was purified on silica gel using first 10% ethyl acetate in hexane as solvent to give 2.0 g of 5(R)-methyl-1-benzyloxycarbonyl-2-piperidone as an oil.

$^1$H NMR (CDCl$_3$): 1.02(d,3H); 1.45(m,1H); 1.87(m,1H); 1.94(m,1H); 2.54(m,2H); 3.16(q,1H); 3.88(q,1H); 5.26(s, 2H); 7.36(m,5H)

Further elution of the column with 1% methanol in ethyl acetate gave 5.8 g of 3(R)-methyl-N-(benzyloxycarbonyl)-N-formyl-4-aminobutanoic acid as a thick oil, which can be utilized in the synthesis of 4-(R)-2-imino-4-methylpyrrolidne.

Step C

5(R)-Methyl-2-piperidone

10% Palladium hydroxide on carbon (700 mg) was added to a solution of 4(R)-methyl-1-benzyloxycarbonyl-2-piperidone (2.0 g) in 40 mL of methanol and the mixture was hydrogenated on Parr shaker at 50 psi and room temperature. After 4 hrs, the catalyst was filtered and washed with methanol. The filtrate was concentrated to give 1.4 g of the crude product, which was purified on silica gel using 5% methanol in ethyl acetate as solvent to give 1 g of the desired lactam as a white solid.

$^1$H NMR (CDCl$_3$): 1.0(d,3H); 1.45(m,1H); 2.86(m,2H); 2.38(m,2H); 2.9(q,1H); 3.3(q,1H)6.6(b,1H)

Step D

5(R)-Methyl-2-iminopiperidine hydrochloride

The title compound was synthesized from 5(R)-methyl-2-piperidone according to the procedure described in Example 2.

$^1$H NMR (DMSO): 0.93(d,3H); 1.34(m,1H); 1.76(m,2H); 2.54(q,2H); 2.8(q,1H); 3.32(m,1H); 8.35(b,1H); 8.68(b,1H); 9.42(b,1H).

EXAMPLE 21

5(S)-Methyl-2-iminopiperidine hydrochloride

The title compound was prepared by the method of example 20 starting with (S)-citronellic acid.

EXAMPLE 22

3-Iminothiomorpholine hydrochloride

Step A

Thiomorpholin-3-one

To 6.5 g (0.15 mol) of ethyleneimine was added to 12 g (0.1 mol) of ethyl thiol acetate with stirring at 60° C. After the addition, the mixture was heated 2.5 hrs at the same temperature. It was then allowed to cool to room temperature and then allowed to stand 1 day at room temperature. Robust white crystals formed. The liquid was decanted and the solid was washed with ice cold ethyl alcohol to afford 6.2 g of the desired thiomorpholinone.

$^1$H NMR (CDCl$_3$): 2.8(m,2H); 3.28(s,2H); 3.62(m,2H); 6.62(b,1H)

Step B

Thiomorpholin-3-thione

A mixture of 1.17 g (10 mmol) of thiomorpholin-3-one and 11 mmoles of Lawesson's reagent in 25 mL of toluene was heated to reflux 2 hrs. The reaction mixture was cooled and the solvent was removed to give a residue. This was taken up in methylene chloride and applied on silica gel column and eluted with ethyl acetate containing methylene chloride (10%). The desired thiomorpholin-3-thione in 65% yield as a solid.

$^1$H NMR (CDCl$_3$): 2.90(m,2H); 3.62(m,2H); 3.76(s,2H); 8.65(b,1H)

Step C

3-Iminothiomorpholine hydrochloride

The title amidine was prepared from thiomorpholin-3-thione according to the procedure of example 3 step F.

$^1$H NMR (DMSO): 2.92(m,2H); 3.52(m,2H); 3.62(s,2H); 8.85(b,1H); 9.28(b,1H); 9.9(b,1H)

EXAMPLE 23

2-Iminopiperazine hydrochloride

Step A

2-Ketopiperazine

A solution of 10.2 g (81 mmol) of ethyl chloroacetate in 50 mL of ethanol was added dropwise over 1 hr to a solution of 30 g (0.5M) of ethylene diamine in 125 mL of ethanol at room temperature. The mixture was stirred 3 hrs and 4.4 g (81 mmol) of sodium methoxide was added and the mixture was stirred additional 4 hours. The resulting voluminous white precipitate was filtered and the filtrate was concentrated to give oily residue which was heated at 200° C. (bath temperature) for 5 mins with a wide distillation head. A solid deposited in the distillation head during the distillation. After 1.5 hrs of distillation, distillation head was washed with methanol to remove the desired product. Methanol washes were concentrated to give a crude product which was purified on silica gel using 5:2 mixture of chloroform:methanol as solvent to provide 2.3 g of the desired product as a yellow solid.

$^1$H NMR (DMSO): 2.74(m,2H); 3.1(m,2H); 3.13(s,2H); 7.58(b,1H)

Step B 4-t-Butoxycarbonyl-2-ketopiperazine

A mixture of 500 mg (5 mmol) of piperazinone, 1.2 g (5.5 mmol) of t-butyldicarbonate and 2 g of sodium chloride in 7.5 mL of water and 10 mL of chloroform was heated to reflux 4 hrs. The reaction mixture was cooled to room temperature and extracted with ethyl acetate. The combined ethyl acetate extracts were dried over anhydrous magnesium sulfate. Solvent removal gave a crude product which was purified on silica gel using 5% methanol in ethyl acetate as solvent to give 925 mg of the desired carbamate lactam as white solid.

$^1$H NMR (CDCl$_3$): 1.46(s,9H); 3.37(m,2H); 3.62(m,2H); 4.08(s,2H)

Step C 4-t-Butoxycarbonyl-2-iminopiperazine hydrochloride

The title compound was prepared according to the procedure described in Example 2.

$^1$H NMR (DMSO): 1.42(s,9H); 3.35(m,2H); 3.52(m,2H); 4.32(s,2H); 8.75(b,1H); 9.04(b,1H); 10.05(b,1H).

Step D

2-Iminopiperazine hydrochloride

Hydrogen chloride gas was bubbled through 6 mL of ethyl acetate at 0° C. for 3 mins. Solid 4-t-butoxycarbonyl-2-iminopiperazine hydrochloride (36 mg) was added and the mixture was stirred overnight at room temperature. Solvent and hydrochloric acid gas were evaporated in vacuo to give 24 mg of the desired iminopiperazine hydrochloride as a white solid.

$^1$H NMR (DMSO): 3.35(3H); 3.54(m,2H); 4.12(s,2H); 8.98(b,1H); 9.3(b,1H); 10.16(b,1H)

EXAMPLE 24

2-Imino-decahydro-cis-quinoxaline

Step A

Decahydro-2(1H)-quinoxalinone

To a solution of 2.28 g (20 mmol) of cis-1,2-diaminocyclohexane in 100 mL of water 1.74 g (30 mmol) of glyoxal was added. After stirring for 4 h the reaction mixture was filtered and the filtrate was concentrated in vacuo. The residual oil was absorbed on a flash column and the column was eluted with 50% EtOAc/hexane, 10% MeOH/EtOAc and 50% MeOH/EtOAc to isolate 1.19 g of the title compound as an oil.

Step B 4-t-Butyloxycarbonyl-decahydro-2(1H)-quinoxalinone

A solution of 1.19 g (7.72 mmol) of decahydro-2(1H)-quinxalinone in 10 mL of saturated NaHCO$_3$ was treated with 2.2 g (10 mmol) of di-tert-butyl dicarbonate. After stirring for 2 h the reaction mixture was extracted with EtOAc and the EtOAc layer was washed with brine and dried. The filtrate was concentrated and the residue was purified on a flash column to isolate 0.667 g of the title compound.

Step C 4-t-Butyloxycarbonyl-2-methoxy-3,4,5,6,7,8,5a,8,a-octahydro-quinoxalinone.

To a solution of 0.254 g (1 mmol) of 4-t-butyloxycarbonyl-decahydro-2(1H)-quinoxalinone in 3 mL of CH$_2$Cl$_2$ was added 0.191 g (1.3 mmol) of trimethyloxonium tetrafluoroborate and the mixture was stirred overnight. The reaction mixture was partitioned between saturated NaHCO$_3$ and CH$_2$Cl$_2$. The organic layer was washed with water, brine dried and concentrated. The residue was chromatographed using 20% Et$_2$O-hexane as an eluent to isolate 0.124 g of the title compound.

Step D 4-t-Butoxy-2-imino-decahydro-cis-quinoxaline

A solution of 0.123 g (0.45 mmol) of 4-t-Butyloxycarbonyl-2-methoxy-3,4,5,6,7,8,5a,8,a-octahydro-quinoxalinone in 3 mL of EtOH containing 22 mg (0.41 mmol) of NH4Cl was heated to reflux. After 3 h at reflux the reaction mixture was concentrated, the residue was triturated with Et$_2$O and the solid was filtered and dried to isolate 0.055 mg of the title compound.

Step E

2-Imino-decahydro-cis-quinoxaline

To 46 mg of 4-t-butoxy-2-imino-decahydro-cis-quinoxaline 3 mL of EtOAc saturated with HCl was added. The reaction turned clear momentarily and another solid was formed. After 30 min the solid was filtered washed with Et$_2$O and dried to furnish 32 mg of the title compound.

$^1$H NMR (D$_2$O): 1.50 (br s, 3H), 1.66 (br,1H), 1.89 (br s, 4H), 3.92 (m, 1H), 4.0 (m, 1H), 4.37 (s, 2H)

EXAMPLE 25

2-Imino-decahydro-trans-quinoxaline

The title compound was prepared by the procedure of example 24 starting with trans-1,2-diaminocyclohexane.

$^1$H NMR (D$_2$O): 1.3–1.6 (m, 4H), 1.8–1.9 (m, 2H), 2.16 (t, 2H), 3.3 (td, 1H, J=11 and 4 Hz), 3.55 (td, 1H, J=11 and 4 Hz), 4.41 (ABq, 2H)

What is claimed is:

1. A compound of Formula Ia

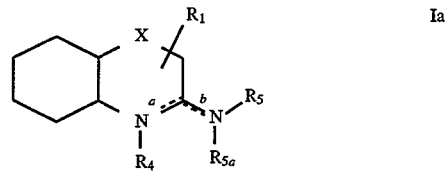

or a pharmaceutically acceptable salt thereof wherein:
 side a or side b has a double bond;
 X is selected from $C_{12}R_{13}$, O, $S(O)_m$, NH, and —N(C$_{1-6}$alkyl)—;
 m is 0, 1 or 2;
 $R_1$, $R_{12}$, and $R_{13}$ are each independently selected from the group consisting of
  (a) hydrogen,
  (b) $C_{1-12}$alkoxy,
  (c) $C_{1-12}$alkylS(O)$_k$ wherein k is 0, 1 or 2,
  (d) mono $C_{1-12}$alkylamino,
  (e) (di-$C_{1-12}$alkyl)amino,
  (f) $C_{1-12}$alkylcarbonyl,
  (g) $C_{1-12}$alkyl,
  (h) $C_{2-12}$alkenyl,
  (i) $C_{2-12}$alkynyl,
  (j) $C_{5-10}$cycloalkyl,
  (k) hetero $C_{5-10}$cycloalkyl, wherein the hetero $C_{5-10}$cycloalkyl optionally contains 1 or 2 heteroatoms selected from S, O and N,
  (l) aryl, selected from phenyl or naphthyl,
  (m) heteroaryl, wherein heteroaryl is selected from the group consisting of:
   (1) benzimidazolyl,
   (2) benzofuranyl,
   (3) benzooxazolyl,
   (4) furanyl,
   (5) imidazolyl,
   (6) indolyl,
   (7) isooxazolyl,
   (8) isothiazolyl,
   (9) oxadiazolyl,
   (10) oxazolyl,
   (11) pyrazinyl,
   (12) pyrazolyl,
   (13) pyridyl,
   (14) pyrimidyl,
   (15) pyrrolyl,
   (17) isoquinolyl,
   (18) tetrazolyl,
   (19) thiadiazolyl,
   (20) thiazolyl,

(21) thienyl, and
(22) triazolyl,
(n) amino,
(o) oxo,
(p) C(O)OH,
(q) C(O)OR$_6$, R$_6$ is selected from hydrogen, phenyl, cyclohexyl or C$_{1-6}$alkyl,
each of (b) to (m) being optionally mono or di-substituted the substituents being independently selected from
(1) hydroxy,
(2) carboxy,
(3) —NR$_6$R$_7$, where R$_7$ is selected from hydrogen, phenyl, cyclohexyl or C$_{1-6}$alkyl,
(4) —OR$_6$,
(5) —C(O)OR$_6$,
(6) —S(O)$_k$R$_6$,
(7) halo selected from F, Cl, Br and I,
(8) —C(=NR$_6$)—NHR$_7$,
(9) —S—C(=NR$_6$)—NHR$_7$,
(r) hydroxy;
R$_4$, R$_5$ and R$_{5a}$ are each independently selected from the group consisting of
(a) hydrogen,
(b) linear and branched C$_{1-12}$alkyl, optionally mono or di-substituted, the substituents being independently selected from
(1) hydroxy,
(2) carboxy,
(3) —NR$_6$R$_7$,
(4) —OR$_6$,
(5) —C(O)OR$_6$,
(6) —S(O)$_k$R$_6$,
(7) halo selected from F, Cl, Br and I,
(8) phenyl, optionally mono or di-substituted with hydroxy, halo, C$_{1-4}$alkyl, or C$_{1-4}$alkoxy,
(c) —C(O)NR$_8$R$_9$, where R$_8$ and R$_9$ are each independently hydrogen, phenyl, cyclohexyl or C$_{1-6}$alkyl, said C$_{1-6}$alkyl optionally substituted by
(1) hydroxy,
(2) amino,
(3) carboxy,
(4) —NR$_{10}$R$_{11}$, wherein R$_{10}$ and R$_{11}$ are each independently H, Cl$_{1-6}$alkyl, phenyl or benzyl,
(5) —OR$_{10}$,
(6) —C(O)OR$_{10}$,
(7) —S(O)$_m$R$_{10}$, where m is 0, 1 or 2,
(8) halo selected from F, Cl, Br and I,
(9) optionally substituted aryl wherein aryl and aryl substituents are as defined above,
(10) optionally substituted heteroaryl wherein heteroaryl and heteroaryl substituents are as defined above,
(11) optionally substituted C5-10cycloalkyl wherein cycloalkyl and cycloalkyl substituents are as defined above,
(12) optionally substituted hetero C$_{5-10}$cycloalkyl wherein hetero cycloalkyl and hetero cycloalkyl substituents are as defined above,
(d) —C(S)NR$_8$R$_9$,
(e) —C(O)R$_9$,
(f) —C(O)OR$_9$,
(g) —C(S)R$_9$,
(h) phenyl,
(i) cyclohexyl,
provided that R$_4$ is present only when side a is a single bond and R$_{5a}$ is present only when side b is a single bond.

2. A compound according to claim 1 wherein:
X is selected from CR$_{12}$R$_{13}$, O, S(O)$_m$, NH, and —N(C$_{1-6}$alkyl)—;
m is 0, 1 or 2;
R$_1$, R$_{12}$ and R$_{13}$ are each independently selected from the group consisting of
(a) hydrogen,
(b) C$_{1-6}$alkoxy,
(c) C$_{1-6}$alkylamino,
(d) C$_{1-6}$alkylcarbonyl,
(e) C$_{1-6}$alkyl,
(f) C$_{2-6}$alkenyl,
(g) C$_{2-6}$alkynyl,
(h) C$_5$, C$_6$ or C$_7$cycloalkyl,
(i) hetero C$_5$, C$_6$ or C$_7$cycloalkyl, wherein the hetero C$_5$, C$_6$ or C$_7$cycloalkyl optionally contains 1 or 2 heteroatoms selected from S, O and N,
(j) aryl, selected from phenyl or naphthyl,
(k) heteroaryl, wherein heteroaryl is selected from the group consisting of:
(1) benzimidazolyl,
(2) benzofuranyl,
(3) benzooxazolyl,
(4) furanyl,
(5) imidazolyl,
(6) indolyl,
(7) isooxazolyl,
(8) isothiazolyl,
(9) oxadiazolyl,
(10) oxazolyl,
(11) pyrazinyl,
(12) pyrazolyl,
(13) pyridyl,
(14) pyrimidyl,
(15) pyrrolyl,
(16) quinolyl,
(17) tetrazolyl,
(18) thiadiazolyl,
(19) thiazolyl,
(20) thienyl, and
(21) triazolyl,
(l) hydroxy,
each of (b) to (k) being optionally mono or di-substituted the substituents being independently selected from
(1) hydroxy,
(2) carboxy,
(3) —NR$_6$R$_7$, where R$_6$ and R$_7$ are selected from hydrogen, phenyl, cyclohexyl or C$_{1-6}$alkyl,
(4) —OR$_6$,
(5) —C(O)OR$_6$,
(6) —S(O)$_k$R$_6$, where k is 0, 1 or 2,
(7) halo selected from F, Cl, Br and I,
(8) —C(=NR$_6$)—NHR$_7$,
(9) —S—C(=NR$_6$)—NHR$_7$;
R$_4$, R$_5$ and R$_{5a}$ are each independently selected from the group consisting of
(a) hydrogen,
(b) linear and branched C$_{1-6}$alkyl, optionally mono or di-substituted, the substituents being independently selected from
(1) hydroxy,
(2) carboxy,
(3) —NR$_6$R$_7$,
(4) —OR$_6$,
(5) —C(O)OR$_6$,
(6) —S(O)$_k$R$_6$, where k is 0, 1 or 2, (7) halo selected from F, Cl, Br and I, (c) —C(O)NR$_8$R$_9$, where R$_8$ and R$_9$ are each independently hydrogen, phenyl, cyclohexyl or C$_{1-4}$alkyl, said C$_{1-4}$alkyl optionally substituted by
(1) hydroxy,
(2) amino,
(3) carboxy,
(4) —NR$_{10}$R$_{11}$, wherein R$_{10}$ and R$_{11}$ are each independently H, C$_{1-4}$alkyl, phenyl or benzyl,
(5) —OR$_{10}$,
(6) —C(O)OR$_{10}$,
(7) —S(O)$_m$R$_{10}$, where m is 0, 1 or 2,
(8) halo selected from F, Cl, Br and I,
(9) optionally substituted aryl wherein aryl and aryl substituents are as defined above,
(10) optionally substituted heteroaryl wherein heteroaryl and heteroaryl substituents are as defined above,
(11) optionally substituted C$_5$, C$_6$ or C$_7$cycloalkyl wherein cycloalkyl and cycloalkyl substituents are as defined above,
(12) optionally substituted hetero C$_5$, C$_6$ or C$_7$cycloalkyl wherein hetero cycloalkyl and hetero cycloalkyl substituents are as defined above, (d) —C(S)NR$_8$R$_9$,
(e) —C(O)R$_9$,
(f) —C(O)OR$_9$,
(g) —C(S)R$_9$,
(h) phenyl, and
(i) cyclohexyl.

3. A compound according to claim 2 wherein:

X is selected from CR$_{12}$R$_{13}$, O, NH, and —N(C$_{1-4}$alkyl)—;

R$_1$, R$_{12}$ and R$_{13}$ are each independently selected from the group consisting of
(a) hydrogen,
(b) C$_{1-6}$alkoxy,
(c) C$_{1-6}$alkylamino,
(d) C$_{1-6}$alkylcarbonyl,
(e) C$_{1-6}$alkyl,
(f) C$_{2-6}$alkenyl,
(g) C$_5$, C$_6$ or C$_7$cycloalkyl,
(h) hetero C$_5$ or C$_6$ cycloalkyl, wherein the hetero C$_5$ or C$_6$ cycloalkyl optionally contains 1 heteroatom selected from S, O and N,
(i) aryl, selected from phenyl or naphthyl,
(j) heteroaryl, wherein heteroaryl is selected from the group consisting of:
(1) furanyl,
(2) pyrazinyl,
(3) pyrazolyl,
(4) pyridyl,
(5) pyrimidyl,
(6) thiazolyl,
(7) thienyl, and
(8) triazolyl,
(k) hydroxy,
each of (b) to (j) being optionally mono or di-substituted the substituents being independently selected from
(1) hydroxy,
(2) carboxy,
(3) —NR$_6$R$_7$, wherein R$_6$ and R$_7$ are each independently hydrogen or C$_{1-4}$alkyl,
(4) —OR$_6$,
(5) —C(O)OR$_6$,
(6) —S(O)$_k$R$_6$, where k is 0, 1 or 2,
(7) halo selected from F, Cl, Br and I,
(8) —C(=NR$_6$)—NHR$_7$,
(9) —S—C(=NR$_6$)—NHR$_7$;

R$_4$, R$_5$ and R$_{5a}$ are each independently selected from the group consisting of
(a) hydrogen,
(b) linear and branched C$_{1-6}$alkyl, optionally mono or di-substituted, the substituents being independently selected from
(1) hydroxy,
(2) carboxy,
(3) —NR$_6$R$_7$,
(4) —OR$_6$,
(5) —C(O)OR$_6$,
(6) —S(O)$_k$R$_6$,
(7) halo selected from F, Cl, Br and I, (c) —C(O)NR$_8$R$_9$, where R$_8$ and R$_9$ are each independently hydrogen, phenyl, cyclohexyl or C$_{1-4}$alkyl, said C$_{1-4}$alkyl optionally substituted by
(1) hydroxy,
(2) amino,
(3) carboxy,
(4) —NR$_{10}$R$_{11}$, wherein R$_{10}$ and R$_{11}$ are each independently H, C$_{1-4}$alkyl, phenyl or benzyl,
(5) —OR$_{10}$,
(6) —C(O)OR$_{10}$,
(7) —S(O)$_m$R$_{10}$, where m is 1 or 2,
(8) halo selected from F, Cl, Br and I,
(9) optionally substituted aryl wherein aryl and aryl substituents are as defined above,
(10) optionally substituted heteroaryl wherein heteroaryl and heteroaryl substituents are as defined above,
(11) optionally substituted C$_5$ or C$_6$ cycloalkyl wherein cycloalkyl and cycloalkyl substituents are as defined above,
(12) optionally substituted hetero C$_5$ or C$_6$ cycloalkyl wherein hetero cycloalkyl and hetero cycloalkyl substituents are as defined above, (d) —C(S)NR$_8$R$_9$,
(e) —C(O)R$_9$,
(f) —C(O)OR$_9$,
(g) —C(S)R$_9$,
(h) phenyl,
(i) cyclohexyl.

4. A compound according to claim 3 wherein:

X is selected from CR$_{12}$R$_{13}$, NH, and —N(C$_{1-4}$alkyl)—;

R$_1$, R$_{12}$ and R$_{13}$ are selected from the group consisting of
(a) hydrogen,
(b) C$_{1-4}$alkoxy,
(c) C$_{1-4}$alkylamino,
(d) C$_{1-4}$alkylcarbonyl,
(e) linear and branched C$_{1-4}$alkyl,
(f) hydroxy,
each of (b) to (e) being optionally mono or di-substituted the substituents being independently selected from
(1) hydroxy,
(2) carboxy,
(3) —NR$_6$R$_7$, wherein R$_6$ and R$_7$ are each independently hydrogen or C$_{1-3}$alkyl,
(4) —OR$_6$,
(5) —C(O)OR$_6$,
(6) —S(O)$_k$R$_6$, where k is 0, 1 or 2,
(7) halo selected from F, Cl, Br and I;

R$_4$, R$_5$ and R$_{5a}$ are each independently selected from the group consisting of (a) hydrogen,
(b) —C(O)NR$_8$R$_9$, where R$_8$ and R$_9$ are each independently hydrogen or C$_{1-3}$alkyl, said C$_{1-3}$alkyl optionally substituted by
  (1) hydroxy,
  (2) amino,
  (3) carboxy,
  (4) —NR$_{10}$R$_{11}$, wherein R$_{10}$ and R$_{11}$ are each independently H or C$_{1-3}$alkyl,
  (5) —OR$_{10}$,
  (6) —C(O)OR$_{10}$,
  (7) —S(O)$_m$R$_{10}$, where m is 0, 1 or 2,
  (8) halo selected from F, Cl, Br and I,
(c) —C(S)NR$_8$R$_9$,
(d) —C(O)R$_9$,
(e) —C(O)OR$_9$,
(f) —C(S)R$_9$,
(g) —C(S)HR$_9$, and
(h) —C$_{1-4}$alkyl.

5. A compound according to claim 4 wherein:

X is selected from CR$_{12}$R$_{13}$, NH, and —N(C$_{1-4}$alkyl)—;

R$_1$, R$_{12}$ and R$_{13}$ are selected from the group consisting of
  (a) hydrogen,
  (b) C$_{1-4}$alkoxy,
  (c) C$_{1-4}$alkylamino,
  (d) C$_{1-4}$alkylcarbonyl,
  (e) linear and branched C$_{1-4}$alkyl,
  (f) hydroxy,
  each of (b) to (e) being optionally mono or di-substituted the substituents being independently selected from
    (1) hydroxy,
    (2) carboxy,
    (3) —NR$_6$R$_7$, wherein R$_6$ and R$_7$ are each independently hydrogen or C$_{1-3}$alkyl,
    (4) —OR$_6$,
    (5) —C(O)OR$_6$,
    (6) —S(O)$_k$R$_6$, where k is 0, 1 or 2,
    (7) halo selected from F, Cl, Br and I;

R$_4$ is selected from the group consisting of
  (a) hydrogen,
  (b) —C(O)NHR$_9$, where R$_9$ is hydrogen or C$_{1-3}$alkyl, said C$_{1-3}$alkyl optionally substituted by
    (1) hydroxy,
    (2) amino,
    (3) carboxy,
    (4) —NR$_{10}$R$_{11}$, wherein R$_{10}$ and R$_{11}$ are each independently C$_{1-3}$alkyl,
    (5) —OR$_{10}$,
    (6) —C(O)OR$_{10}$,
    (7) —S(O)$_m$R$_{10}$, where m is 1 or 2,
    (8) halo selected from F, Cl, Br and I,
  (c) —C(S)NHR$_9$,
  (d) —C$_{1-4}$alkyl;

R$_5$ is selected from the group consisting of
  (a) hydrogen,
  (b) —C(O)NHR$_9$,
  (c) —C(S)NR$_8$R$_9$,
  (d) —C$_{1-4}$alkyl; and R$_{5a}$ is hydrogen.

6. A compound of Formula Ia

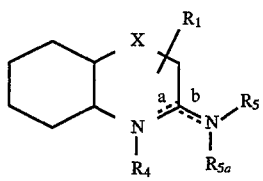

or a pharmaceutically acceptable salt thereof wherein:
  side a or side b has a double bond;
  X is selected from CR$_{12}$R$_{13}$, O, S(O)$_m$, NH, and —N(C$_{1-6}$alkyl)—;
  m is 0, 1 or 2;
  R$_1$ and R$_{12}$ are each independently selected from the group consisting of
    (a) hydrogen,
    (b) C$_{1-12}$alkoxy,
    (c) C$_{1-12}$alkylS(O)$_k$ wherein k is 0, 1 or 2,
    (d) mono C$_{1-12}$alkylamino,
    (e) (di-C$_{1-12}$alkyl)amino,
    (f) C$_{1-12}$alkylcarbonyl,
    (g) C$_{1-12}$alkyl,
    (h) C$_{2-12}$alkenyl,
    (i) C$_{2-12}$alkynyl,
    (j) C$_{5-10}$cycloalkyl,
    (k) hetero C$_{5-10}$cycloalkyl, wherein the hetero C$_{5-10}$cycloalkyl optionally contains 1 or 2 heteroatoms selected from S, O and N,
    (l) aryl, selected from phenyl or naphthyl,
    (m) heteroaryl, wherein heteroaryl is selected from the group consisting of:
      (1) benzimidazolyl,
      (2) benzofuranyl,
      (3) benzooxazolyl,
      (4) furanyl,
      (5) imidazolyl,
      (6) indolyl,
      (7) isooxazolyl,
      (8) isothiazolyl,
      (9) oxadiazolyl,
      (10) oxazolyl,
      (11) pyrazinyl,
      (12) pyrazolyl,
      (13) pyridyl,
      (14) pyrimidyl,
      (15) pyrrolyl,
      (17) isoquinolyl,
      (18) tetrazolyl,
      (19) thiadiazolyl,
      (20) thiazolyl,
      (21) thienyl, and
      (22) triazolyl,
    (n) amino,
    (o) oxo,
    (p) C(O)OH,
    (q) C(O)OR$_6$, R$_6$ is selected from hydrogen, phenyl, cyclohexyl or C$_{1-6}$alkyl,
    each of (b) to (m) being optionally mono or di-substituted the substituents being independently selected from
      (1) hydroxy,
      (2) carboxy,
      (3) —NR$_6$R$_7$, where R$_7$ is selected from hydrogen, phenyl, cyclohexyl or C$_{1-6}$alkyl,
      (4) —OR$_6$,
      (5) —C(O)OR$_6$, (6) —S(O)$_k$R$_6$,
(7) halo selected from F, Cl, Br and I,
(8) —C(=NR$_6$)—NHR$_7$,
(9) —S—C(=NR$_6$)—NHR$_7$,
(r) hydroxy;

R$_{13}$ is selected from the group consisting of
(a) C$_{1-12}$alkoxy,
(b) C$_{1-12}$alkylS(O)$_k$ wherein k is 0, 1 or 2,
(c) mono C$_{1-12}$alkylamino,
(d) (di-C$_{1-12}$alkyl)amino,
(e) C$_{1-12}$alkylcarbonyl,
(f) C$_{1-12}$alkyl,
(g) C$_{2-12}$alkenyl,
(h) C$_{2-12}$alkynyl,
(i) C$_{5-10}$cycloalkyl,
(j) hetero C$_{5-10}$cycloalkyl, wherein the hetero C$_{5-10}$cycloalkyl optionally contains 1 or 2 heteroatoms selected from S, O and N,
(k) aryl, selected from phenyl or naphthyl,
(l) heteroaryl, wherein heteroaryl is selected from the group consisting of:
  (1) benzimidazolyl,
  (2) benzofuranyl,
  (3) benzooxazolyl,
  (4) furanyl,
  (5) imidazolyl,
  (6) indolyl,
  (7) isooxazolyl,
  (8) isothiazolyl,
  (9) oxadiazolyl,
  (10) oxazolyl,
  (11) pyrazinyl,
  (12) pyrazolyl,
  (13) pyridyl,
  (14) pyrimidyl,
  (15) pyrrolyl,
  (17) isoquinolyl,
  (18) tetrazolyl,
  (19) thiadiazolyl,
  (20) thiazolyl,
  (21) thienyl, and
  (22) triazolyl,
(m) amino,
(n) oxo,
(o) C(O)OH,
(p) C(O)OR$_6$, R$_6$ is selected from hydrogen, phenyl, cyclohexyl or C$_{1-6}$alkyl,
each of (a) to (l) being optionally mono or di-substituted the substituents being independently selected from
  (1) hydroxy,
  (2) carboxy,
  (3) —NR$_6$R$_7$, where R$_7$ is selected from hydrogen, phenyl, cyclohexyl or C$_{1-6}$alkyl,
  (4) —OR$_6$,
  (5) —C(O)OR$_6$,
  (6) —S(O)$_k$R$_6$,
  (7) halo selected from F, Cl, Br and I,
  (8) —C(=NR$_6$)—NHR$_7$,
  (9) —S—C(=NR$_6$)—NHR$_7$,
(q) hydroxy;

R$_4$, R$_5$ and R$_{5a}$ are each independently selected from the group consisting of
(a) hydrogen,
(b) linear and branched C$_{1-12}$alkyl, optionally mono or di-substituted, the substituents being independently selected from
  (1) hydroxy,
  (2) carboxy,
  (3) —NR$_6$R$_7$,
  (4) —OR$_6$,
  (5) —C(O)OR$_6$,
  (6) —S(O)$_k$R$_6$,
  (7) halo selected from F, Cl, Br and I,
  (8) phenyl, optionally mono or di-substituted with hydroxy, halo, C$_{1-4}$alkyl, or C$_{1-4}$alkoxy,
(c) —C(O)NR$_8$R$_9$, where R$_8$ and R$_9$ are each independently hydrogen, phenyl, cyclohexyl or C$_{1-6}$alkyl, said C$_{1-6}$alkyl optionally substituted by
  (1) hydroxy,
  (2) amino,
  (3) carboxy,
  (4) —NR$_{10}$R$_{11}$, wherein R$_{10}$ and R$_{11}$ are each independently H, C$_{1-6}$alkyl, phenyl or benzyl,
  (5) —OR$_{10}$,
  (6) —C(O)OR$_{10}$,
  (7) —S(O)$_m$R$_{10}$, where m is 0, 1 or 2,
  (8) halo selected from F, Cl, Br and I,
  (9) optionally substituted aryl wherein aryl and aryl substituents are as defined above,
  (10) optionally substituted heteroaryl wherein heteroaryl and heteroaryl substituents are as defined above,
  (11) optionally substituted C$_{5-10}$cycloalkyl wherein cycloalkyl and cycloalkyl substituents are as defined above,
  (12) optionally substituted hetero C$_{5-10}$cycloalkyl wherein hetero cycloalkyl and hetero cycloalkyl substituents are as defined above,
(d) —C(S)NR$_8$R$_9$,
(e) —C(O)R$_9$,
(f) —C(O)OR$_9$,
(g) —C(S)R$_9$,
(h) phenyl,
(i) cyclohexyl,
provided that R$_4$ is present only when side a is a single bond and R$_{5a}$ is present only when side b is a single bond.

7. A compound of Formula Ia

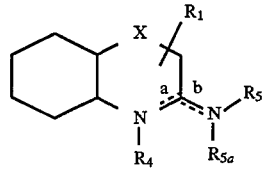

Ia or a pharmaceutically acceptable salt thereof wherein:
side a or side b has a double bond;
X is selected from CH$_2$, CR$_{12}$R$_{13}$, O, S(O)$_m$, NH, and —N(C$_{1-6}$alkyl)—;
m is 0, 1 or 2;
R$_1$, R$_{12}$ and R$_{13}$ are each independently selected from the group consisting of
(a) hydrogen,
(b) C$_{1-12}$alkoxy,
(c) C$_{1-12}$alkylS(O)$_k$ wherein k is 0, 1 or 2,
(d) mono C$_{1-12}$alkylamino,
(e) (di-C$_{1-12}$alkyl)amino,
(f) C$_{1-12}$alkylcarbonyl,
(g) C$_{1-12}$alkyl,
(h) C$_{2-12}$alkenyl,
(i) C$_{2-12}$alkynyl,
(j) C$_{5-10}$cycloalkyl,
(k) hetero C$_{5-10}$cycloalkyl, wherein the hetero C$_{5-10}$cycloalkyl optionally contains 1 or 2 heteroatoms selected from S, O and N, (i) aryl, selected from phenyl or naphthyl,
(m) heteroaryl, wherein heteroaryl is selected from the group consisting of:
  (1) benzimidazolyl,
  (2) benzofuranyl,
  (3) benzooxazolyl,
  (4) furanyl,
  (5) imidazolyl,
  (6) indolyl,
  (7) isooxazolyl,
  (8) isothiazolyl,
  (9) oxadiazolyl,
  (10) oxazolyl,
  (11) pyrazinyl,
  (12) pyrazolyl,
  (13) pyridyl,
  (14) pyrimidyl,
  (15) pyrrolyl,
  (17) isoquinolyl,
  (18) tetrazolyl,
  (19) thiadiazolyl,
  (20) thiazolyl,
  (21) thienyl, and
  (22) triazolyl,
(n) amino,
(o) oxo,
(p) C(O)OH,
(q) C(O)OR$_6$, R$_6$ is selected from hydrogen, phenyl, cyclohexyl or C$_{1-6}$alkyl,
each of (b) to (m) being optionally mono or di-substituted the substituents being independently selected from
  (1) hydroxy,
  (2) carboxy,
  (3) —NR$_6$R$_7$, where R$_7$ is selected from hydrogen, phenyl, cyclohexyl or C$_{1-6}$alkyl,
  (4) —OR$_6$,
  (5) —C(O)OR$_6$,
  (6) —S(O)$_k$R$_6$,
  (7) halo selected from F, Cl, Br and I,
  (8) —C(=NR$_6$)—NHR$_7$,
  (9) —S—C(=NR$_6$)—NHR$_7$,
(r) hydroxy;

R$_4$ and R$_{5a}$ are each independently selected from the group consisting of
(a) hydrogen,
(b) linear and branched C$_{1-12}$alkyl, optionally mono or di-substituted, the substituents being independently selected from
  (1) hydroxy,
  (2) carboxy,
  (3) —NR$_6$R$_7$,
  (4) —OR$_6$,
  (5) —C(O)OR$_6$,
  (6) —S(O)$_k$R$_6$,
  (7) halo selected from F, Cl, Br and I,
  (8) phenyl, optionally mono or di-substituted with hydroxy, halo, C$_{1-4}$alkyl, or C$_{1-4}$alkoxy,
(c) —C(O)NR$_8$R$_9$, where R$_8$ and R$_9$ are each independently hydrogen, phenyl, cyclohexyl or C$_{1-6}$alkyl, said C$_{1-6}$alkyl optionally substituted by
  (1) hydroxy,
  (2) amino,
  (3) carboxy,
  (4) —NR$_{10}$R$_{11}$, wherein R$_{10}$ and R$_{11}$ are each independently H, C$_{1-6}$alkyl, phenyl or benzyl,
  (5) —OR$_{10}$,
  (6) —C(O)OR$_{10}$,
  (7) —S(O)$_m$R$_{10}$, where m is 0, 1 or 2,
  (8) halo selected from F, Cl, Br and I,
  (9) optionally substituted aryl wherein aryl and aryl substituents are as defined above,
  (10) optionally substituted heteroaryl wherein heteroaryl and heteroaryl substituents are as defined above,
  (11) optionally substituted C$_{5-10}$cycloalkyl wherein cycloalkyl and cycloalkyl substituents are as defined above,
  (12) optionally substituted hereto C$_{5-10}$cycloalkyl wherein hetero cycloalkyl and hetero cycloalkyl substituents are as defined above,
(d) —C(S)NR$_8$R$_9$,
(e) —C(O)R$_9$,
(f) —C(O)OR$_9$,
(g) —C(S)R$_9$,
(h) phenyl,
(i) cyclohexyl;

R$_5$ is selected from the group consisting of
(a) linear and branched C$_{1-12}$alkyl, optionally mono or di-substituted, the substituents being independently selected from
  (1) hydroxy,
  (2) carboxy,
  (3) —NR$_6$R$_7$,
  (4) —OR$_6$,
  (5) —C(O)OR$_6$,
  (6) —S(O)$_k$R$_6$,
  (7) halo selected from F, Cl, Br and I,
  (8) phenyl, optionally mono or di-substituted with hydroxy, halo, C$_{1-4}$alkyl, or C$_{1-4}$alkoxy,
(b) —C(O)NR$_8$R$_9$, where R$_8$ and R$_9$ are each independently hydrogen, phenyl, cyclohexyl or C$_{1-6}$alkyl, said C$_{1-6}$alkyl optionally substituted by
  (1) hydroxy,
  (2) amino,
  (3) carboxy,
  (4) —NR$_{10}$R$_{11}$, wherein R$_{10}$ and R$_{11}$ are each independently H, C$_{1-6}$alkyl, phenyl or benzyl,
  (5) —OR$_{10}$,
  (6) —C(O)OR$_{10}$,
  (7) —S(O)$_m$R$_{10}$, where m is 0, 1 or 2,
  (8) halo selected from F, Cl, Br and I,
  (9) optionally substituted aryl wherein aryl and aryl substituents are as defined above,
  (10) optionally substituted heteroaryl wherein heteroaryl and heteroaryl substituents are as defined above,
  (11) optionally substituted C$_{5-10}$cycloalkyl wherein cycloalkyl and cycloalkyl substituents are as defined above,
  (12) optionally substituted hetero C$_{5-10}$cycloalkyl wherein hetero cycloalkyl and hetero cycloalkyl substituents are as defined above,
(c) —C(S)NR$_8$R$_9$,
(d) —C(O)R$_9$,
(e) —C(O)OR$_9$,
(f) —C(S)R$_9$,
(g) phenyl,
(h) cyclohexyl, provided that R$_4$ is present only when side a is a single bond and R$_{5a}$ is present only when side b is a single bond.

8. A compound of claim 1 selected from
(a) cis-Decahydro-2-iminoquinoline hydrochloride,
(b) trans-Decahydro-2-iminoquinoline hydrochloride, (c) cis-2-Imino-4-methyl-decahydroquinoline hydrochloride, (d) 2-Imino-decahydro-cis-quinoxaline, and (e) 2-Imino-decahydro-trans-quinoxaline.

9. A pharmaceutical composition for treating a nitric oxide synthase mediated disease comprising a pharmaceutical carrier and a non-toxic effective amount of the compound according to claim 1.

10. A pharmaceutical composition for treating a nitric oxide synthase mediated disease comprising a pharmaceutical carrier and a non-toxic effective amount of the compound according to claim 6.

11. A pharmaceutical composition for treating a nitric oxide synthase mediated disease comprising a pharmaceutical carrier and a non-toxic effective amount of the compound according to claim 7.

12. A pharmaceutical composition for treating a nitric oxide synthase mediated disease comprising a pharmaceutical carrier and a non-toxic effective amount of the compound according to claim 8.

13. A method for inhibiting the activity of nitric oxide synthases comprising administering to a subject suffering from a nitric oxide synthase mediated disease, a non-toxic therapeutically effective amount of the compound of claim 1.

14. A method for inhibiting the activity of nitric oxide synthases comprising administering to a subject suffering from a nitric oxide synthase mediated disease, a non-toxic therapeutically effective amount of the compound of claim 6.

15. A method for inhibiting the activity of nitric oxide synthases comprising administering to a subject suffering from a nitric oxide synthase mediated disease, a non-toxic therapeutically effective amount of the compound of claim 7.

16. A method for inhibiting the activity of nitric oxide synthases comprising administering to a subject suffering from a nitric oxide synthase mediated disease, a non-toxic therapeutically effective amount of the compound of claim 8.

* * * * *